United States Patent [19]
Shih et al.

[11] Patent Number: 5,446,069

[45] Date of Patent: Aug. 29, 1995

[54] BENZOALKANO COMPOUNDS AND THEIR USE FOR TREATING HYPERPROLIFERATIVE DISEASES

[75] Inventors: Neng-Yang Shih, North Caldwell, N.J.; Pietro Mangiaracina, Monsey, N.Y.; Michael J. Green, Skillman; Ashit K. Ganguly, Upper Montclair, both of N.J.

[73] Assignee: Schering Corporation, Kenilworth, N.J.

[21] Appl. No.: 37,865

[22] Filed: Mar. 29, 1993

Related U.S. Application Data

[60] Division of Ser. No. 776,891, Oct. 15, 1991, Pat. No. 5,225,436, which is a continuation of Ser. No. 435,509, Oct. 18, 1989, abandoned, which is a continuation-in-part of Ser. No. 51,108, May 15, 1987, abandoned.

[51] Int. Cl.⁶ ............... A61K 31/385; A61K 31/12; C07D 339/08; C07C 49/88
[52] U.S. Cl. .................. 514/681; 568/327; 514/440; 514/621; 514/649; 514/652; 514/706; 514/712; 514/717; 514/724; 549/31; 549/2; 549/80; 549/35; 549/39; 549/78; 549/333; 549/430
[58] Field of Search .............. 568/327; 514/681

[56] References Cited

U.S. PATENT DOCUMENTS

| | | | |
|---|---|---|---|
| 2,632,024 | 3/1953 | Grob | 568/327 |
| 3,247,253 | 4/1966 | Bencze | 568/327 |
| 3,274,213 | 9/1966 | Lednicer et al. | 260/326.5 |
| 3,313,853 | 4/1967 | Lednicer et al. | 260/570.7 |
| 3,412,146 | 11/1968 | Kofron | 568/327 |
| 3,432,526 | 3/1969 | Galantay et al. | 568/327 |
| 3,458,577 | 7/1969 | Galautry et al. | 568/327 |
| 3,833,726 | 9/1974 | Schwender et al. | 260/590 |
| 3,957,824 | 5/1976 | Hadler et al. | 260/343.2 R |
| 4,045,485 | 8/1977 | Fried et al. | 260/566 A |
| 4,485,117 | 11/1984 | Hudson et al. | 424/331 |
| 5,225,436 | 7/1993 | Shih et al. | 568/327 |

FOREIGN PATENT DOCUMENTS 0201071 11/1986 European Pat. Off. ........... 568/328

477401 11/1969 Switzerland .

*Primary Examiner*—Mukund J. Shah
*Assistant Examiner*—Matthew V. Grumbling
*Attorney, Agent, or Firm*—Henry C. Jeanette; James R. Nelson

[57] ABSTRACT

Disclosed are compounds of formula

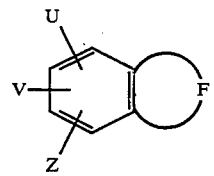

I wherein F represents:

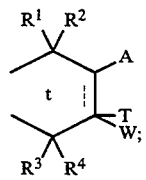

Ia

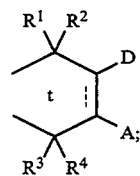

Ib

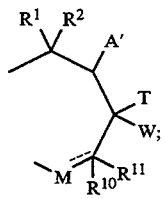

Ic (Abstract continue on next page.)

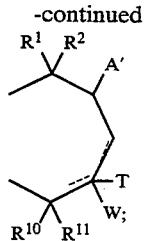
Id
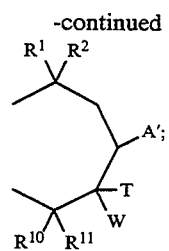
Ie
or
or a pharmaceutically acceptable salt.
The compounds are useful in treating hyperproliferative skin disease, allergic reactions and inflamation.
31 Claims, No Drawings

BENZOALKANO COMPOUNDS AND THEIR USE FOR TREATING HYPERPROLIFERATIVE DISEASES

This application is a divisional of application Ser. No. 07/776,891 filed on Oct. 15, 1991, now U.S. Pat. No. 5,225,436 which in turn is a continuation of application Ser. No. 07/435,509 filed on Oct. 18, 1989 abandoned, which is in turn a continuation in part of U.S. application Ser. No. 07/051,108 filed May 15, 1987 now abandoned, the benefit of which application is claimed pursuant to the provisions of 35 U.S.C. §§120, 363 and 365(c).

BACKGROUND OF THE INVENTION

The present invention relates to certain aryl substituted naphthalene, benzoxepine, benzazepine and benzocycloheptene derivatives.

SUMMARY OF THE INVENTION

The present invention relates to a compound having the structural formula I:

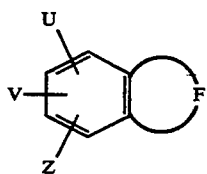

wherein F represents:

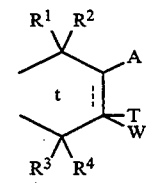   Ia

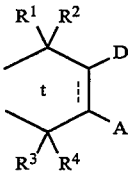   Ib

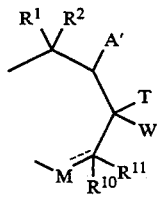   Ic

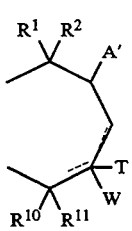   Id

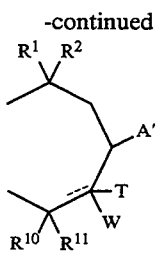   Ie or a pharmaceutically acceptable salt or solvate thereof, wherein:

the dotted line ( - - - ) represents an optional double bond, T being absent in formulas Ia and Id, $R^7$ and $R^{10}$ being absent in Ic when the dotted line represents a double bond;

A represents an aryl or an aromatic heterocylic group;

M represents —$CR^7R^8$, —O— or —$NR^9$;

$A^1$ represents H or A;

T and W are the same or different and each represents H, alkyl, alkenyl, Q, —$OR^5$, —S—alkyl, —SQ, —$CH_2Q$, —$O(CH_2)_nQ$, halo, —$C(O)R^6$, —$CH_2OR^5$, —$O(CH_2)_nCOOR^6$ or —$C(O)OR^6$;

D represents H, alkyl, —$SR^5$, —$C(O)R^5$;

U, V and Z are the same or different and each represents a group selected from H, alkyl, —$OR^5$, —$SR^5$, —$O(CH_2)_nQ$, —$C(O)R^6$, —$CH_2OR^5$, —$O(CH_2)_nCOOR^6$ or halo;

Q represents phenyl or substituted phenyl;

n is 1 to 8;

$R^1$, $R^2$ and $R^3$ are the same or different and each represents H, alkyl, cycloalkylalkyl, alkenyl or alkynyl, which alkyl, alkenyl or alkynyl group may optionally be substituted with a group Q, —$OR^6$, —$SR^6$, halo or —$N(R^6)_2$, with the proviso that OH or $NH_2$ are not directly bonded to the carbon atom of a carbon—carbon double or triple bond, and that in compounds of formula Ia and Ib, $R^1$ and $R^2$ cannot both be H;

$R^4$ represents H, OH, $N(R^6)_2$, —$NR^6(COR^6)$ or —SQ;

in addition, $R^1$ and $R^2$ together with the carbon atom of the ring t to which they are attached may represent a spirocarbocyclic ring having from 3 to 6 carbon atoms;

in addition, $R^3$ and $R^4$ together may represent a carbonyl oxygen =S, =N—$OR^5$, =N—$N(R^6)_2$, =N—$NHC(O)R^6$, =N—$NH(SO_2)R^6$, =N—NH-C(O)$NH_2$,

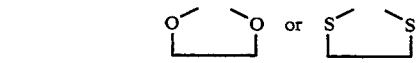

with the proviso that $R^1$ and $R^2$ do not represent H when the dotted line represents a double bond;

each $R^5$ independently represents H, alkyl, alkanoyl (the alkyl portion of which may optionally be substituted with halo, —$OR^6$, —$SR^6$, or a group Q), —C(O)—Q, —C(O)—$N(R^6)_2$ or —C(O)—$OR^6$;

each $R^6$ independently represents H, alkyl or Q;

$R^7$ and $R^8$ are the same or different and each represent H or alkyl, alkynyl, alkenyl, —$OR^5$, Q, —S—alkyl, —SQ, —$CH_2Q$, —$COOR^6$ or —$C(O)R^6$;

$R^9$ represents H, alkyl or —C(O) $R^6$;

$R^{10}$ and $R^{11}$ are the same or different and each represent H, alkyl or alkenyl;

in addition, $R^{10}$ and $R^{11}$ together may represent a carbonyl, $=S$, $=N-OR^5$, $=N-N(R^6)_2$, $=N-NHC(O)R^6$, $=N-NH(SO_2)R^6$ or $=N-NHC(O)NH_2$.

In a preferred embodiment the compound is of formula Ia.

W is preferably H, $OR^5$ or alkyl. $R^1$ and $R^2$ and are preferably each independently H or alkyl. U, V and Z are preferably each independently H or $OR^5$. A is preferably aryl, e.g., phenyl or phenyl substituted with 1 or 2 substituents each independently selected from H, alkyl or $OR^5$. $R^3$ and $R^4$ together preferably represent a carbonyl oxygen, $=N-OR^6$, $=N-O(CO)R^6$, $=N-NH(CO)R^6$, $=N-N(R^6)_2$, $=N-NH(SO_2)R^6$ or $=N-NH(CO)NH_2$.

A preferred subgenus of compounds is represented by the structural formula Ig

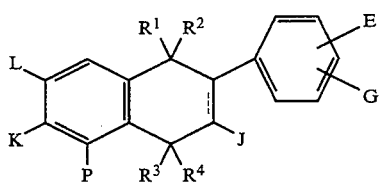

wherein $R^1$ and $R^2$ are the same or different and each is selected from H or alkyl; $R^3$ is H or alkyl and $R^4$ is H or OH, or $R^3$ and $R^4$ together represent a carbonyl oxygen or $=N-OR^6$, wherein $R^6$ is H, alkyl, phenyl or substituted phenyl; E, G, K, L and P are the same or different and each is selected from hydroxy, alkoxy, alkanoyloxy or dialkylcarbamoyloxy; J represents H, hydroxy, alkoxy, alkanoyloxy or dialkylcarbamoyloxy; or a pharmaceutically acceptable salt of such a compound.

Another preferred group of compounds is represented by the structural formula Ih

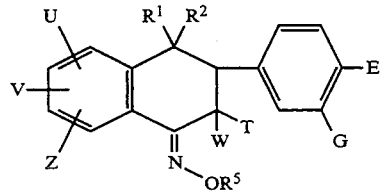

wherein $R^1$ and $R^2$ is alkyl;
$R^5$ is H or alkanoyl;
E, G, U, V and Z are the same or different and each is H, OH or alkoxy;
T and W are the same or different and each is H, alkyl or alkenyl.

A third preferred group of compounds are those of formula Ic, Id or Ie wherein
A is H, phenyl or substituted phenyl or
M is $-CH_2-$, $-O-$ or $-NH-$;
U, V, Z are the same or different and each is H, OH, alkoxy;
$R^1$ and $R^2$ are the same or different and each is H or alkyl;
$R^{10}$ and $R^{11}$ represent H, $-OH$, $-N(R^6)_2$ $-NR^6(COR^6)$ or $R^{10}$ and $R^{11}$ together represent a carbonyl oxygen, $=N-OH$ or $=N-Oalkyl$; and N, T and W are as defined above.

The compounds of the invention may be formulated into pharmaceutical compositions with a pharmaceutically acceptable carrier. The compounds may be used to treat mammals suffering from hyperproliferative skin disease (such as psoriasis), allergic reactions and/or inflammation by administering an effective amount for such purpose to the mammal. Compounds of formula I wherein $R^3$ and $R^4$ together represent $=N-OR^6$ or $=N-NH(CO)R^6$ also inhibit platelet activating factor (PAF) and are thus particularly useful in treating diseases such as allergies, inflammation, etc., mediated by PAF.

DETAILED DESCRIPTION OF THE INVENTION

When utilized herein, the terms listed below have the following scope, unless otherwise indicated:

halo—represents fluoro, chloro or bromo;

alkyl (including the alkyl portion of alkoxy, alkanoyl, alkanoyloxy or cycloalkylalkyl)—represents straight and branched carbon chains and, unless otherwise specified, contains from 1 to 10 carbon atoms;

carbonyl oxygen—represents a group $=O$;

alkanoyl—represents a group

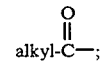

alkenyl—represents straight and branched carbon chains having at least one carbon to carbon double bond and, unless otherwise specified, contains from 3 to 6 carbon atoms;

alkynyl—represents straight and branched carbon chains having at least one carbon to carbon triple bond and, unless otherwise specified, contains from 3 to 6 carbon atoms;

cycloalkyl—(including the cycloalkyl portion of cycloalkylalkyl) represents a saturated carbocyclic ring having from 3 to 7 carbon atoms, e.g., cyclohexyl;

spirocarbocyclic ring—represents a saturated cycloalkyl ring having from 3 to 7 carbon atoms and having one carbon atom thereof common to the ring t in formula Ia or Ib;

aryl—represents a carbocyclic group containing from 6 to 15 carbon atoms and having at least one benzene ring, with all available substitutable carbon atoms thereof being intended as possible points of attachment. More preferably, aryl is phenyl or substituted phenyl;

substituted phenyl—represents phenyl substituted with up to 3 substituents U, V and/or Z as defined above or with a group selected from $-O(C-))-O-$ or $-OCH_2O-$ via adjacent carbon atoms of the phenyl ring. Preferably, the substituents are independently selected from hydroxy, alkoxy, alkanoyloxy or dialkylcarbamoyloxy; and aromatic heterocyclic—represents cyclic groups having at least one O, S and/or N in the ring structure and having a sufficient number of delocalized pi electrons to provide aromatic character, with the aromatic heterocyclic groups preferably containing from 2 to 14 carbon atoms, e.g., 2-, 3- or 4-pyridyl, 2-or 3-furyl, 2- or 3-thienyl, 2-, 4- or 5-thiazolyl, 2- or 4-imidazolyl, 2-, 4-or 5-pyrimidinyl, 2-pyrazinyl, 3- or 4-pyridazinyl, 3-, 5-or 6-[1,2,4- triazinyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, etc., with all available substitutable carbon atoms thereof being intended as a possible point of attachment.

Also, the lines drawn into the rings as in formulas Ia, Ib, and Ic above are intended to indicate that the substituent group may be on any available position on such ring.

Compounds of the invention of formulas Ia and Ib can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of this invention.

Certain compounds of the invention may exist in isomeric forms. The invention contemplates all such isomers both in pure form and in admixture, including racemic mixtures.

Certain compounds of the invention also form pharmaceutically acceptable salts with organic and inorganic acids, e.g., compounds having basic nitrogen atoms. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well know to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of the invention.

Certain compounds of the invention will be acidic in nature, e.g. those compounds wherein U, V or Z is OH. These compounds may form pharmaceutically acceptable salts. Examples of such salts are the sodium, potassium, calcium, aluminum, gold and silver salts. Also contemplated are salts formed with pharmaceutically acceptable amines such as ammonia, alkyl amines, hydroxyalkylamines, N-methylglucamine and the like.

The compounds of formula Ia and Ib can be prepared by the processes A-H described below. In these processes the substituents $R^1$, $R^2$, $R^3$, $R^4$, A, T, U, V, Z, and W are as defined above, unless otherwise indicated.

A. To prepare a compound of formula I wherein $R^3$ and $R^4$ together represent a carbonyl oxygen, T represents H, and W is as defined above excluding halogen, a compound of formula II may be reacted with a base such as aqueous NaOH, etc:

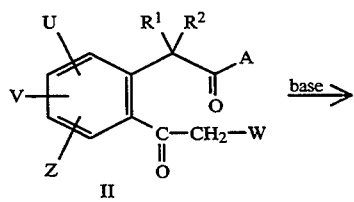

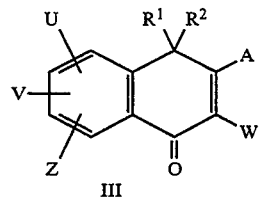

This reaction can be performed at any suitable temperature depending upon the base (e.g., with NaOH elevated temperature of from about 50° C. to about 70° C. may be employed) and may be run in an inert solvent such as tetrahydrofuran (THF).

The compounds of III may be converted to other compounds of formula I (e.g., compounds of formulas IV, IVa, Va, VI, VII, IX, X and XI below) by various techniques as illustrated below. For example, a compound of formula III may be hydrogenated to prepare a compound of formula IV:

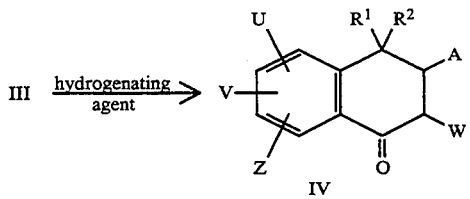

This reaction may be performed under conventional conditions for hydrogenation of olefinic double bond, e.g., by hydrogenation with palladium on activated carbon as a catalyst.

If W in formula IV is H, the groups $W^1$ and $W^2$ can be introduced as described below. For example, a compound of formula IVa may be reacted with a compound of the formula $W^1L^1$ and base to prepare a compound of formula Va:

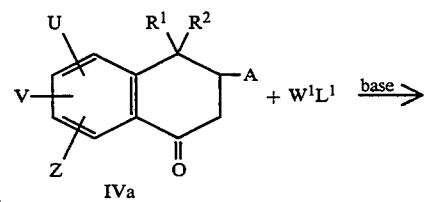

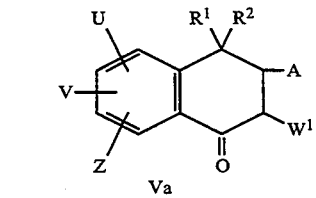

wherein $L^1$ is a leaving group such as chloro, bromo or iodo, and $W^1$ represents alkyl, halo, —(CO)$R^6$, CH$_2$Q, (CO)OR$^6$ or —CH$_2$OR$^5$. This reaction can be performed with a base such as NaH or lithium diisopropylamide in THF.

A compound of formula IVa may also be reacted with lead tetraacetate to produce a compound of formula VI which may be hydrolyzed and then reacted with a compound $R^5L^2$ or $QCH_2L^2$ or $R^6OOC(CH_2)_n$—$L^2$.

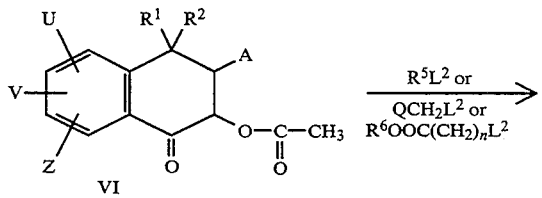

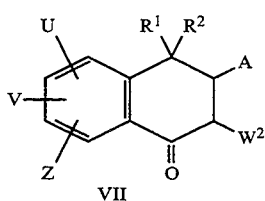

wherein $W^2$ represents $OR^5$, $O(CH_2)_nQ$, $O(CH_2)_nCOOR^6$ or $O(CO)R^6$ and $L^2$ represents a leaving group such as bromo or iodo.

To prepare a compound of the invention of formula IX, a compound of formula IV is reacted with a compound $TL^3$ in the presence of base:

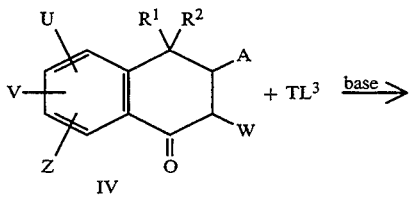

wherein $L^3$ is a leaving group such as bromo or iodo.

The compound of formula IX may be hydrogenated to form a compound of the invention of formula X:

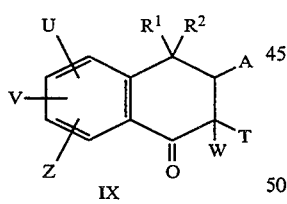

The compound of formula IX may also be reacted with a compound of the formula $R^3M$ to prepare a compound of formula XI:

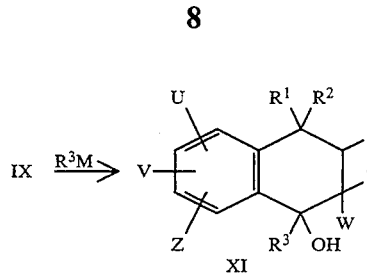

wherein M represents a metal or metal salt such as Li, MgBr, TiCl₃ (when $R^3=CH_3$), NaBH₄ (when $R^3=H$), etc.

The compounds of formula II may be prepared from known materials. For example, a compound of formula XII may be reacted with a halogenating agent such as SOCl₂ or (COCl)₂ to form the corresponding acid halide of formula XIII which is then reacted with a compound $A_2$—$M^a$ wherein $M^a$ represents copper cadmium, etc., or alternatively with the compound "AH" in the presence of a Lewis acid, e.g., AlCl₃, to produce a compound of formula XIV:

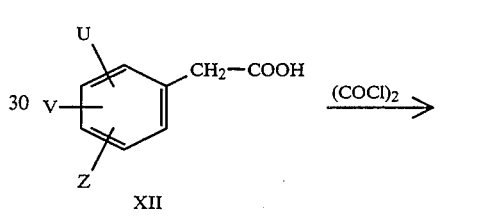

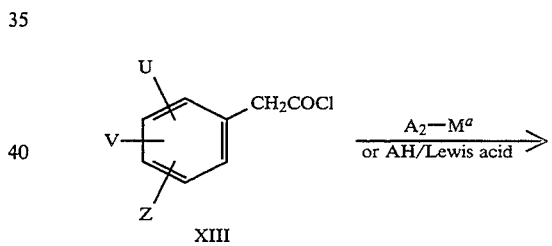

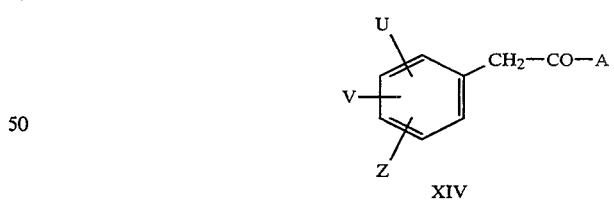

Compounds of formula XIV can be alternatively prepared by reacting a compound of formula 2A with a compound of formula 2B in the presence of base, such as NaH, in an organic polar solvent, such as DMF. Compounds 2A can be prepared by following the literature procedure, see Tetrahedron, 31, 1219 (1975). If it is desired that $R^1$ and/or $R^2$ represent alkyl, —CH₂—alkenyl or —CH₂—alkynyl groups, they can be introduced into the compounds of formula XIV by reaction in succession with compounds of the formulas $R^{1a}L^4$, and $R^{2a}L^4$ in the presence of base such as NaH or lithium diisopropylamide:

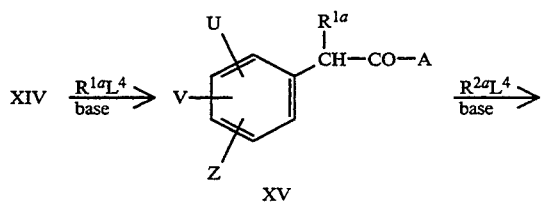

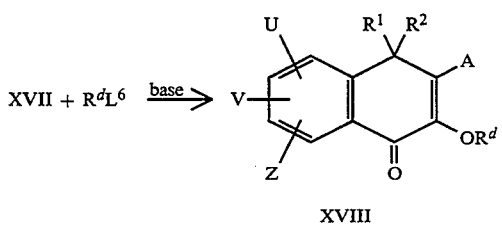

wherein $R^d$ represents $R^{5a}$ or $CH_2Q$ and $L^6$ represents a leaving group such as bromo or iodo:

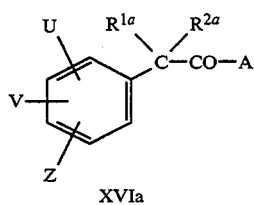

B. A compound of formula XIX may be reacted with a-strong acid such as polyphosphoric acid to form a compound of formula IVa:

wherein $L^4$ represents a leaving group such as bromo or iodo and $R^{1a}$ and $R^{2a}$ each independently represent alkyl, —$CH_2$—alkenyl or —$CH_2$—alkynyl groups. The order of the reactions with $R^{1a}L^4$ and $R^{2a}L^3$ may be reversed.

The —$CH_2$—alkenyl groups described above may be converted to alkenyl ($R^1$ or $R^2$) groups having the carbon—carbon double bond alpha relative to the carbon atom to which such groups are attached by treatment with iron carbonyl, e.g., $Fe(CO)_5$.

The compound of formula XVI may be reacted with a compound of the formula $L^4(CO)CH_2W$ in the presence of a Lewis acid to produce a compound of formula II:

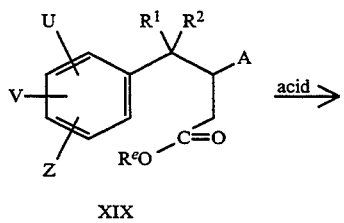

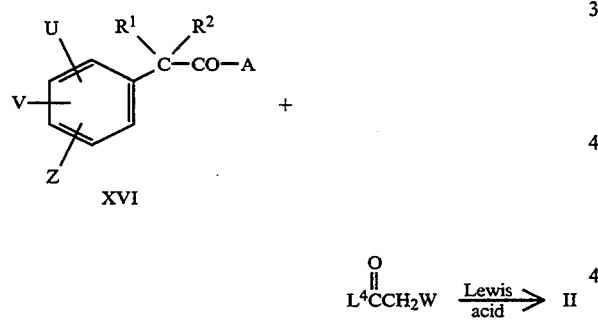

wherein $L^4$ is a leaving group such as chloro.

As an alternative method for making compounds of formula III wherein W represents $OR^5$ or $OCH_2Q$, a compound of formula IVa may be reacted with isoamylnitrile in ethanol and HCl to produce a compound of formula XVII:

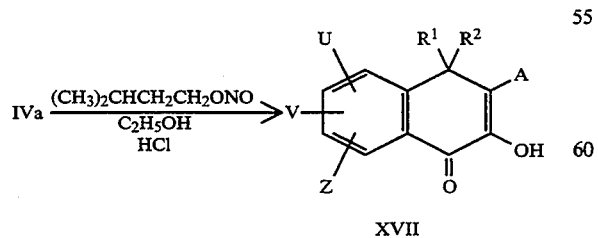

If it is desired that W represent $OR^{5a}$ (wherein $R^{5a}$ represents $R^5$ other than H) or $OCH_2Q$, the compound of formula XVII is reacted with a compound of the formula $R^dL^6$ in the presence of a base such as NaH,

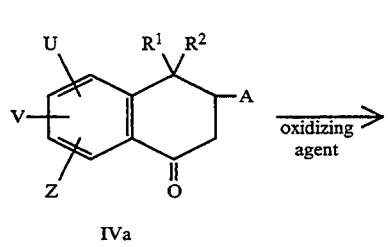

wherein $R^e$ represents an alkyl group such as methyl or ethyl. The compound of formula IVa may then be treated as discussed above to produce other compounds within the scope of formula I.

Compound IVa can be converted to compound IIIa by treatment with an appropriate oxidizing agent such as 2,3-dichloro-5,6-dicyano-1,4-benzoquinone (DDQ):

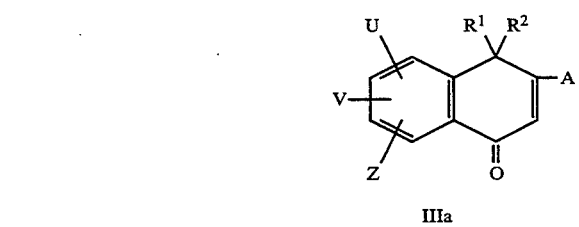

This reaction may be performed at about room temperature, using an appropriate solvent., e.g., $CH_2Cl_2$ or THF.

The compounds of formula XIX may be prepared by reducing a compound of formula XX to the corresponding aldehyde, e.g., by reaction with lithium aluminum hydride and then with an oxidizing agent such as pyridium dichromate:

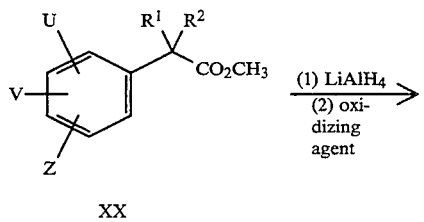

The aldehyde XXa is then reacted with $$(C_2H_5O)_2\overset{\overset{O}{\|}}{P}-CH_2-\overset{\overset{O}{\|}}{C}-OR^e$$

in the presence of a base such as NaH to form a compound of formula XXI, which is then reacted with a compound of the formula ALi in the presence of CuI and $BF_3$ to form a compound of formula XIX:

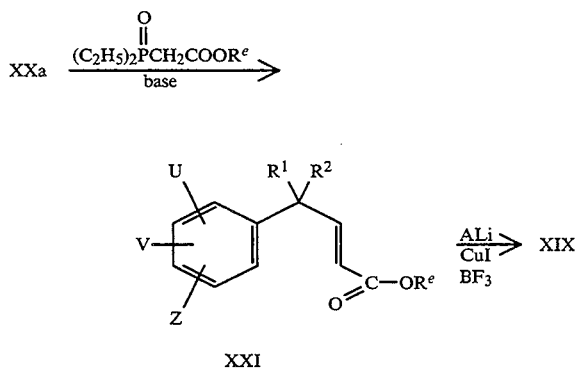

The last reaction may be performed at low temperature, e.g., from about −78° C. to about 0° C. in an inert solvent such as THF.

Alternatively, the aldehyde of formula XXa can be prepared by reacting the alcohol of formula XXII with a compound $HL^6$ such as HBr, HCl, etc., to form a compound of formula XXIII, which is then reacted with Li in the presence of dimethylformamide (DMF):

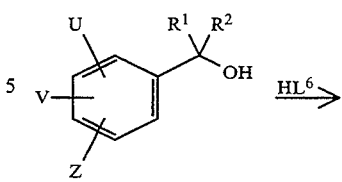

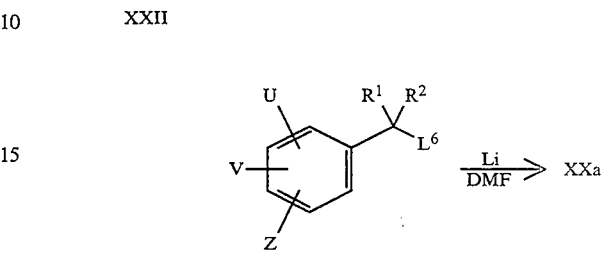

wherein $R^{2a}$ is alkyl and $L^6$ is a leaving group such as chloro, bromo, etc.

A compound of formula XIX may alternatively be prepared by reacting a compound of formula XXIII with a compound of formula XXIV and Li dispersed in THF:

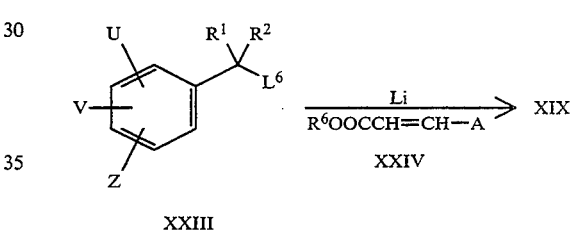

wherein $L^6$ is as defined above.

C. A compound of formula XXV may be reacted with a strong acid such as trifluoroacetic acid to form a compound of formula XXVI:

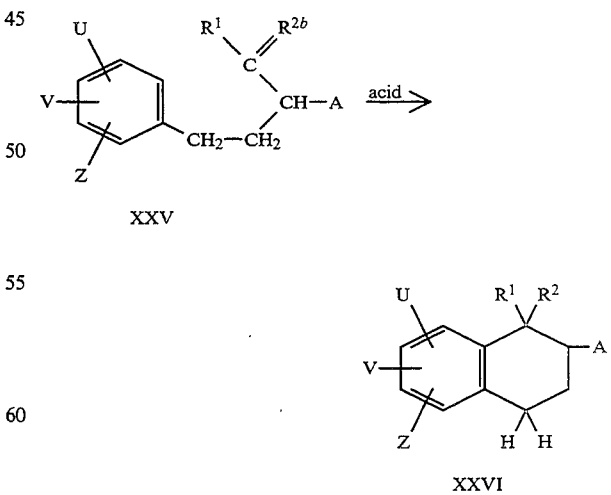

wherein $R^{2b}$ represents the precursor of the group $R^2$.

The compound of formula XXVI may be oxidized to the corresponding keto compound of formula IVa, e.g., by reaction with chromic anhydride or DDQ.

XXVI $\xrightarrow{\text{oxidizing agent}}$ 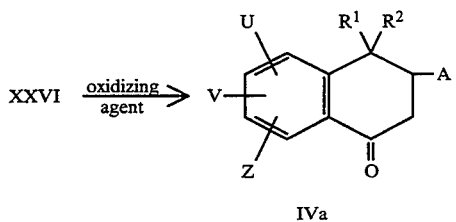
IVa

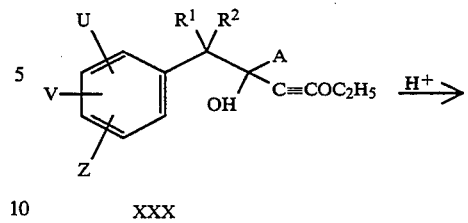
XXX

The keto compound of formula IVa may be substituted with W, T and other $R^3$ and $R^4$ groups as described above.

The compounds of formula XXV may be prepared by reacting a compound of the formula XXVII with a compound H—(CO)—A in the presence of base to form a compound of formula XXVIII, which is then reacted with a compound XXIX where M represents, e.g., Li or MgBr, in the presence of a copper halide or copper cyanide to give a compound of formula XXIV, which is reduced, for example, by hydrazine in the presence of base at elevated temperature, e.g., about 130°-170° C., to generate the compound of formula XXV where =CH—$R^{2a}$ represents =$R^{2b}$:

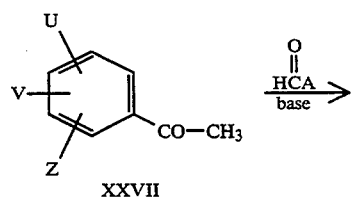
XXVII

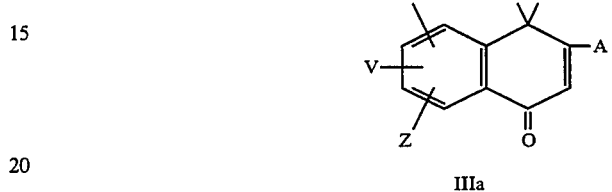
IIIa

The compound of formula IIIa may then be hydrogenated to produce a compound of formula IVa which may then be reacted to provide appropriate other W, T, $R^3$ and $R^4$ substituents as described above.

A compound of formula XXX may be prepared by reacting a compound of formula XVI above with BrMg—C≡C—OC$_2$H$_5$:

XVI+BrMg—C≡C—OC$_2$H$_5$→XXX

E. A compound of formula IVa may be prepared by reacting a compound of the formula XXXI with $A_2$—M in the presence of Ni(acac)$_2$ wherein acac is acetylacetonate:

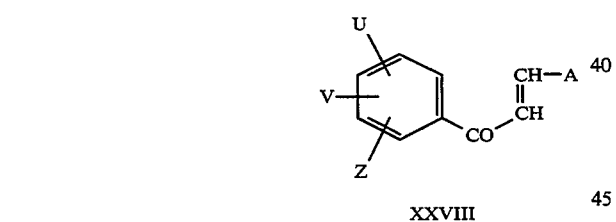
XXVIII

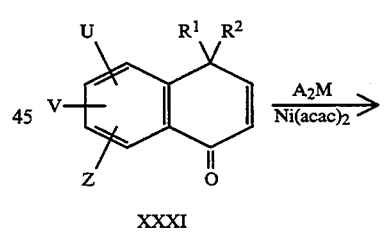
XXXI

XXVIII $\xrightarrow{\text{(XXIX)}{\text{CuX}}}$ where XXIX is $R^1$—C—M with CH=$R^{2a}$

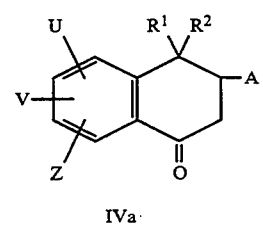
IVa

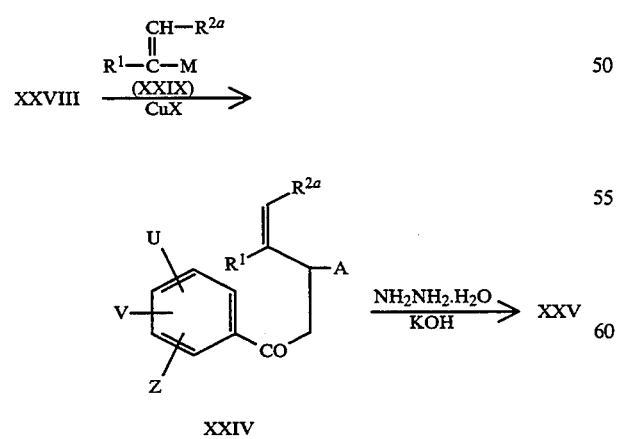
XXIV
$\xrightarrow{\text{NH}_2\text{NH}_2.\text{H}_2\text{O}}{\text{KOH}}$ XXV wherein M is a metal such as Zn.

The compound of formula XXXI may be prepared by reacting a compound of formula XXa above with BrMgC≡C—OC$_2$H$_5$ to produce a compound of formula XXXII which is then treated with strong acid such as trifluoroacetic acid to provide XXXI.

D. A compound of formula IIIa may be prepared by reacting a compound of the formula XXX with a strong acid:

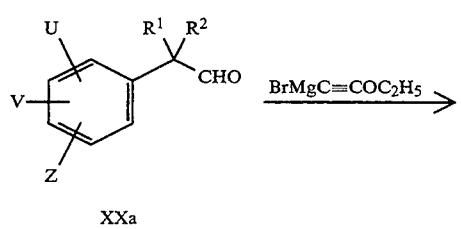 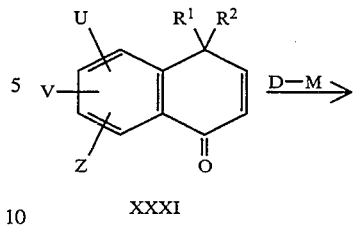

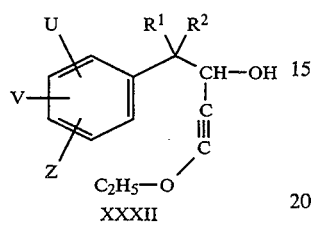

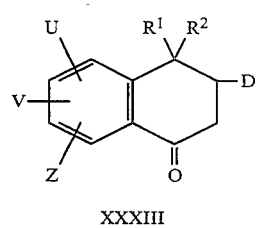

wherein D represents alkyl, $SR^5$ or $$-\overset{\overset{O}{\|}}{C}-R^5$$

while M is Zn, Li or Ni, respectively.

G. Alternatively, a compound of formula XXXIV may be prepared by a compound of formula XXXV with $D_2$—M in the presence of $Ni(acac)_2$ when D is alkyl or with DM when D is $(CO)R^5$:

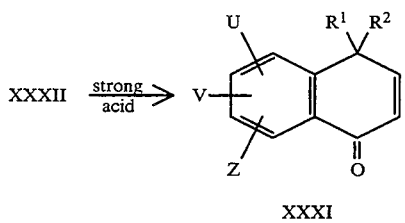

F. To prepare compounds of formula Ib, a compound of formula XXXIII is reacted with base and a compound of the formula $L^7A$ to produce a compound of formula XXXIV. The base is a hindered strong base such as Lithium cyclohexyisopropylamide, and $L^7$ is a leaving group such as bromo or iodo. Compounds of formula Ib may also be prepared from a compound of formula XXXIII with a base and $L^7A$ in the presence of $Ni(COD)_2$ wherein COD is cyclooctadiene.

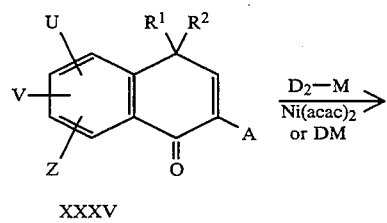

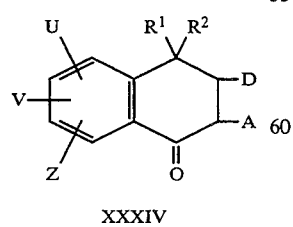

The compounds of formula XXXIII may be prepared by reacting a compound of formula XXXI above with D—M:

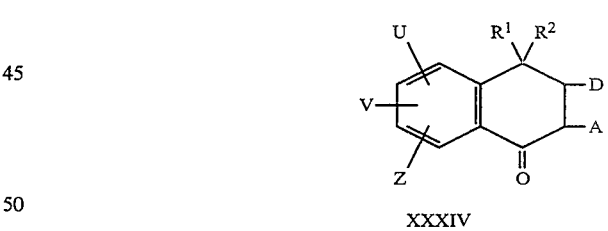

wherein M is Zn and Ni, respectively.

To prepare a compound of formula XXXV, a compound of formula XXa above may be reacted with a compound of XXXVI to produce XXXVII, which under basic conditions may convert to a compound of formula XXXV:

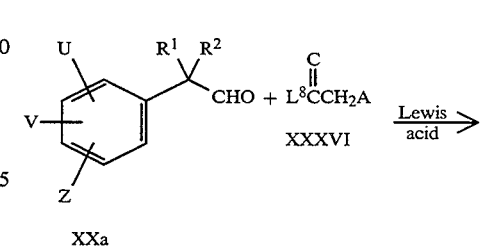

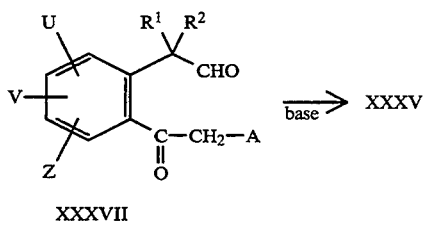

XXXVII wherein $L^8$ is a leaving group such as chloro.

Alternatively, a compound of formula XXV can be prepared by oxidation of a compound of formula XXXIVa, for example use DDQ (dichlorodicyanoquinone) as oxidizing agent.

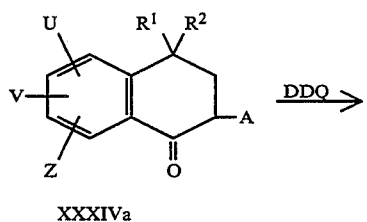

XXXIVa

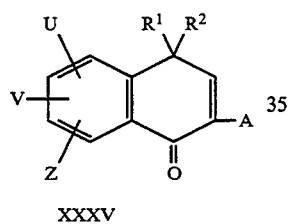

XXXV

Compounds of formula XXXIVa can be prepared from XXXIIIa by literature procedure (JACS, 93 3658 (1971)). XXXIIIa in term can be prepared from XXXI by simple hydrogenation.

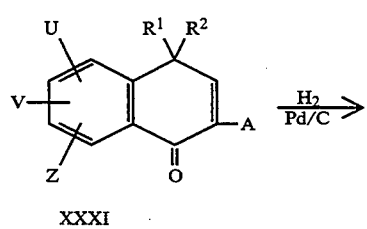

XXXI

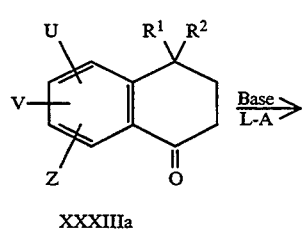

XXXIIIa

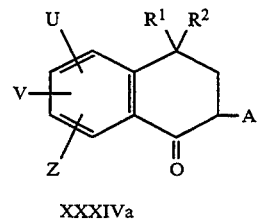

XXXIVa where L is a leaving group such as bromo or iodo.

H. To prepare compounds of formula XXXVIII wherein $R^3$ and $R^4$ together represent =N—OR$^6$, =N—N(R$^6$)$_2$, =N—NH(CO)R$^6$, =N—NH(SO$_2$)R$^6$ or =N—NH(CO)NH$_2$, a compound of formula IX is reacted with an appropriate compound of the formula NH$_2$—MM, where MM is OR$^6$, —N(R$^6$)$_2$, —NH(CO)R$^6$, —NH(SO$_2$)R$^6$ or —NH(CO)NH$_2$, by conventional techniques e.g., reflux in ethanol or 1-butanol.

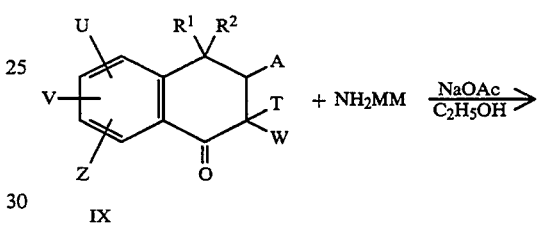

IX

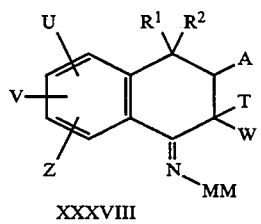

XXXVIII

Alternatively compounds of formula XXXVIIIa, where MM=OH may be prepared by reaction of compounds of formula XXXIX with a strong base and TL. The strong base, for example, is n—butyl lithium. L is a leaving group such as chloro, bromo or iodo.

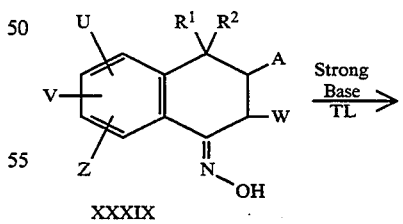

XXXIX

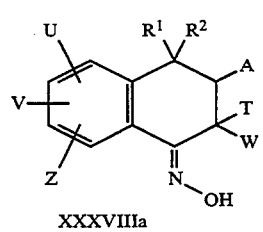

XXXVIIIa

A compound of formula XXXIX may be prepared by reacting a compound of formula XXXXII with a strong base and WL.

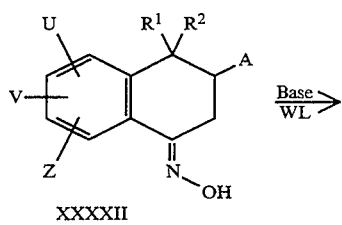

XXXXII

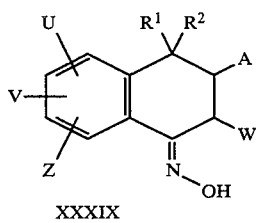

XXXIX where L is a leaving group such as chloro, bromo or iodo.

To prepare compounds wherein $R^3$ and $R^4$ together represent $=N-O(CO)R^6$, XXXXIII, a compound of formula XXXVIIIa may be reacted with $R^6(CO)L$ in the presence of base.

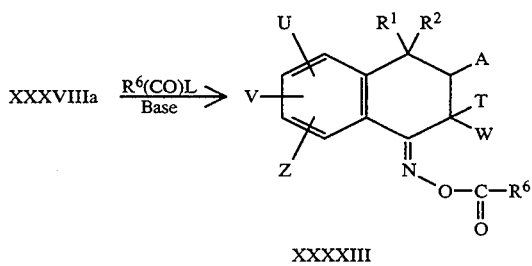

XXXXIII where L is a leaving group, such as chloro.

To prepare compounds wherein $R_3$ is H and $R^4$ are $NH(CO)R^6$, XXXXVI, a compound of formula XXXXII may be reacted with $R^6(CO)Cl$ in the presence of base. Compound XXXXIV in turn can be prepared from XXXXV by $NaBH_4$ reduction in the presence of Lewis acid, for example $TiCl_4$.

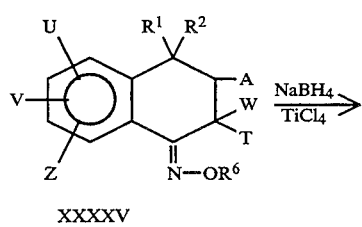

XXXXV

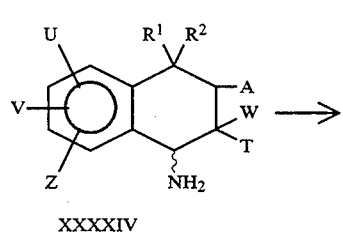

XXXXIV

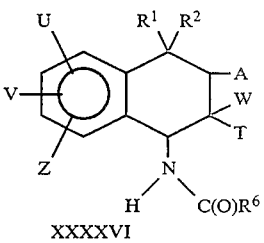

XXXXVI

Compounds of formula Ib wherein $R^3$ and $R^4$ represent substituents other than carbonyl can be prepared from a compound of formula XXXIV in the same manner as described above in section A with regard to compounds of formula Ia.

The compounds of formula Ic, Id and Ie can be prepared by the processes described below. In these processes substituents $R^1$, $R^2$, $R^5$, $R^6$, $R^7$, $R^8$, $R^9$, $R^{10}$, $R^{11}$, A, M, N, T, U, V, Z and W are as defined above unless otherwise indicated.

To prepare the compounds of formula Ic wherein M is oxygen and $R^{10}$ and $R^{11}$ together represent a carbonyl oxygen, a compound of formula IVa may be reacted with a oxidizing agent such as meta-chloroperbenzoic acid or hydrogen peroxide in acetic acid

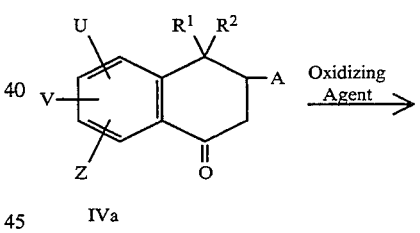

IVa

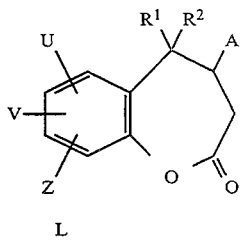

L

This reaction can be performed at any suitable temperature from $-10°$ to room temperature and may be run in an inert solvent such as methylene chloride.

The compounds of formula L may be converted to other compounds of Ic by various procedures as illustrated below. For example, a compound of formula L may be reacted with a compound of the formula WL and base to prepare a compound of formula:

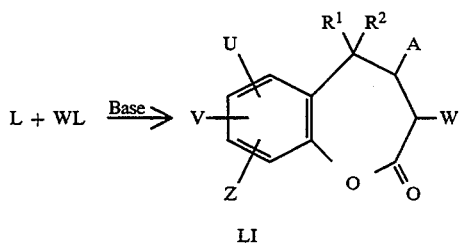

LI wherein L is a leaving group such as chloro, bromo or -iodo, and W represents alkyl, halo, —(CO)R⁶ or —CH$_2$OR⁵. This reaction can be performed with a base such as sodium hydride or lithium diisopropylamide in an appropriate solvent, such as tetrahydrofuran.

To prepare a compound of the invention of formula LII a compound of formula LI is reacted with a compound, TL, in the presence of base, such as sodium hydride, potassium hydride, lithium diisopropylamide:

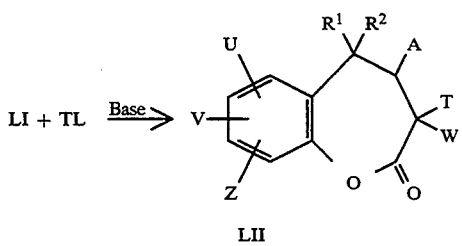

LII wherein L is a leaving group such as chloro, bromo or iodo.

To prepare a compound of the formula LIII, a compound of formula L is reacted with cyclopentadienyl titanium:

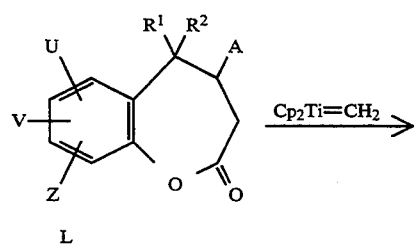

L

This reaction can be performed at any suitable temperature, such as 0° C. to room temperature, in an organic solvent, e.g., methylene chloride or THF (see JACS, 102, 3270 (1980).

The compound of formula LIII may hydrogenated to form the compound of formula LIV:

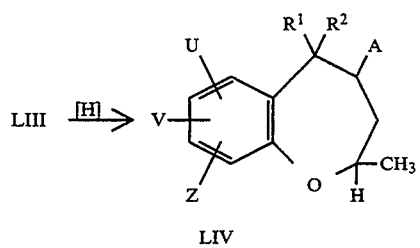

LIV

The sulfur compound of the formula LV may be prepared by reacting a compound of formula LIV with phosphorous pentasulfide:

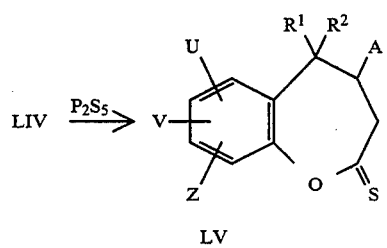

LV

This reaction can be performed in an organic solvent, such as toluene, at the boiling point of the solvent.

To prepare the compound of formula Ic wherein M is oxygen and R¹⁰ and R¹¹ are both H, a compound of formula L is reacted with a reducing agent, e.g. lithium aluminum hydride, to afford a compound of formula LVI:

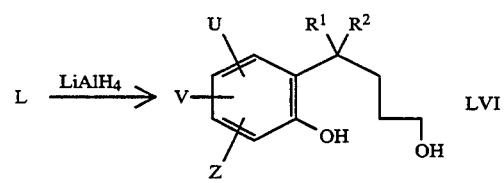

This compound is cyclized by reaction with diethyl azodicarboxylate and triphenyl phosphine in an appropriate solvent, THF, at room temperature:

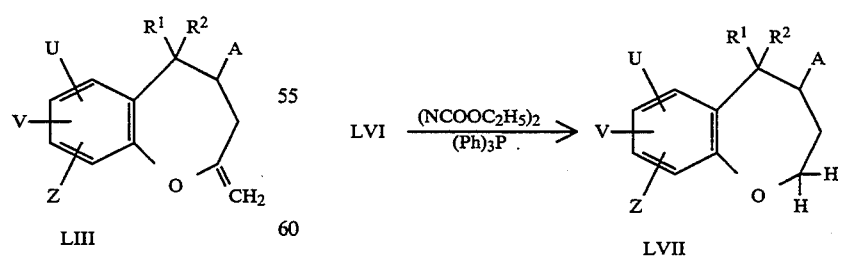

LVII

To prepare compounds of formula Ic where M is —NH— and R¹⁰ and R¹¹ together represent a carbonyl oxygen, a compound of the formula LVIII may be reacted with methanesulfonyl chloride in pyridine to form the compound of a LIX:

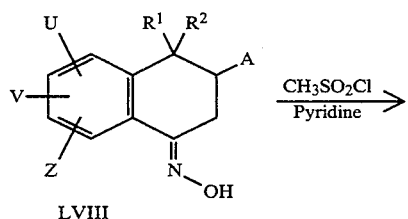

LVIII

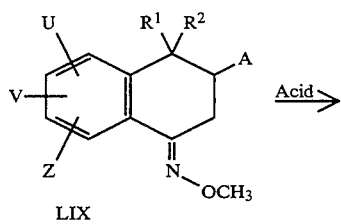

LIX

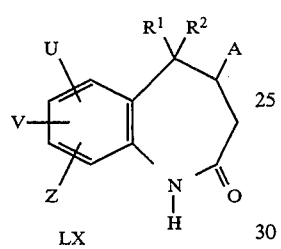

LX

The compound of formula LIX may then be rearranged to a compound of formula LX by treatment under acidic conditions, for example aqueous hydrochloric acid in an organic solvent such as tetrahydrofuran, or passing the compound of formula LIX over silica gel.

The sulfur compound of formula LXI may be prepared by reacting a compound of formula LX with phosphorous pentasulfide

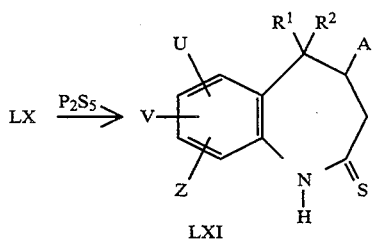

LXI

To prepare a compound of formula Ic wherein M is —CH$_2$— and R$^{10}$ and R$^{11}$ together represent a carbonyl oxygen, a compound of the formula IVa may be reacted with trimethylsilyl diazomethane in the presence of boron trifluoride to afford:

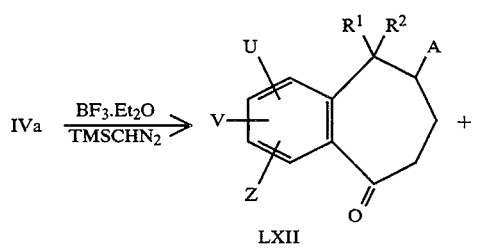

LXII

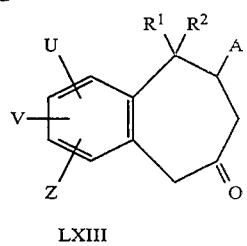

LXIII

The reaction can be performed at a suitable temperature, e.g. between −78° C. to 0° C., and may be run in an inert solvent such as methylene chloride. The compounds of formula LXII and LXIII may be isolated by conventional techniques, such as chromatography.

To prepare a compound of Ic wherein M is CR$^7$R$^8$, R$^{10}$, and R$^{11}$ together represent a carbonyl oxygen, a compound of the formula LXIII is reacted with a compound R$^7$L and a base, e.g. sodium hydride or lithium diisopropylamide:

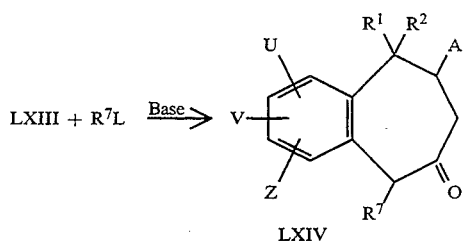

LXIV where L is a leaving group such as brome or iodo.

Reaction of a compound of formula LXIV with a compound R$^8$L in the presence of base as above affords the compound of formula LXV

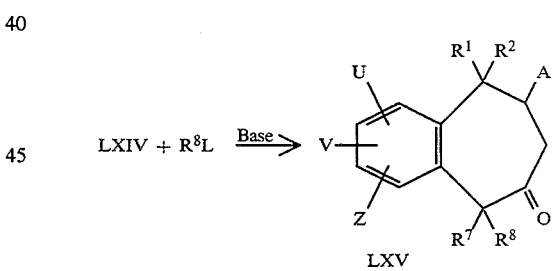

LXV

To prepare compounds of the formula Ic wherein M is —NH— and R$^{10}$ and R$^{11}$ are both hydrogen, a compound of the formula LIX may be reacted with a reducing agent, such as diisopropylaluminum hydride and lithium aluminum hydride, in an inert organic solvent, for example toluene

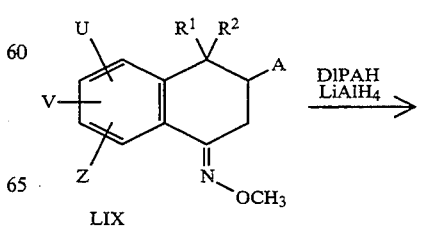

LIX

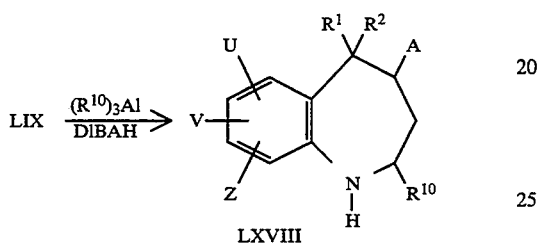

LXVII

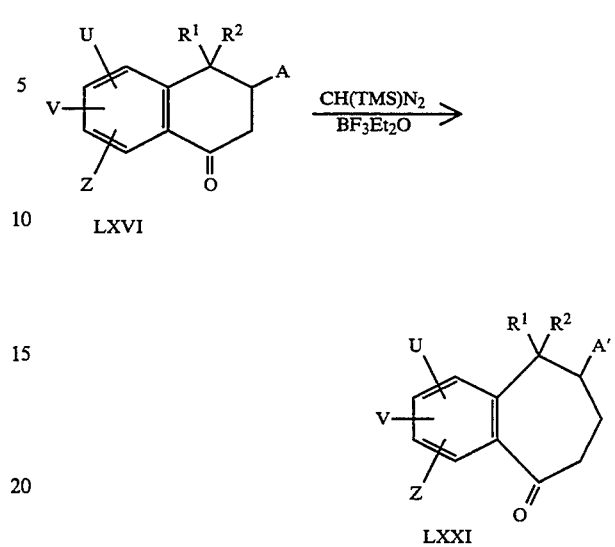

LXVI → (CH(TMS)N₂ / BF₃Et₂O)

To prepare compounds of formula Ic wherein M is —NH— and $R^{10}$ is alkyl, a compound of formula LIX may be reacted with $(R^{13})_3Al$ and diisobutylaluminum hydride:

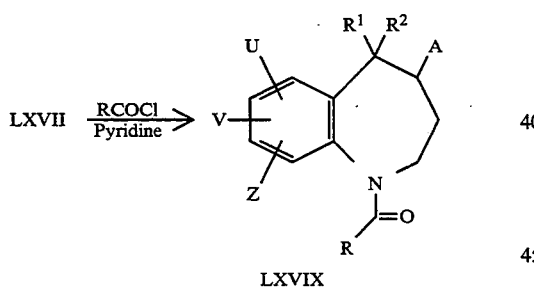

LIX (R¹⁰)₃Al / DIBAH → LXVIII

This reaction may be performed in a inert organic solvent, such as toluene or methylene chloride.

To prepare a compound of the formula LXVIX, a compound of the formula LXVII may be reacted with an acid chloride in pyridine at a temperature of from about 0° C. to room temperature:

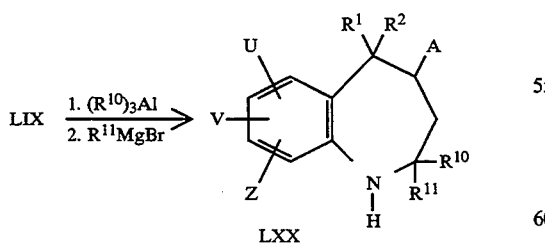

LXVII RCOCl/Pyridine → LXVIX

To prepare compounds of formula Ic where M is —NH— and $R^{10}$ and $R^{14}$ are alkyl, allyl, a compound of formula LXVI is reacted with $(R^{10})_3Al$ and $R^{11}$MgBr:

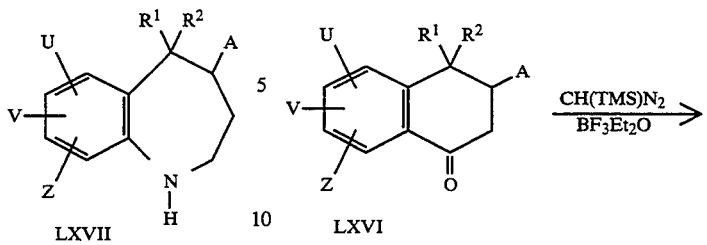

LIX 1. (R¹⁰)₃Al  2. R¹¹MgBr → LXX

References for the ring expansions of methoximer are Pure and Appl. Chem., Vol. 55, No. 11, 1853 (1983) and Angew. Chem. Int. Ed. Eng. 24, 668 (1985).

To prepare a compound of the formula LXXI, a compound of formula LXVI is reacted with trimethylsilyl diazomethane in the presence of borontrifluoride

LXXI

This reaction may be performed in methylene chloride at low temperature, such as −78° C.

The compound of formula LXXI may be reacted with a compound of formula WL and base, such as sodium hydride, potassium hydride, to prepare a compound of formula LXXII:

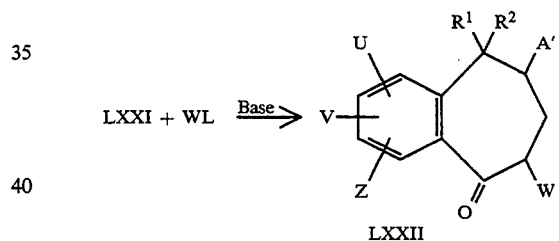

LXXI + WL Base→ LXXII where L is a leaving group such as chloro, bromo or iodo.

The compound of formula LXXII may be further reacted with a compound TL in the presence of base to prepare a compound of formula LXXIV:

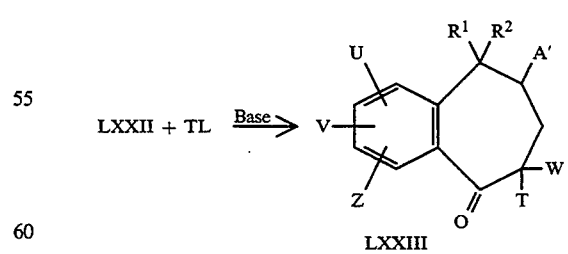

LXXII + TL Base→ LXXIII where L is a leaving group as noted above.

Compound LXXII can be converted to compound LXXIV by treatment with an appropriate oxidizing agent such as 2,3-dichloro-5,6-dicyano-1,4-benzoquinone (DDQ):

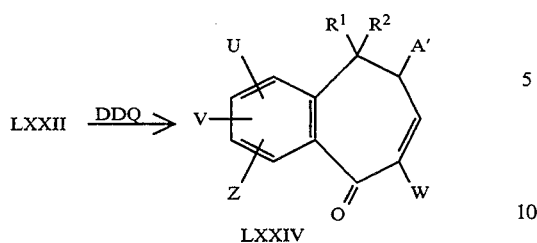

LXXII $\xrightarrow{\text{DDQ}}$ LXXIV

To prepare compounds of the formula LXXV wherein $R^{10}$ and $R^{11}$ together represent $=N-OR^6$, $=N-N(R^6)_2$, $=N-NH(CO)R^6$, $=N-NH(SO_2)R^6$ or $=N-NH(CO)NH_2$, a compound of formula LXXIII is reacted with an appropriate compound of the formula $N_2-MM$, where MM is $OR^6$, $-N(R^6)_2$, $-NH(CO)R^6$, $-NH(SO^2)R^6$ or $-NH(CO)NH_2$, by conventional techniques, e.g. reflux in ethanol or 1-butanol:

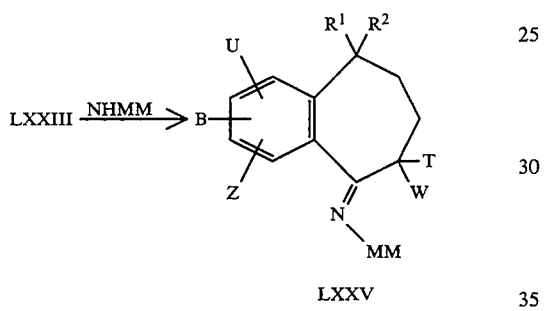

LXXIII $\xrightarrow{\text{NHMM}}$ LXXV

To prepare a compound of formula LXXVII, a compound of the formula LXXVI is reacted with trimethylsilyl-chloride in the presence of a base, such as potassium hydride:

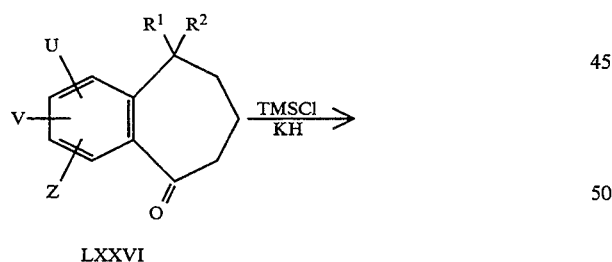

LXXVI $\xrightarrow[\text{KH}]{\text{TMSCl}}$ LXXVII

This compound of formula LXXVII is reacted with palladium acetate and 1,4-benzoquinone in acetonitrile to afford the compound of formula LXXVIII:

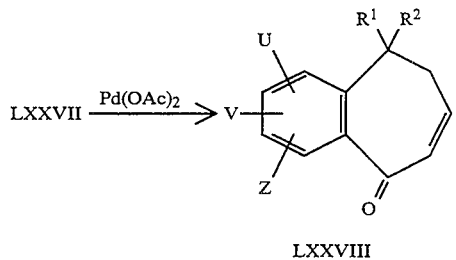

LXXVII $\xrightarrow{\text{Pd(OAc)}_2}$ LXXVIII

The compound of formula LXXIX is prepared by reacting a compound of formula LXXVIII with a compound A—Met wherein Met is Li or MgBr in the presence of CuCN or CuI:

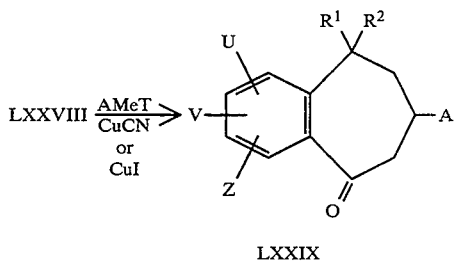

LXXVIII $\xrightarrow[\text{or CuI}]{\text{AMeT} / \text{CuCN}}$ LXXIX

To prepare compounds of the invention of formula Ic or Id wherein $R^{10}$ and $R^{11}$ together represent $=N-OR^6$, $=N-N(R^6)_2$, $=N-NH(CO)R^6$, $=N-NH(SO_2)R^6$ or $=N-NH(CO)NH_2$. a compound of the formula Ic or Id wherein $R^{10}$ and $R^{11}$ together represent a carbonyl oxygen is reacted with an appropriate compound of the formula $NH_2-MM$, where MM is $OR^6$, $-N(R^6)_2$, $-NH(CO)R^6$, $-NH(CO)NH_2$, by conventional techniques, e.g. reflux in ethanol or 1-butanol

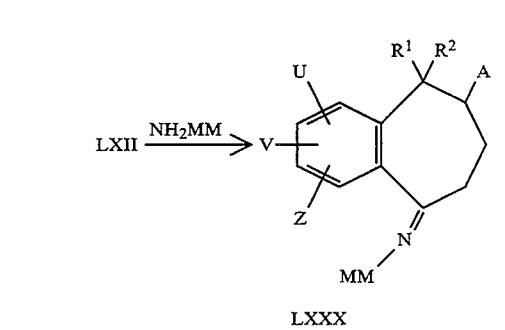

LXII $\xrightarrow{\text{NH}_2\text{MM}}$ LXXX

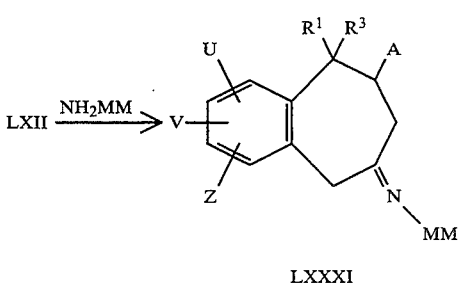

LXII $\xrightarrow{\text{NH}_2\text{MM}}$ LXXXI

To prepare compounds of the invention Ic, where the dotted line represents a double bond, a compound of formula LXII is reacted with $R^8$Met in the presence of CeCl₃ to give a compound of formula LXXXII, where R⁸ is alkyl, alkenyl, alkynyl, Q or —CH₂Q and Met is Li or MgBr:

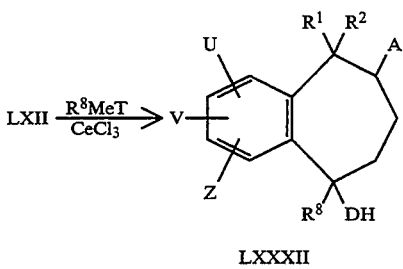

LXXXII

The compound of formula LXXXII can be reacted with pyridine and POCl₃ in an organic solvent, e.g. benzene at a temperature of 0° C. to room temperature to give a compound LXXXIII:

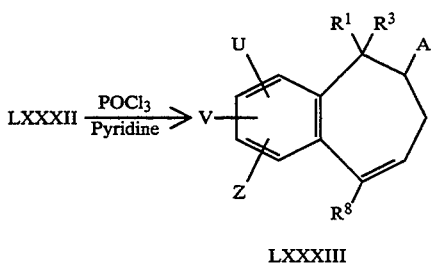

LXXXIII

In the above processes, it is many times desirable and/or necessary to protect certain groups from reaction, e.g., the groups in column 1 of the following table. Conventional protecting groups are operable. Preferred protecting groups appear in column 2 of the table.

| 1. Group to be Protected | 2. Protected Group |
|---|---|
| —COOH | —COOalkyl, —COObenzyl, —COOphenyl, [cyclic orthoester with CH₃] |
| \>NH | \>N—CO₂alkyl, \>N—CO₂benzyl, \>N—CO₂CH₂CCl₃ |
| \>CO | [cyclic acetals: O-C-O, O-C-O, S-C-S] |
| —OH | —O-[tetrahydropyranyl]-OCH₃, —OCH₂OCH₂CH₂OCH₃ |

| 1. Group to be Protected | 2. Protected Group |
|---|---|
| —NH₂ | [succinimide N-] |

Of course other protecting groups well known in the art may be used. After the reaction or reactions, the protecting groups may be removed by standard procedures well known in the art.

The compounds of formula Ia and Ib may also be converted to other compounds of the invention by methods conventional in the art. For example, certain U, V and/or Z substituents may be changed to other U, V and/or Z substituents within the scope of the invention. In one such method, a U, V or Z OH group may be converted to a —O(CH₂)ₙQ group by treatment with a compound $L^9$—(CH₂)ₙQ group in the presence of base wherein $L^9$ is a leaving group such as bromo or iodo. Also, a compound of formula Ia or Ib wherein W and D represent OH may be converted to acetyloxy groups by treatment with acetic anhydride.

The compounds of this invention can be used to treat allergies and a preferred use is for treating allergic chronic obstructive lung diseases. Chronic obstructive lung disease as used herein means disease conditions in which the passage of air into and out of the lungs is obstructed or diminished such as is the case in asthma, bronchitis and the like.

The anti-allergy method of this invention is identified by tests which measure a compound's inhibition of leukotriene release in sensitized guinea pigs. Sensitized guinea pigs are killed by a blow to the head and the lungs removed and cleaned of visible connective tissue, trachea and large blood vessels. The lungs from individual animals are sliced into fragments approximately 1 mm in thickness using a McIlwain tissue chopper and then washed with oxygenated Tyrode's buffer. Weighed aliquots (approximately 400 mg wet weight) of lung are transferred into vials containing 2 ml of fresh Tyrode's solution (containing 10 mM cysteine) and incubated in the presence or absence of test compound for 12 min at 37° C. The tissues are then challenged with 20 μg ovalbumin/ml (final concentration) and incubated for 15 min. To measure leukotriene release, an aliquot of supernatant fluid is extracted with 4 volumes of 100% ethanol. After removal of the precipitated protein, the clear fluid is dried under a stream of N₂ gas. The leukotriene content is measured by a radioimmunoassay using [³H]LTC₄ and antiserum obtained from New England Nuclear. The cross-reactivity of the antiserum for LTD₄ is 55%. Percent inhibition of lekotriene release is calculated by comparing for each lung the release in the presence of the test compound to that in the absence of test compound. Representative compounds of the invention at a relative dose of 50 μM of tissue are found to inhibit leukotriene release in the test procedure as indicated below in Table 1:

TABLE 1

Inhibition of SRS-A Release from Antigen-Challenged, Sensitized Guinea Pig Lung

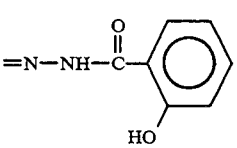

| $R^3/R^4$ | E | G | J | P | L | equals double bond | Dose μm | % Inhibition |
|---|---|---|---|---|---|---|---|---|
| =O | OCH₃ | OCH₃ | H | OCH₃ | OCH₃ | yes | 50 | 55 |
| =O | OH | OH | H | OH | H | yes | 50 | 77 |
| =O | OCH₃ | OCH₃ | OH | OCH₃ | OCH₃ | yes | 50 | 24 |
| =O | OH | OH | OH | OH | OH | yes | 50 | 81 |
| =O | OCH₃ | OCH₃ | H | OCH₃ | OCH₃ | no | 50 | 62 |
| =O | OH | OH | H | OH | OH | no | 50 | 67 |
| =O | OH | OH | H | OH | OCH₃ | yes | 50 | 43 |
| =O | OCH₃ | OCH₃ | H | OH | OCH₃ | yes | 50 | 10 |
| =O | OCH₃ | OCH₃ | OAc[1,2] | OCH₃ | OCH₃ | no | 50 | 12 |
| =O | OAc[1] | OAc[1] | OAc[1,2] | OAc[1] | OAc[1] | no | 50 | 41 |
| =O | OAc[1] | OAc[1] | H | OAc[1] | OAc[1] | no | 50 | 48 |
| =O | OAc[1] | OAc[1] | OAc[1] | OAc[1] | OAc[1] | no | 50 | 26 |
| =O | OAc[1] | OAc[1] | H | OAc[1] | OAc[1] | yes | 50 | 48 |
| H,H | OCH₃ | OCH₃ | H | OCH₃ | OCH₃ | no | 50 | 5 |

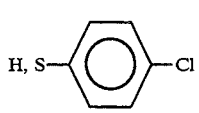

| $R^3/R^4$ | E | G | J | P | K | L | equals double bond | Dose μm | % Inhibition |
|---|---|---|---|---|---|---|---|---|---|
| =O | OCH₃ | OCH₃ | H | OCH₃ | OCH₃ | OCH₃ | no | 10 | 1[4] |
| =O | H | H | H | OCH₃ | H | OCH₃ | no | 10 | 6[4] |
| =N—OH | OCH₃ | OCH₃ | H | OCH₃ | H | OCH₃ | no | 50 | 75 |
| =N—OH | OCH₃ | OCH₃ | H | OCH₃ | H | OCH₃ | no | 10 | 35 |
| =O | OCH₃ | OCH₃ | CH₃ | OCH₃ | H | OCH₃ | yes | 10 | 20 |
| 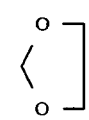 | OCH₃ | OCH₃ | H | OCH₃ | H | OCH₃ | no | 10 | 10 |
| =N—NH(CO)NH₂ | OCH₃ | OCH₃ | H | OCH₃ | H | OCH₃ | no | 10 | 1[4] |
| =N—OH | OCH₃ | OCH₃ | CH₃ | OCH₃ | H | OCH₃ | no | 10 | 13 |
| =N—OH | OCH₃ | OCH₃ | H | OCH₃ | H | OCH₄ | yes | 30 | 0[4] |
| =O | OCH₃ | OCH₃ | CHO | OCH₃ | H | OCH₃ | no | 30 | 19 |
| H,NH(CO)CH₃ | OCH₃ | OCH₃ | H | OCH₃ | H | OCH₃ | no | 30 | 11 |
| H, NH₂ | OCH₃ | OCH₃ | H | OCH₃ | H | OCH₃ | no | 30 | 0[4] |
| H, S-⟨C₆H₄⟩-Cl | OCH₃ | OCH₃ | H | OCH₃ | H | OCH₃ | no | 30 | 14 |
| O-CH₂-O (dioxolane) | OCH₃ | OCH₃ | H | OCH₃ | H | OCH₃ | no | 30 | 23 |
| =N—OCH₃ | OCH₃ | OCH₃ | H | H | H | OCH₃ | no | 30 | 0[4] |
| =O | OCH₃ | OCH₃ | H | H | H | OCH₃ | no | 30 | 28 |
| H,H | OH | OH | H | OH | H | OH | no | 10 | 16 |

[1] AcO = acetyloxy.
[2] AcO trans to 3-(3,4-diacetylboxyphenyl).
[3] AcO cis to 3-(3,4-diacetyloxyphenyl).
[4] Expected to have activity at higher dose.

TABLE 1-continued
Inhibition of SRS-A Release from Antigen-Challenged, Sensitized Guinea Pig Lung

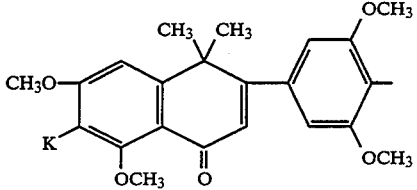

| K | Dose μm | % Inhibition |
|---|---|---|
| H | 30 | 33 |
| OCH$_3$ | 30 | 21 |

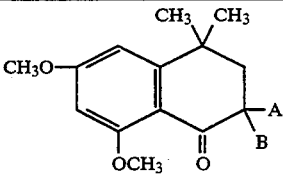

| A | B | Dose | % Inhibition |
|---|---|---|---|
| -CH$_2$-C$_6$H$_4$-OCH$_3$ | H | 30 | 01 |
| -CH$_2$-C$_6$H$_4$-OCH$_3$ | -CH$_2$-C$_6$H$_4$-OCH$_3$ | 30 | 16 |

[1]Expected to have activity at higher dose.

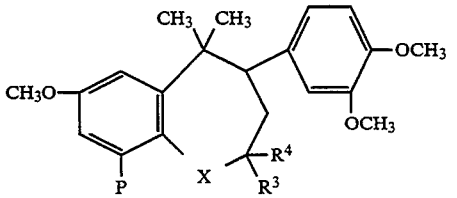

| X | R$^3$/R$^4$ | P | Dose μM | % Inhibition |
|---|---|---|---|---|
| NH | H,H | OCH$_3$ | 30 | 45 |
| NH | H,H | H | 30 | 57 |
| NH | =O | OCH$_3$ | 30 | 65 |
| O | =O | OCH$_3$ | 30 | 59 |
| CH$_2$ | =O | OCH$_3$ | 30 | 47 |
| CH$_2$ | =N—OH | OCH$_3$ | 30 | 46 |

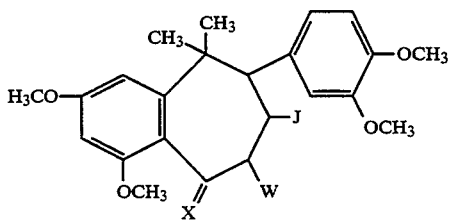

| X | W | J | Dose μM | % Inhibition |
|---|---|---|---|---|
| O | H | H | 30 | 78 |
| N—OH | H | H | 30 | 58 |
| O | CH$_3$ | CH$_3$ | 30 | 25 |
| O | H | CH$_3$ | 30 | 61 |

The anti-allergy method of this invention is identified by tests which measure a compound's inhibition of anaphylactic bronchospams in sensitized guinea pigs having antigen-induced SRS-A mediated bronchoconstriction. Allergic bronchospams was measured in actively sensitized guinea pigs by a modification of the procedure of Konzett and Rossler, *Arch. Exptl. Pathol. Pharmakol.*, 194, pp. 71–74 ( 1940 ). Male Hartley guinea pigs were sensitized with 5 mg ovalbumin injected ip and 5 mg injected sc in 1 ml saline on day 1 and 5 mg ovalbumin injected ip on day 4. The sensitized animals were used 3–4 weeks later. To measure anaphylactic bronchospasm, sensitized guinea pigs were fasted overnight and the following morning were anesthetized with 0.9 ml/kp ip dialurethane. The trachea and jugular vein were cannulated and the animals were ventilated by a Harvard rodent respirator. A side arm to the tracheal cannula was connected to a Harvard pressure transducer to obtain a continuous measure of intratracheal pressure. An increase in intratracheal pressure was taken as a measure of bronchoconstriction. Each guinea pig was injected iv with 1 mg/kg propranolol, 5 mg/kg indomethacin and 2 mg/kg mepyramine given together in a volume of 1 mg/kg. Fifteen minutes later, the animals were challenged with antigen (0.5 per cent ovalbumin) delivered as an aerosol generated from a DeVilbiss Model 65 ultrasonic nebulizer and delivered through the tracheal cannula for 30 seconds. Bronchoconstriction was measured as the peak increase in intratracheal pressure occurring within 15 minutes after antigen challenge. Representative compounds of the invention at a dose of 50 mg/kg were found to inhibit anaphylactic bronchospasms in such test procedure as indicated below in Table 2:

TABLE 2
Inhibition of Anaphylactic Bronchospasms

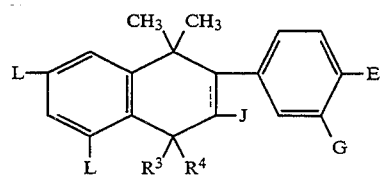

| E | G | P | L | J | $R^3,R^4$ | equals double bond | Dose (mpk)[1] | % Inhibition |
|---|---|---|---|---|---|---|---|---|
| OMe | OMe | OMe | OMe | H | =O | yes | 10 | 36 |
| OH | OH | OH | OH | H | =O | yes | 10 | 17 |
| OH | OH | OH | OH | OH | =O | yes | 10 | 26 |
| OMe | OMe | OMe | OMe | H | =O | no | 10 | 0[2] |
| O(CO)NMe₂ | O(CO)NMe₂ | O(CO)NMe₂ | O(CO)NMe₂ | H | =O | yes | 10 | 10 |
| OAc | OAc | OAc | OAc | H | =O | yes | 10 | 7 |
| OMe | OMe | OMe | OMe | H | =N—OH | no | 10 | 50 |
| OMe | OMe | OMe | OMe | CH₃ | =O | yes | 10 | 24 |
| OMe | OMe | OMe | OMe | H | =N—NH(CO)NH₂ | no | 10 | 20 |
| OMe | OMe | OMe | OMe | H | =N—OH | yes | 10 | 0[2] |
| OMe | OMe | OH | OMe | H | =N—OH | no | 10 | 0[2] |
| OMe | OMe | OM | OMe | H | =N—O(CO)ᵗBu | no | 10 | 20 |
| OMe | OMe | OC₂H₅ | OMe | H | =N—OH | no | 3 | 25 |

Analphylactic Bronchospasm

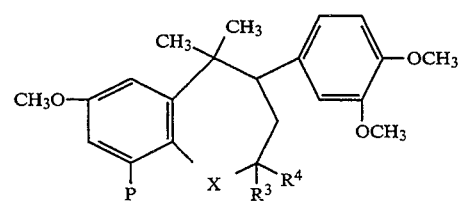

| X | $R^3/R^4$ | P | Dose (mpk)[1] | % Inhibition |
|---|---|---|---|---|
| O | =O | OCH₃ | 10 | 4[2] |
| NH | H,H | OCH₃ | 10 | 34 |
| NH | =O | OCH₃ | 3 | 20 |
| CH₂ | =O | OCH₃ | 10 | 0[2] |
| NH | H,H | H | 10 | 42 |
| CH₂ | =N—OH | OCH₃ | 3 | 0[2] |

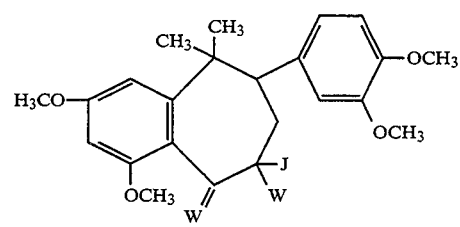

Dose    %

TABLE 2-continued

| X | J | (mpk)[1] | Inhibition |
|---|---|---|---|
| O | H | 10 | 56 |
| N—OH | H | 10 | 10 |
| O | CH₃ | 10 | 53 |

[1] By iv administration.
[2] Expected to have activity at higher dose.

Based on the above test procedure and results, the compounds are effective non-adrenergic, non-anticholinergic, antianaphylactic agents. The compounds may be administered by any conventional mode of administration for treatment of allergic reactions employing an effective amount of a compound of formula I for such mode. For example, when administered orally, appropriate doses are from about 1-100 mg/kg of body weight; when administered parenterally, e.g., intravenously, the compounds may be administered at dosages of from about 0.1-10 mg/kg body weight; when administered by inhalation (aerosol or nebulizer) the compounds may be administered at dosages of from about 0.1-20 mg per puff, one to four puffs may be taken every 4 hours.

The compounds of this invention inhibit 5-lipoxygenase activity, which inhibitory activity has been associated with anti-inflammatory activity. The compounds of the invention are thus useful for the treatment of inflammation, arthritis, bursitis, tendonitis, gout and other inflammatory conditions. The 5-lipoxygenase inhibitory activity of the compounds of the invention may be demonstrated by the procedure described below:

5-Lipoxygenase Assay

The IL-3-dependent murine mast cell clone, MC-9, was used to test the effects of representative compounds of the invention on lipoxygenase activity. The MC-9 cell line was grown in suspension culture (0.4 to 1.2×10⁶ cells/ml) in RPMI 1640 medium (Gibco) with 10% fetal bovine serum (Hyclone) and 2-5% conconavalin-A conditioned supernatant (Musch et. al., (1985) *Prostagandins* 29, 405-4307. Cells were harvested, washed twice by centrifugation, and resuspended in a Ca⁺⁺-free HEPES buffer (25 mM HEPES, 125 mM NaCl, 2.5 mM KCl, 0.7 mM MgCl₂, 0.5 mM EGTA and 10 mM glucose at pH 7.4).

MC-9 cells (0.39 ml at 7.5×10⁶ cells/ml) were preincubated with dimethylsulfoxide (DMSO) vehicle with or without test compound (1 ul) for 4 minutes then incubated for 5 minutes with [¹⁴C] arachidonic acid (Amersham, 59 Ci/mole) at a 9 uM final concentration, and A23187 (Calbiochem) at a 1 uM final concentration was added in 10 ul of water:ethanol (9:1). The reaction was stopped by addition of methanol (0.4 ml), and cellular debris was removed by centrifugation. Aliquots (250 ul) of the incubations were run on a Waters two pump HPLC system fitted with a Waters C18, 10 u 8×100 mm u-Bondapak radial compression column and C18 "Guard Pak". The column was initially eluted at 3 ml/min with water:methanol:acetic acid (67:33:0.08) containing 1 mM EDTA adjusted to pH 6.0 with ammonium hydroxide (Pump A). At 4 minutes, a linear gradient to reach 100% methanol (Pump B) at 9 minutes was established. Between 13 and 14 minutes, methanol was exchanged for the initial eluting solvent and by 19 minutes the column had been reequilibrated for the next sample. The effluent was analyzed by a continuous flow radioactivity monitor (model ROMONA-D) interfaced with a Hewlett Packard Lab Automation System for quantitation of radioactive products. These were predominantly leukotriene C₄ ( LTC₄) which eluted at 6 minutes, and 5-hydroxyeicosatetraenoic acid (5-HETE) which eluted at 11 minutes (Musch et. al., supra). The results with and without test compound were used to calculate percent inhibition of LTC₄ and 5-HETE production for representative compounds of the invention as shown in Table 3 below:

TABLE 3

5-Lipoxygenase Assay[3]

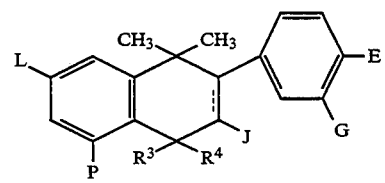

| E | G | J | P | L | R³/R⁴ | equals double bond | Dose μm | % Inhibition[3] 5-HETE | LTC₄ |
|---|---|---|---|---|---|---|---|---|---|
| OCH₃ | OCH₃ | H | OCH₃ | OCH₃ | =O | yes | 50 | 95 | 100 |
|  |  |  |  |  |  |  | 5 | 9 | 17 |
| OH | OH | H | OH | OH | =O | yes | 5 | 76 | —[4] |
|  |  |  |  |  | =O |  | 2 | 52 | 33 |
| OH | OH | OH | OH | OH | =O | yes | 50 | 95 | —[4] |
|  |  |  |  |  |  |  | 5 | 43 | —[4] |
| OCH₃ | OCH₃ | H | OCH₃ | OCH₃ | =O | no | 50 | 100 | 99 |
|  |  |  |  |  |  |  | 5 | 29 | 36 |
| OH | OH | H | OH | OH | =O | no | 2 | 0[2] | —[4] |
| OH | OH | H | OH | OCH₃ | =O | yes | 5 | 60 | —[4] |
| OAc[1] | OAc[1] | H | OAc[1] | OAc[1] | =O | yes | 5 | 53 | 43 |
| OCH₃ | OCH₃ | H | OCH₃ | OCH₃ | H,H | no | 5 | 35 | 53 |
| OH | OH | H | OH | OH | H,H | no | 5 | 55 | 52 |

TABLE 3-continued

5-Lipoxygenase Assay[3]

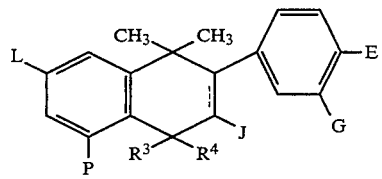

| E | G | J | P | L | $R^3/R^4$ | equals double bond | Dose μm | % Inhibition[3] 5-HETE | LTC$_4$ |
|---|---|---|---|---|---|---|---|---|---|
| OCH$_3$ | OCH$_3$ | H | OCH$_3$ | OCH$_3$ | CH$_3$,OH | no | 5 | 0[2] | 8 |
| OCH$_3$ | OCH$_3$ | H | OCH$_3$ | OCH$_3$ | H,OH | no | 5 | 5[2] | 32 |
| OCH$_3$ | OCH$_3$ | H | OCH$_3$ | OCH$_3$ | =N—OH | no | 5 | 100 | 65 |
|  |  |  |  |  |  |  | 1 | 28 | 26 |

[1]AcO = acetyloxy
[2]Expected to have activity at a higher dose.
[3]Mc-9 cell.
[4]No measurement taken.

5-Lipoxygenase Assay with Human Neutrophils

Human polymorphonuclear leukocytes (neutrophils) were obtained from normal healthy volunteers by venipuncture and collected with heparin anticoagulant. Neutrophils were isolated by Dextran/Ficol sedimentation as described (Billah et al., J. Biol. Chem. 260, 6899–6906 (1985)). In brief, 30 ml of blood was mixed with 5 ml of dextran (Sigma) solution and kept at 37 C for 30 min. The upper white cell-rich layer was removed and 10 ml was layered on 9 ml of Ficol-Paque solution (Pharmacia) and centrifuged at 280×g for 10 min. at 5° C. The supernatant was removed and the neutrophil pellet was resuspended in HEPES buffer containing 25 mM N-2-hydroxyethylpiperazine-N$^1$-2-ethanesulfonic acid HEPES, 125 mM NaCl, 2.5 mM KCl, 0.7 mM MgCl$_2$, 0.5 mM and 10 mM glucose at pH 7.4. The red cells in the suspension were lysed by hypotonic shock. The neutrophils were washed by centrifugation in HEPES buffer two times and finally resuspended at a concentration of 20×10$^6$ cells/ml in the presence of 1 mM CaCl$_2$.

Neutrophils (0.2 ml of suspension) were preincubated with dimethylsulfoxide (DMSO) vehicle with or without test compound (1 ul) for 4 minutes then incubated for 5 minutes with [$^{14}$C] arachidonic acid (Amersham, 59 Ci/mole) at a 9 uM final concentration, and the calcium ionophore A23187 (Calbiochem) at a 1 uM final concentration. These stimulants were added in 10 ul of water:ethanol (9:1). The reaction was stopped by addition of methanol (0.4 ml), and cellular debris was removed by centrifugation. Aliquots (100 ul) of the incubations were run on a Waters two pump HPLC system fitted with a DuPont Zorbax ODS, 5u, 4×80 cm Reliance Cartridge column and C18 "Guard Pak". The column was initially eluted at 2 ml/min with 80% of the mixture water:methanol:acetic acid (46:54:0.08) containing 1 mM EDTA adjusted to pH 6.0 with ammonium hydroxide (Pump A) and 20% methanol (Pump B). At 10 minutes, a linear gradient to reach 100% methanol (Pump B) at 27 minutes was established. Between 27 and 28 minutes, methanol was exchanged for the initial eluting solvent and by 35 minutes the column had been reequilibrated for the next sample. The effluent was analyzed by a continuous flow radioactivity monitor (model ROMONA-D) interfaced with a Hewlett Packard Lab Automation System for quantitation of radioactive products. These were predominantly leukotriene B$_4$ (LTB$_4$) which eluted at 7 minutes, and 5-hydroxyeicosatetraenoic acid (5-HETE) which eluted at 20 minutes. The results with and without test compound were used to calculate percent inhibition of LTB$_4$ and 5-HETE production for representative compounds of the invention as shown in Table 4 below:

TABLE 4

5-Lipoxygenase Assay With Human Neutrophils

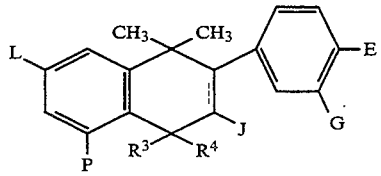

| E | G | J | P | L | K | $R^3/R^4$ | equals double bond | Dose μm | % Inhibition[1] 5-HETE | LTB |
|---|---|---|---|---|---|---|---|---|---|---|
| H | H | H | OCH$_3$ | OCH$_3$ | H | =O | no | 15 | 0[3] | 0[3] |
| OCH$_3$ | OCH$_3$ | H | OCH$_3$ | OCH$_3$ | H | =N—OCH$_3$ | no | 15 | 55 | 47 |
| OCH$_3$ | OCH$_3$ | CH$_3$ | OCH$_3$ | OCH$_3$ | H | =O | yes | 15 | 1[3] | 0[3] |
| OH | OH | CH$_3$ | OH | OH | H | =O | yes | 15 | 90 | 96 |
|  |  |  |  |  |  |  |  | 5 | 13 | 46 |

TABLE 4-continued
5-Lipoxygenase Assay With Human Neutrophils

| | | | | | | | equals double bond | Dose μm | % Inhibition[1] 5-HETE | LTB |
|---|---|---|---|---|---|---|---|---|---|---|
| OCH$_3$ | OCH$_3$ | H | OCH$_3$ | OCH$_3$ | H | =N—NH(CO)⌬ | no | 15 | 22 | 38 |
| OCH$_3$ | OCH$_3$ | H | OCH$_3$ | OCH$_3$ | H | =N—NH—C(O)—C$_6$H$_4$—OH | no | 15 | 41 | 50 |
| OCH$_3$ | OCH$_3$ | H | OCH$_3$ | OCH$_3$ | H | =N—NH(CO)NH$_2$ | no | 15 | 2[3] | 0 |
| OCH$_3$ | OCH$_3$ | CH$_3$ | OCH$_3$ | OCH$_3$ | H | =N—OH | no | 15 | 31 | —[2] |
| OCH$_3$ | OCH$_3$ | H | OCH$_3$ | OCH$_3$ | H | =N—NH(CO)CH$_3$ | no | 15 | 0[3] | 0[3] |
| OCH$_3$ | OCH$_3$ | H | OCH$_3$ | OCH$_3$ | H | =N—OH | yes | 15 | 0[3] | 9 |
| OCH$_3$ | OCH$_3$ | CHO | OCH$_3$ | OCH$_3$ | H | =O | no | 15 | 16 | 0 |
| OCH$_3$ | OCH$_3$ | H | OCH$_3$ | OCH$_3$ | H | =N—O(CO)CH$_3$ | no | 15 | 13 | 18 |
| OCH$_3$ | OCH$_3$ | H | OCH$_3$ | OCH$_3$ | OCH$_3$ | =O | no | 15 | 0[3] | 0[3] |

[1] Human PMN
[3] Expected to have activity at higher dose.
[2] No measurement taken.

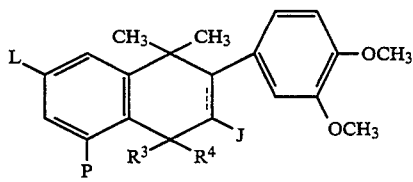

| J | P | L | R$^3$/R$^4$ | equals double bond | Dose μm | % Inhibition[1] 5-HETE | LTB |
|---|---|---|---|---|---|---|---|
| H | OH | OCH$_3$ | =O | no | 15 | 0[2] | —[3] |
| H | OH | OCH$_3$ | =N—OH | no | 15 | 42 | —[3] |
| CH$_2$—CH—CH$_2$ | OCH$_3$ | OCH$_3$ | =O | no | 15 | —[3] | 0[2] |
| H | H | OCH$_3$ | =N—OMe | no | 15 | 74 | —[3] |
| H | OCH$_3$ | OCH$_3$ | =N—NH$_2$ | no | 15 | 35 | —[3] |
| H | OCH$_3$ | OCH$_3$ | =N—O—C(O)—tC$_4$H$_9$ | no | 15 | 0[2] | —[3] |
| H | OCH$_3$ | OCH$_3$ | H, NH(CO)CH$_3$ | no | 15 | 0[2] | 4[2] |
| H | OCH$_3$ | OCH$_3$ | H, NH$_2$ | no | 15 | 0[2] | 0 |
| CO$_2$C$_2$H$_5$ | OCH$_3$ | OCH$_3$ | =O | no | 15 | 69 | 89 |
| H | OCH$_3$ | OCH$_3$ | S—C$_6$H$_4$—Cl | no | 15 | 36 | —[3] |
| H | H | OCH$_3$ | =O | no | 15 | 42 | —[3] |
| H | H | OCH$_3$ | =O | yes | 15 | 79 | —[3] |
| H | OCH$_3$ | H | =O | no | 15 | 23 | —[3] |
| H | OCH$_3$ | H | =O | yes | 15 | 28 | —[3] |

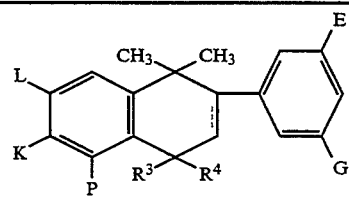

| E | G | P | L | K | R$^3$/R$^4$ | equals double bond | Dose μm | % Inhibition[1] 5-HETE | LTB |
|---|---|---|---|---|---|---|---|---|---|
| OCH$_3$ | OCH$_3$ | OCH$_3$ | OCH$_3$ | H | =O | yes | 15 | 0[2] | 0[2] |
| H | OH | OH | OH | H | =O | no | 15 | 23 | —[3] |
| OH | OH | OH | OCH$_3$ | H | =O | no | 15 | 75 | —[3] |
| OH | OH | OH | OH | H | =O | yes | 15 | 11 | —[3] |

TABLE 4-continued
5-Lipoxygenase Assay With Human Neutrophils

| | | | | | | | | | |
|---|---|---|---|---|---|---|---|---|---|
| OCH$_3$ | OCH$_3$ | OCH$_3$ | OCH$_3$ | OCH$_3$ | =O | yes | 15 | 7[2] | 1[2] |
| OH | OH | OH | OH | H | =N—OH | no | 15 | 57 | —[3] |

[Structure: a bicyclic compound with CH$_3$O, OCH$_3$ substituents, gem-dimethyl, ketone (=O), and substituents A, B]

| A | B | Dose (μm) | % Inhibition[1] 5-HETE | LTB |
|---|---|---|---|---|
| C$_6$H$_5$ | H | 15 | 64 | —[3] |
| CH$_2$–C$_6$H$_4$–OCH$_3$ | H | 15 | 86 | —[3] |
| CH$_2$–C$_6$H$_4$–OCH$_3$ | CH$_2$–C$_6$H$_4$–OCH$_3$ | 15 | 88 | —[3] |

[Structure: open-chain compound with CH$_3$O-substituted aryl group, gem-dimethyl, substituents P, X, R$^3$, R$^4$, J, L, and OCH$_3$-aryl groups]

| X | R$^3$/R$^4$ | J | L | P | Dose μM | % Inhibition[1] 5-HETE | LTB$_4$ |
|---|---|---|---|---|---|---|---|
| NH | H,H | H | OCH$_3$ | OCH$_3$ | 15 | 39 | 63 |
| NH | H,H | H | OCH$_3$ | H | 15 | 73 | —[3] |
| NH | =O | H | OCH$_3$ | OCH$_3$ | 15 | 0[2] | 2[2] |
| O | =O | H | OCH$_3$ | OCH$_3$ | 15 | 9[2] | —[2] |
| O | =O | CH$_3$ | OCH$_3$ | OCH$_3$ | 15 | 20 | 2 |
| CH$_2$ | =O | H | OCH$_3$ | OCH$_3$ | 15 | 87 | 97 |
| CH$_2$ | =N—OH | H | OCH$_3$ | OCH$_3$ | 15 | 87 | —[3] |
| CH$_2$ | =O | H | H | OCH$_3$ | 15 | 61 | 22 |
| O | H,H | H | OCH$_3$ | OCH$_3$ | 15 | 39 | 28 |

[Structure: benzosuberone-type compound with gem-dimethyl, aryl substituent with F, E, G groups, and L, K, P, W, J, X positions]

| X | equals double bond | W | J | F | E | G | L | P | Dose μM | % Inhibition 5-HETE | LTB$_4$ |
|---|---|---|---|---|---|---|---|---|---|---|---|
| O | no | H | H | H | OCH$_3$ | OCH$_3$ | OCH$_3$ | OCH$_3$ | 15 | 51 | 45 |
| O | no | H | H | H | OH | OH | OH | OH | 15 | 88 | —[3] |
| N—OH | no | H | H | H | OCH$_3$ | OCH$_3$ | OCH$_3$ | OCH$_3$ | 15 | 2 | —[3] |
| O | no | CH$_3$ | CH$_3$ | H | OCH$_3$ | OCH$_3$ | OCH$_3$ | OCH$_3$ | 15 | 54 | —[3] |
| O | no | H | CH$_3$ | H | OCH$_3$ | OCH$_3$ | OCH$_3$ | OCH$_3$ | 15 | 28 | —[3] |
| O | yes | H | — | H | OCH$_3$ | OCH$_3$ | OCH$_3$ | OCH$_3$ | 15 | 48 | —[3] |
| O | no | H | S–C$_6$H$_5$ | H | OCH$_3$ | OCH$_3$ | OCH$_3$ | OCH$_3$ | 15 | 61 | —[3] |

TABLE 4-continued

| | | | | | | | | | | | |
|---|---|---|---|---|---|---|---|---|---|---|---|
| 5-Lipoxygenase Assay With Human Neutrophils | | | | | | | | | | | |
| O | no | H | H | OCH$_3$ | H | OCH$_3$ | OCH$_3$ | OCH$_3$ | 15 | 46 | 46 |

[1]Human PMN
[2]Expected to have activity at higher dose.
[3]No measure taken.

In the treatment of inflammation, the active compounds of this invention can be administered in conventional unit dosage forms such as tablets, capsules, pills, powders, granules, sterile parenteral solutions or suspensions, suppositories, mechanical delivery devices, e.g., transdermal, and the like. The compounds of this invention may be administered at doses of about 0.5 to about 50 mg/kg, preferably, from about 1 to about 20 mg/kg, of body weight per day. Preferably, the total dosages are administered 2-4 divided doses per day.

The compounds of formula Ia or Ib are useful in the treatment of hyperproliferative skin disease, e.g., psoriasis, in mammals, e.g., humans, which may be demonstrated by their 5-lipoxygenase inhibitory activity as discussed above or by the Arachidonic Acid Mouse Ear Test as described below.

Arachidonic Acid Mouse Ear Test, Materials and Methods

Charles River, female, CD, (SD) BR mice, 6 weeks old, are caged 8/group and allowed to acclimate 1-3 weeks prior to use.

Arachidonic acid (AA) is dissolved in reagent grade acetone (2 mg/0.01 ml) and stored at −20° C. for a maximum of 1 week prior to use. Inflammatory reactions are induced by applying 10 ml of AA to both surfaces of one ear (4 gm total).

Test drugs are dissolved in either reagent grade acetone or aqueous ethanol (only if insoluble in acetone) at the same doses selected by Opas et al., Fed. Proc. 43, Abstract 2983, p. 1927 (1984) and Young et al., J. Invest. Dermatol. 82, pp. 367-371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean ± standard error and all possible comparisons are made via Duncan's Multiple Range Statistic.

The compounds 3-(3,4-dihydroxyphenyl)-2,6,8-trihydroxy--4,4-dimethyl-1(4H)-naphthalenone; 3-(3,4-dimethoxyphenyl)-6,8-dimethoxy-4,4-dimethyl-3,4-dihydro-1(2H)-naphthalenone; 3-(3,4-dihydroxyphenyl)-8-hydroxy-6-methoxy-4,4-dimethyl-1(4-H)-naphthalenone; and 3-(-3,4dihydroxyphenyl)-6,8-dihydroxy-4,4-dimethyl-1(4H)-naphthalenone and the trisodium salt of 3(3,4-dihydroxyphenyl)-6,8-dihydroxy-4,4-dimethyl-1(4H) -naphthalenone provided 68%, 50%, 65%, 60% and 90% inhibition, respectively, at 1 mg/ear, in the above test procedure.

As a result of the administration of a compound of formula Ia or Ib, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

When administered for the treatment of hyperproliferative skin disease, the compounds may be administered topically, orally, rectally or parenterally. When administered topically, the amount of compound administered varies widely with the amount of skin being treated, as well as with the concentration of active ingredient applied to the affected area. When administered orally, the compounds of formula I are effective for the treatment of hyperproliferative skin disease at doses ranging from about 0.1 mg to about 100 mg, which may be administered in divided doses. When administered rectally, the compounds of formula I may be administered in doses ranging from about 0.1 mg to about 1000 mg. When administered parenterally, the compounds of formula I are effective for the treatment of hyperproliferative skin disease in doses ranging from about 0.1 mg/kg body weight to about 10 mg/kg body weight which may be administered in divided doses.

Included within the invention are preparations for topical application to the skin whereby the compounds having structural formula I are effective in the treatment and control of skin diseases characterized by rapid rates of cell proliferation and/or abnormal cell proliferation, e.g., psoriasis.

In a preferred method of treating hyperproliferative skin diseases, a pharmaceutical formulation comprising a compound of formula Ia or Ib, (usually in concentrations in the range of from about 0.1 percent to about 10 percent, preferably from about 1 percent to about 5 percent) together with a non-toxic, pharmaceutically acceptable topical carrier, is applied several times daily to the affected skin until the condition has improved. Topical applications may then be continued at less frequent intervals (e.g. once a day) to control mitosis in order to prevent return of severe disease conditions.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Formulations for topical application, e.g., for use in treating hyperproliferative skin diseases, may include the above liquid forms, creams, aerosols, sprays, dusts, powders, lotions and ointments which are prepared by combining an active ingredient according to this inventions with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oily base and will, in general., also include one or more of the following, namely, stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples are intended to illustrate, but not to limit, the present invention.

EXAMPLE 1

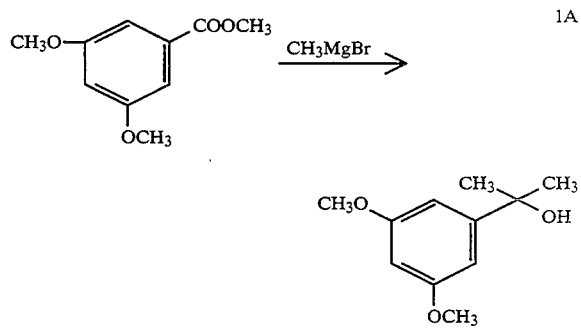

A. To a flask equipped with a rubber septum, a condenser with N₂ inlet and a dropping funnel was introduced 109 ml of 3.0N methyl magnesium bromide by syringe. A solution of 30 g of methyl 3,5-dimethoxybenzoate in 80 ml of anhydrous ether was added to the stirred Grignard solution through the dropping funnel over 40 minutes under N₂ at room temperature. During the addition the reaction mixture started to reflux gently. After the addition the resulting mixture was stirred for another hour,. It was then cooled to −10° C. and quenched slowly by adding saturated aqueous NH₄Cl solution. The organic layer was separated, the aqueous layer was extracted with ethyl ether and the combined organic layers were washed with brine, dried over anhydrous MgSO₄ and concentrated to give 30.50 g of oil which crystallized on standing. The product was purified by column chromatography on SiO₂ (eluting solvents 2:1 CH₂Cl₂/hexane, then CH₂Cl₂, and then gradient up to 15% ether in CH₂Cl₂) to give pure product 1A above, 28.8 g (96% yield), m.p. 52.5°–54° C.

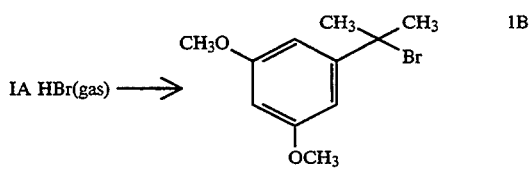

B. Into a flask equipped: with a nitrogen inlet, a rubber septum, and a drying tube was introduced a solution of 30 g of the product A above in 150 ml of anhydrous CH₂Cl₂ and 19.6 g of anhydrous MgSO₄ was added. The stirred mixture was cooled in an ice water bath, then dry HBr gas was bubbled in for 55 minutes at 0° C. (until HBr was escaping through the drying tube). The reaction mixture was filtered and the filtrate was concentrated in vacuum to give an oil which solidified at −78° C. to give the compound of formula 1B above. The product 1B was thermally unstable and moisture sensitive and was maintained under nitrogen and at low temperature.

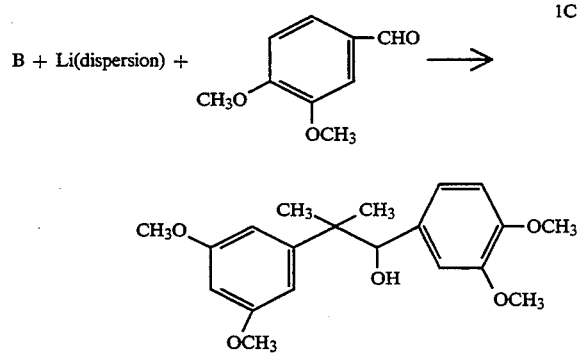

C. To a flask equipped with a nitrogen inlet, an addition funnel, and a rubber septum were added 1.22 g of Li dispersion and 5 ml of anhydrous hexane. The mixture was stirred for a few minutes and then was allowed to stand until all the Li floated on the top of the solution. The bottom clear hexane was removed by pipette, then 5 ml of dry tetrahydrofuran (THF) was added. The mixture was then cooled to −20° C., a solution of 3.42 g of product 1B above and 1.83 g of 3,4-dimethoxy-benzaldehyde in 20 ml of dry THF were added dropwise from an addition funnel over 30 minutes. The resulting reaction mixture was stirred for another 20 minutes then cooled to −78° C. and quenched slowly by addition of 30 ml of saturated aqueous NH₄Cl solution. The reaction mixture was allowed to warm up to room temperature with stirring until it gave a clear yellow solution. Two layers were separated. The bottom aqueous layer was extracted with ethyl ether. The combined organic layers were washed with brine, dried over anhydrous Na₂SO₄ and concentrated to give a crude product which was separated by preparative TLC (5% ether in CH₂Cl₂) to give 2.3 g of the desired product of formula 1C above as an oil, which was used as such in step D below.

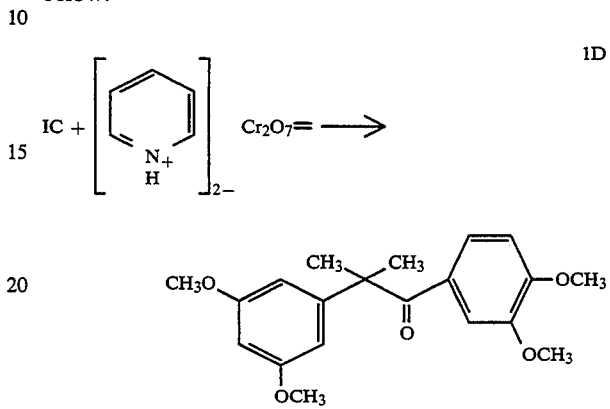

D. To a solution of 49 mg of product 1C above in 0.5 ml of anhydrous dimethylformamide (DMF) cooled at 0° C. were added 4 equivalents (213 g) of pyridinium dichromate (PDC) under N₂. The mixture was then stirred at 0° C. for 6 hours, 500 ml of water were added, and the resulting mixture was extracted with ethyl ether (3×5 ml). The ether extracts were concentrated and the residue was purified by preparative TLC (eluting solvent: CH₂Cl₂) to give 37 mg of the desired compound of formula 1D above, m.p. 99°–100° C.

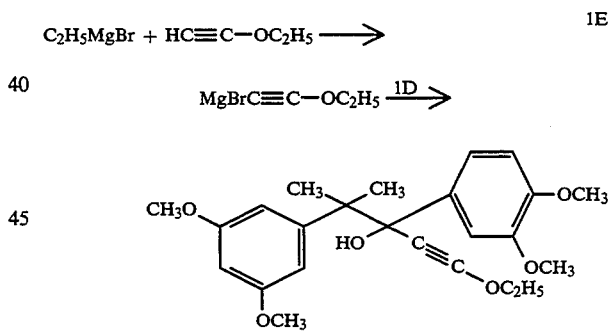

E. To 445 ml of anhydrous THF was added 103.7 ml of 2.8N ethyl ether solution of ethylmagnesium bromide (by syringe) under N₂. To the stirred solution was then added 47 ml of ethyl ethyne ether solution dropwise over ½ hour. The resulting solution was stirred for another hour at room temperature, then a solution of 55.50 g of product 1D above in 160 ml of anhydrous THF was added over 30 minutes with warming to dissolve product 1D. After the addition the resulting reaction mixture was stirred at room temperature for 10 hours. The reaction mixture was poured into 1000 ml of ice-water, the mixture was extracted with ethyl etcher, the dark solution was filtered through Celite to give a clear two phase filtrate. The aqueous layer was extracted with ethyl ether. The combined ether layers were washed with brine, dried over anhydrous MgSO₄ in the presence of NaHCO₃ and concentrated. The residue was passed though a short column of SiO₂ (using CH$_2$Cl$_2$/ether 2:1). After concentration, the mixture gave 66.82 g of crude product 1E above which was used directly for next step (F below) without further purification.

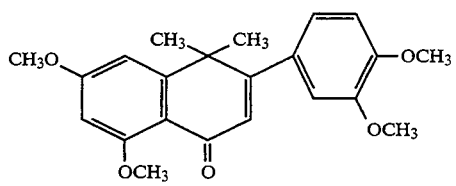

F. Anhydrous methylene chloride (1.3 1) was introduced under N$_2$ to a flask equipped with mechanical stirrer. An anhydrous CH$_2$Cl$_2$ solution (200 ml) of crude product 1E above (66.82 g) (previously azeotropically dried over anhydrous toluene) was added. Anhydrous MgSO$_4$ (29.14 g) was then added and the stirred mixture was cooled to −78° C. A solution of 49.7 mL of trifluoroacetic acid in 200 ml of anhydrous methylene chloride was added from a dropping funnel over 10 minutes. After an additional 15 minutes of stirring at −78° C., the cooling bath was removed, and the mixture was quenched with a ⅓ of a solution of 178.5 g of anhydrous K$_2$CO$_3$ in 1.95 L of distilled water. After 30 seconds of stirring, another ⅓ of the K$_2$CO$_3$ solution was added and stirred for 30 seconds, and then the last ⅓ of the K$_2$CO$_3$ solution was added. The mixture was stirred at room temperature until the internal temperature raised to about 0° C. The two layers were separated and the aqueous layer was extracted with 500 ml of ethyl acetate. The combined ethyl acetate extract and CH$_2$Cl$_2$ layer were dried over anhydrous MgSO$_4$, filtered and concentrated.

The crude product 1F was purified by flash chromatography on SiO$_2$. The column was first eluted with CH$_2$Cl$_2$ until the non-polar side products were collected, then with a gradient of increasing ether content up to 30% ether in CH$_2$Cl$_2$. This gave 41.0 g (59% yield) of desired product 1F, m.p. 171°-172° C.

EXAMPLE 2

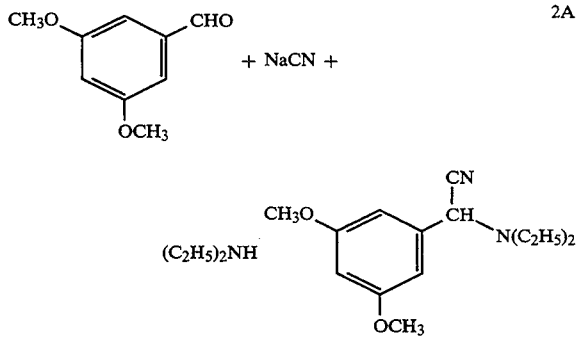

A. In a two necked round bottom flask provided with reflux condenser and addition funnel, a CH$_3$OH (15 ml) solution of 3,5-dimethoxy benzaldehyde (1.66 g) was added dropwise at room temperature over a period of two hours to solution of NaCN (0.588 g) and diethylamine hydrochloride (1.315 g) in 5 ml of water. After the addition, the solution was heated at 40° C. for twenty hours, then cooled to room temperature. Water (1.5 liters) was added and the resulting mixture was extracted several times with EtOAc. The combined extracts were washed with water and dried (Na$_2$SO$_4$). Evaporation of the solvent under reduced pressure gave 2.18 g (88%) of the product of formula 2A.

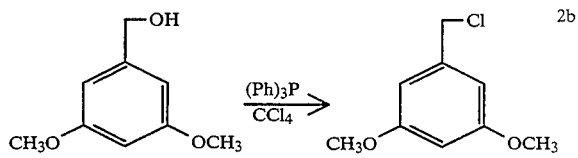

B. 3,5-dimethoxybenzyl alcohol (16.8 g; 0.1 mole) and triphenylphosphine (28 g; 0.12 moles) were refluxed in 100 ml of dry CCl$_4$ under N$_2$. After three hours, more (C$_6$H$_5$)$_3$P (3.0 g) was added, and the mixture was refluxed overnight. After cooling to room temperature, the mixture was purified by flash chromatography (SiO$_2$) (10% EtOAc/Hexanes) yielding 17.6 g (94%) of product of formula 2B above.

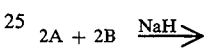

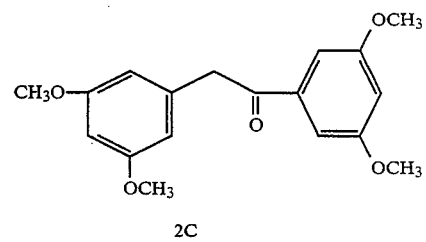

C. The apparatus consisted of a dry three necked round bottom flask provided with two dry addition funnels. NaH (2.50 g) (60% oil dispersion) was washed three times under N$_2$ with Hexanes in the three necked flask. The NaH was then suspended in 20 ml of dry DMF. One of the addition funnels was charged with 3,5-dimethoxy benzyl chloride of formula 2B (7.7 g; 41 mmoles) dissolved in 30 ml of dry DMF.

The other addition funnel was charged with α-cyano-N,N-diethyl-3,5-dimethoxy-benzylamine of formula 2A (9.5 g; 38.3 mmoles) dissolved in 40 ml of dry DMF. The latter was added dropwise at room temperature to the suspension of NaH over a period of one hour. After the addition, the mixture was stirred for 3½ hours, then the solution of 3,5-dimethoxybenzylchloride of formula 2B was added dropwise. After the solution, the mixture was stirred under N$_2$ overnight. The reaction was quenched by careful addition of 25 ml of CH$_3$OH. The solvents were removed using high vacuum at a bath temperature of 65° C. The resulting paste was kept at that temperature for six hours, then cooled to room temperature. This paste was triturated with 6N aqueous HCl (200 ml), then the mixture was heated at a bath temperature of 125° C. for 3½ hours.

The mixture was cooled to room temperature, diluted with water (200 ml), and extracted with CH$_2$Cl$_2$. The combined extracts were washed with water and dried (Na$_2$SO$_4$). The reaction mixture was purified by flash chromatography (SiO$_2$) (15% EtOAc/Hexanes) yielding 9.30 g (76%) of product of formula 2C.

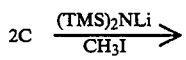 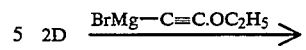

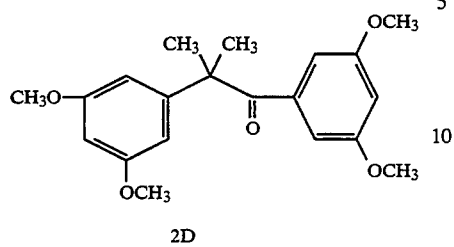

2D

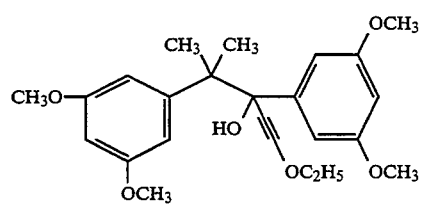

2E

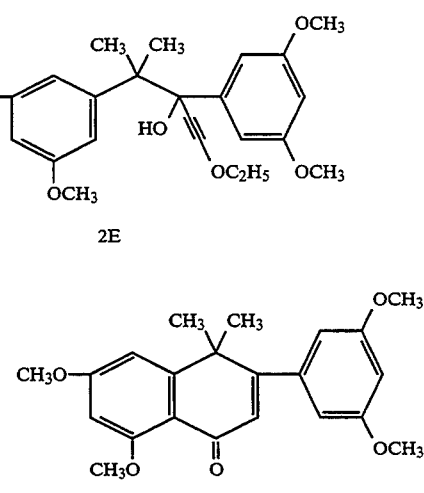

2F

D. 3.2 g (10 mmoles) of the compound of formula 2C above dissolved in dry THF (45 ml) were added dropwise under $N_2$ to a stirred precooled (dry ice-acetone bath) 1M THF solution of lithium bis(trimethylsilyl)amide (13 ml) over a period of one hour in a dry apparatus.

After the addition, the resulting yellow solution was stirred under $N_2$ for two hours at $-78°$ C., then 0.93 ml (15 mmoles) of iodomethane was added in one portion. The solution was then let warm up and stirred at room temperature for 20 hours. The solution was cooled at $-78°$ C. and 17 ml (17 mmoles) of 1M THF solution of lithium bis(trimethylsilyl)amide were added dropwise over a period of five minutes. After the addition, the solution was stirred for three hours at $0°-5°$ C. (ice bath). 2.5 ml of $CH_3I$ were then added in one portion. The solution was then warmed up and stirred at room temperature overnight. The solution was then diluted with ethyl acetate (total volume=300 ml), washed with 1N aqueous HCl, then with brine, then with water, and dried over anhydrous $Na_2SO_4$. The crude reaction mixture was filtered through $SiO_2$ ($CH_2Cl_2$) yielding 3.22 g of the title compound of formula 2D (92%).

E. By following the same procedures of step E and step F in the EXAMPLE 1, a compound of formula 2D above was first converted to a compound of formula 2E, and then consequently converted to a compound of formula 2F above.

By following the same procedures from A to E of EXAMPLE 2, the following compounds in Table 4 were prepared.

TABLE 4

| Starting Materials | Product of Invention | Product m.p. °C. |
|---|---|---|
| CH3O—C6H3(OCH3)—CHO; H3CO—C6H3(OCH3)—CH2OH | 2F | 144–145° |
| CH3O—C6H3(OCH3)—CHO; H3CO—C6H2(H3CO)(OCH3)—CH2OH | 2H | 162–163° |
| C6H3(CH3O)(OCH3)—CHO; CH3O—C6H3(OCH3)—CH2OH | 2I | 171–172° |

TABLE 4-continued

| Starting Materials | Product of Invention | Product m.p. °C. |
|---|---|---|
| 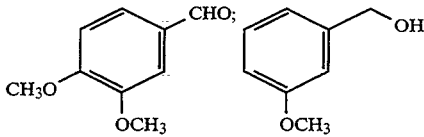 | 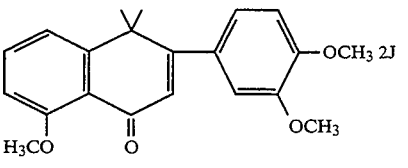 2J | 339* |
| | + | |
| | 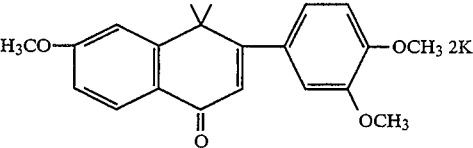 2K | 158–159° |

*mass spectrometry, m/e (M + 1)

EXAMPLE 3

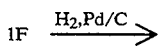

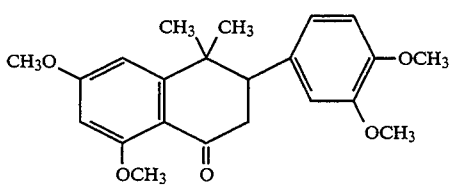

3A 150 g of product 1F of Example 1 above was divided into two portions of 75 g. Each portion was hydrogenated in the presence of 7 g of 10% Pd on carbon at room temperature in 1400 ml of benzene and initial $H_2$ pressure of 60 psi. After six hours, the reaction mixture was filtered through a pad of Celite ® and the filtrate was concentrated. The residue (combined each 75 g portions) was purified by flash chromatography on $SiO_2$. The column was eluted first with 40% ethylacetate/hexane. After the less polar compound was collected, the column was eluted with ethylacetate to give 137 g of desired product 3A (91% yield) which was recrystallized from ethylacetate, m.p. 176°–177° C.

By following the above hydrogenation procedure, the following were prepared, Table 5.

TABLE 5

| Starting Materials | Product of Invention | Product m.p. (°C.) or MS* (m/e) |
|---|---|---|
| 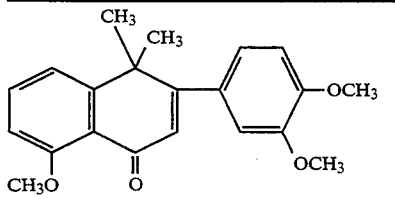 | 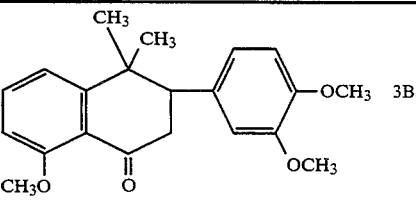 3B | 125–127° |
| 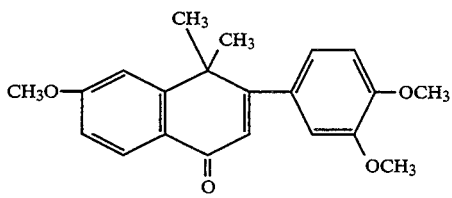 | 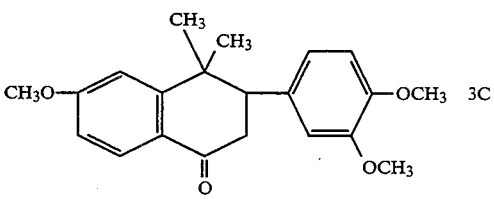 3C | 340* |
| 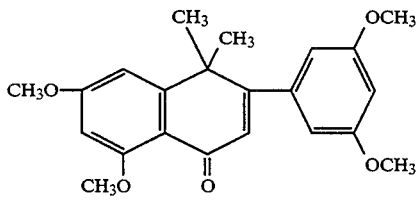 | 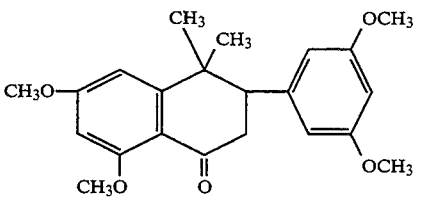 3D | 370* |

*MS: mass spectometry

EXAMPLE 4

EXAMPLE 4

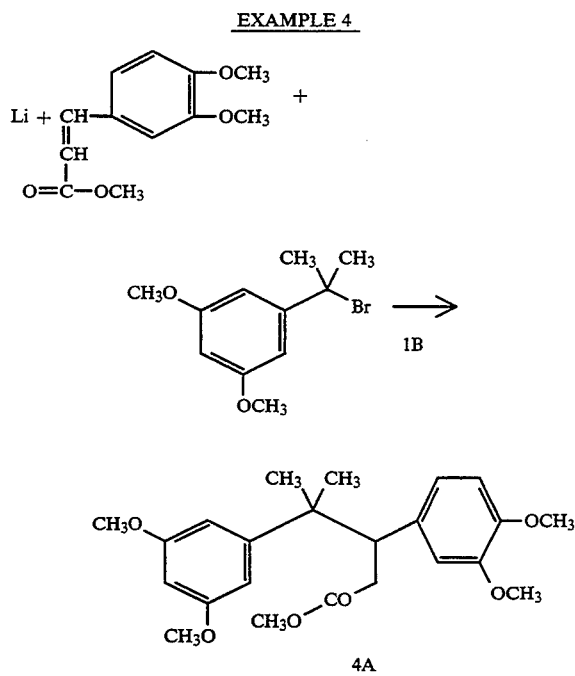

A. To a suspension of 0.111 g of lithium dispersion (prewashed with hexane) in 1 ml of dry THF was added a solution of 0.444 g of methyl 3,4-dimethoxycinnamate and 0.259 g of 2-bromo-2-(3,5-dimethoxyphenyl)propane of formula 1B in 1 ml of dry THF over 15 minutes at −20° C. under nitrogen. The resulting mixture was stirred vigorously for another 50 minutes. It was diluted with ethyl ether and then quenched with a saturated aqueous ammonium chloride solution. The organic layer was separated, washed with brine, dried over anhydrous magnesium sulfate and concentrated. The residue was purified by preparative TLC (5% ether in $CH_2Cl_2$) to give 0.240 g (60% yield) of the desired product of formula 4A above, mass spectrometry, m/e 402 (M+).

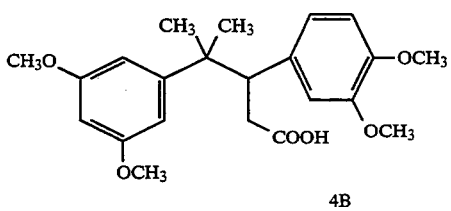

B. A solution of 0.1386 g of the compound of formula 4A above in 1.38 ml of THF, 1.38 ml of 1N LiOH and 1 ml of methanol was stirred at room temperature under $N_2$ overnight (15 hours), then the solvent was removed under vacuum. The residue was dissolved in 2 ml of water, which was then extracted with ethyl ether. The aqueous solution was then cooled in ice-water bath and acidified with 2N HCl to pH between 2 and 3. The resulting mixture was extracted with ethyl acetate. The ethyl acetate extracts were washed with brine, dried over anhydrous $MgSO_4$ and concentrated to give compound 4B above as a white solid, 0.106 g (79% yield), mass spectrometry, m/e 388 (M+).

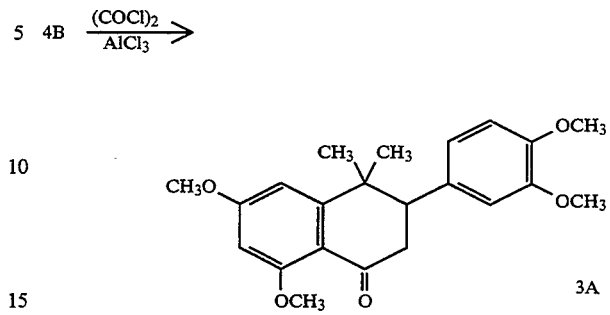

C. To a solution of 83 mg of the compound of formula 4B above in 1.6 ml of dry methylene chloride was added 21 μl of oxalyl chloride and 1.3 μl of N,N-dimethylformamide at room temperature under $N_2$. The resulting solution was stirred for 10 minutes, then it was cooled to 0° C. and 1 equivalent (28.5 mg) of anhydrous aluminum chloride was added. The resulting mixture was stirred at 0° C. for 20 minutes then it was quenched by aqueous saturated sodium bicarbonate solution. The organic solution was separated, dried over $MgSO_4$ and concentrated. The crude product of formula 3A above, 0.75 mg (95% yield) was recrystallized from ethyl acetate to give pure product 3A, m.p. 175°–176° C.

By the same procedure, starting from 2-chloro-2-(3,4,5-trimethoxyphenyl) propane, 3-(3,4-dimethoxyphenyl)-3,4-dihydro-6,7,8-trimethoxy-4,4-dimethyl-1(2H)-naphthalenone was prepared, mass spectrometry m/e 401 (M+1).

EXAMPLE 5

EXAMPLE 5

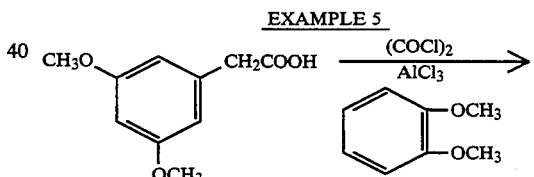

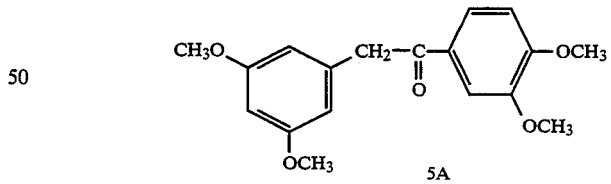

A. 11.0 g of 3,5-dimethoxyphenylacetic acid was dissolved in $CHCl_3$ (55 ml) in a dry flask. 10.0 ml of oxalyl chloride was added and the solution was refluxed until the evolution of HCl was ceased. The solvent and excess oxalyl chloride was removed first using vacuum, then high vacuum.

The resulting mixture was dissolved in veratrole (25 ml) and cooled in a ice bath in a three necked Morton flask provided of mechanical stirrer and dry reflux condenser with drying tube.

8.2 gm of $AlCl_3$ were added in portions over a period of 1¼ hours. After the addition, the reaction mixture was stirred in ice bath for three hours. The reaction was then quenched by careful addition of ice water. The mixture was extracted with ethyl ether/ethyl acetate (1:1). The combined extracts were washed with water and dried over Na$_2$SO$_4$.

The reaction mixture was purified by column chromatography (SiO$_2$) (50% Hexanes/CHCl$_3$) yielding 10.5 g (64%) of the compound of formula 5A above, which was recrystallized from CH$_3$OH to provide pure compound 5A, m.p.=70°–71° C.

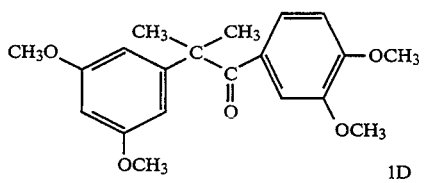

1D

B. 15.0 g of NaH (50% oil dispersion) were washed three times with hexanes under Argon gas in a dry three necked Morton flask provided with dry reflux condenser and dry addition funnel containing 15.0 g of the compound of formula 5A above dissolved in 60 ml of 1,2-dimethoxyethane. The reflux condenser was provided of a rubber septum with a needle connected to an end valve.

After the washings, the NaH was suspended in 85 ml of 1,2-dimethoxyethane (DME) and cooled in ice bath. The starting material was added dropwise over a period of 1½ hours. After the addition, the paste was stirred in ice bath until the evolution of H$_2$ was ceased. 30 ml of CH$_3$I in 30 ml of DME were added slowly dropwise, then the paste was stirred in ice bath for one hour, then heated at 65°–70° C. overnight. After cooling at room temperature, 10 ml more of the CH$_3$I were added and the mixture was heated again at 65°–70° for 24 hours. After cooling in ice bath, the reaction mixture was quenched by careful addition of water (100 ml). The aqueous layer was separated and extracted with ether. The combined organic solutions were washed with water and dried over Na$_2$SO$_4$. The reaction mixture was used as such for the next step C below, purified by column chromatography (SiO$_2$) (50% Hexanes/CHCl$_3$).

An analytical sample of product 1D above was obtained by recrystallization from CH$_3$OH, m.p.=99°–100° C.

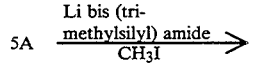

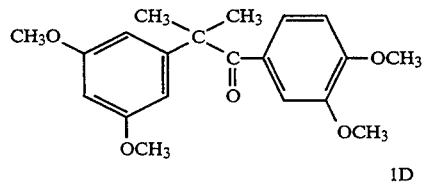

1D

Alternative Step B 3.2 g (10 mmoles) of the compound of formula 5A above dissolved in dry THF (45 ml) were added dropwise under N$_2$ to a stirred precooled (dry ice-acetone bath) 1M THF solution of lithium his (trimethylsilyl) amide (13 ml) over a period of one hour in a dry apparatus.

After the addition, the resulting yellow solution was stirred under N$_2$ for two hours at $-78°$ C., then 0.93 ml (15 mmoles) of iodomethane was added in one portion. The solution was then let warm up and stirred at room temperature for 20 hours. The solution was cooled at $-78°$ C. and 17 ml (17 mmoles) of 1M THF solution of lithium bis(trimethylsilyl)amide were added dropwise over a period of five minutes. After the addition, the solution was stirred for three hours at 0°–5° C. (ice bath). 2.5 ml of CH$_3$I were then added in one portion. The solution was then warmed up and stirred at room temperature overnight. The solution was then diluted with ethyl acetate (total volume=300 ml), washed with 1N aqueous HCl, then with brine, then with water, and dried over anhydrous Na$_2$SO$_4$. The crude reaction mixture was filtered through SiO$_2$ (CH$_2$Cl$_2$) yielding 3.22 g of the title compound of formula 1D (92%).

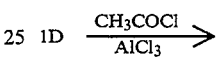

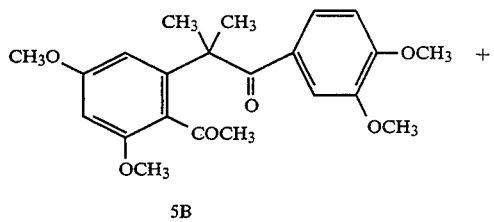

5B

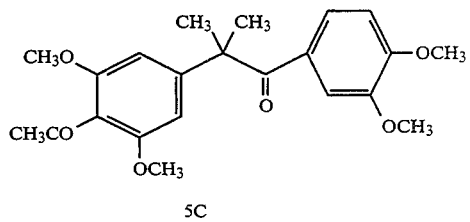

5C

C. 8.5 ml of acetyl chloride were added in one portion to 16.3 g of the compound of formula 1D above dissolved in nitrobenzene (160 ml) in a dry three necked Morton flask provided of mechanical stirrers and of a dry reflux condenser with a drying tube. The dark solution was cooled in ice bath, then 15.0 g of AlCl$_3$ were added in portions over a period of two hours. After the addition, the black solution was stirred in ice bath for an additional 1¼ hour, then the reaction was quenched by careful addition of water. The organic layer was separated. The aqueous layer was extracted with ethyl acetate (EtOAc). The combined organic solutions were washed with water and dried (Na$_2$SO$_4$).

The reaction mixture was partially purified by column chromatography (SiO$_2$) (CHCl$_3$). Two components were isolated. The less polar component was further purified by flash chromatography (SiO$_2$) (20% EtOAc/Hexanes), yielding 3.6 g (20%) of the compound of formula 5C above, which was recrystallized from ethyl acetate/hexane, m.p. 128°–129° C.

The more polar component, which is the compound of formula 5B above (9.5 g) (52%), m.p. 104°-106° C., was used as such for the reaction in step E below.

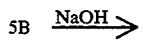

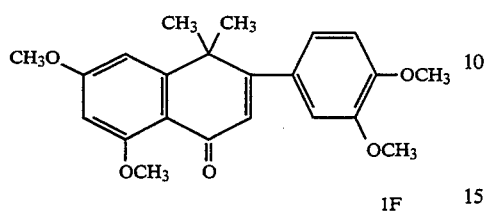

E. A compound of formula 5B (5.0 g) above was refluxed for two days in 50 ml of THF and 25 ml of 1N NaOH. After cooling to room temperature, the solution was diluted with water and the aqueous layer was separated and extracted with diethyl ether. The combined organic solutions were washed with water and dried over $Na_2SO_4$. The organic solution was purified by column chromatography ($SiO_2$) (10% ethyl acetate/$CHCl_3$) to yield 1.9 g (39%) of the product of formula 1F above which was recrystallized twice from ethyl acetate/hexane, m.p. 171°-172° C.

EXAMPLE 6

EXAMPLE 6

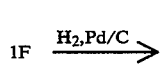

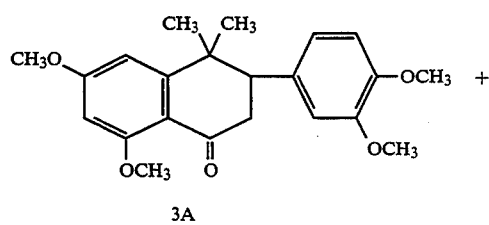

40.0 g of the compound of formula 1F above were hydrogenerated at 55 psi using 9.35 g of 10% Pd/C in benzene (125 ml). After six hours, the reaction mixture was filtered through Celite ® and the filtrate was purified by flash chromatography ($SiO_2$). The column was eluted first with 40% ethyl acetate/hexane until the less polar component of the mixture was collected, then with ethyl acetate until the more polar component was collected.

The more polar component was recrystallized from ethyl acetate/hexane yielding two crops (34.2 g and 3.0 g) (92%) of the compound of formula 3A, m.p. 175°-176° C. The less polar compound was recrystallized twice from ethyl acetate/hexanes to yield 0.86 g of a compound of formula 5D, m.p. 161°-162° C.

EXAMPLE 7

EXAMPLE 7

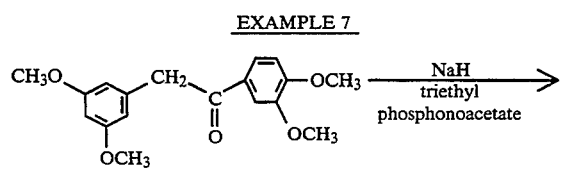

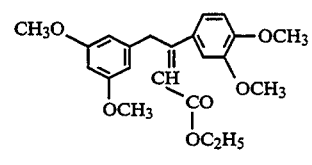

A. 7.0 g of a 50% oil suspension of NaH was added in portions to precooled (ice bath) triethyl phosphonoacetate (60 ml) with stirring under $N_2$ in a dry apparatus.

The mixture was stirred in an ice bath until the formation of $H_2$ ceased. 5.0 g of the compound of formula 7A above was added in one portion and then the solution was heated at 120°-125° C. for 12 hours. The hot water and dried over $Na_2SO_4$. After evaporation of the solution was then poured in ice water and extracted with $CH_2Cl_2$ (700 ml). The combined extracts were washed with solvent, the excess reagent was distilled under high vacuum. The resulting mixture was purified by flash chromatography ($SiO_2$). The column was eluted first with 10% ethyl acetate/hexanes (2 gallons), then with 15% ethyl acetate/hexanes yielding 5.0 g (82%) of product of formula 7B above which was used as such for step B below.

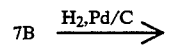

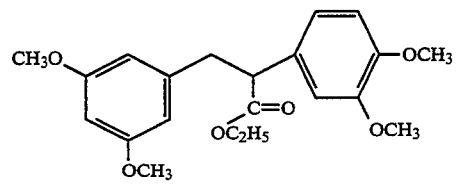

B. The product of formula 7B above obtained from step A (5.0 g) was hydrogenated with 10% Pd/C (2.0 g) in benzene (150 ml) at room temperature overnight at 50 psi of pressure. The catalyst was then filtered through Celite and washed with ethyl acetate. Evaporation of the filtrate gave 4.69 g (95%) of the compound of formula 7C, as an oil.

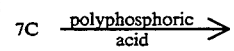

-continued

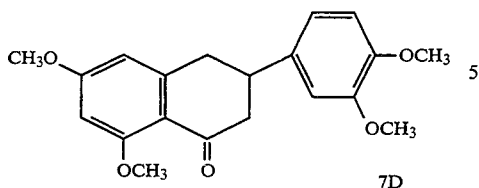

C. 4.1 g of the compound of formula 7C from step B above and 50 g of polyphosphoric acid were mixed at 85°–90° C. for two hours. Ice was then added to the red thick oil, then the resulting mixture was extracted with ethyl acetate. The combined extracts were washed with aqueous NaHCO₃, then with water, and dried over Na₂SO₄. The reaction mixture (3.15 g) was purified by flash chromatography (SiO₂). The column was eluted first with 15% ethyl acetate/hexanes (2 liters), then with ethyl acetate. The product 2.9 g (80%) was recrystallized from ethyl acetate to provide a compound of formula 7D above, m.p. 134°–135° C.

EXAMPLE 8

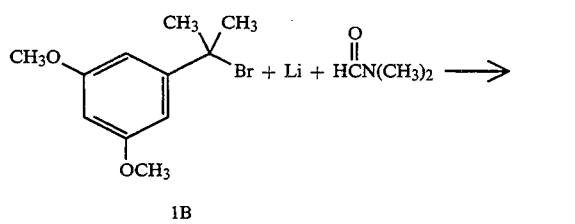

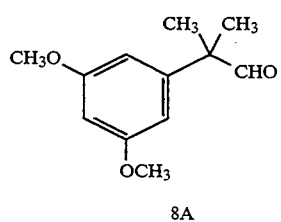

A. To a suspension of 92.5 mg of lithium dispersion (prewashed with hexane) in 1 ml of dry THF was added a solution of 0.259 g of the compound of formula 1B above and 64.5 μl of dry DMF in 1 ml of dry THF over 17 minutes at −20° C. The resulting mixture was then stirred for 1 hour more at −15° C., then it was quenched with aqueous saturated ammonium chloride solution. The resulting solution was extracted with ethyl ether. The ether extracts were washed with brine, dried over MgSO₄ and concentrated. The residue was purified by preparative thin layer chromatography (CH₂Cl₂) to give 0.142 g (82% yield) of the product of formula 8A above as an oil.

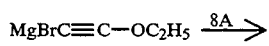

-continued

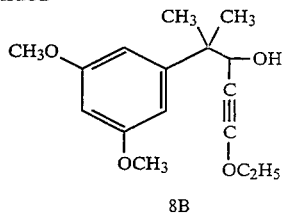

B. Ethoxyacetylene (77.4 μl) was added to a solution of 0.3 ml of ethyl magnesium bromide (3M) in 2 ml of dry THF at room temperature. The resulting solution was stirred for 1 hour 15 minutes, then 0.123 g of the compound of formula 8A above was added by syringe. After 1 hour of stirring at room temperature, the resulting mixture was quenched by ice water and extracted with ethyl acetate. The organic layer was separated, dried over MgSO₄ and concentrated. The residue was purified by preparative thin layer chromatography (5% ether in CH₂Cl₂) to give 0.13 g of product of formula 8B above (79% yield), which was used as such in step C below.

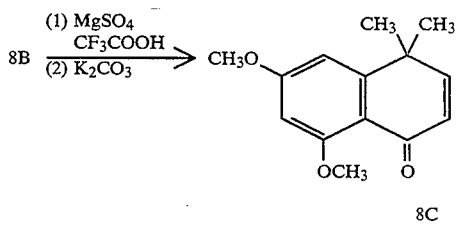

C. To a solution of 0,105 g of the compound of formula 8B above in 3.5 ml of anhydrous methylene chloride was added 68 mg of anhydrous magnesium sulfate. The resulting mixture was then cooled to −78° C. and a solution of 116 μl of trifluoroacetic acid in 0.2 ml of dry methylene chloride was added by syringe. After 20 minutes of stirring at −78° C. the cooling bath was removed and the resulting mixture quenched right away with a solution of 417 mg of potassium carbonate in 4.5 ml of water. The two layers were separated. The aqueous layer was extracted with ether, the combined ether and methylene chloride solution were dried over MgSO₄ and concentrated. The residue was purified by preparative thin layer chromatography (10% ether in CH₂Cl₂) to give 79.0 mg (90% yield) of the desired product of formula 8C above, mass spectometry, m/e 232 (M+).

EXAMPLE 9

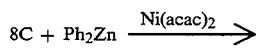

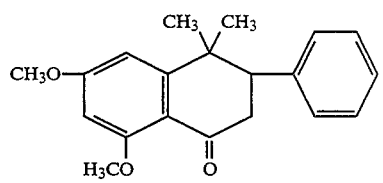

To a mixture of 0.24 ml of bromobenzene, 0.252 g of zinc bromide and 31 mg of lithium wire in 7 ml of anhydrous ether at 0° C. under nitrogen was sonicated for 1 hr 55 min (temperature of ultrasonic bath raised from 0° C. to 33° C.). The black mixture was cooled to 0° C., a solution of 0.13 g of compound 8C and 3.4 mg of Ni(acac)$_2$ in 3 ml of dry ether was added by cannula over 5 min. The reaction mixture was stirred for 20 min. at 0° C. and 25 min at room temperature then it was quenched by aqueous ammonium chloride solution. The resulting mixture was extracted with ethyl acetate, the combined organic extracts were washed with brine, dried over MgSO$_4$, and concentrated. The residue was purified by preparative TLC on silica gel (10% ether in CH$_2$Cl$_2$) to give 0.16 g (52% yield) of the desired product of formula 9A, mass spectrometry, m/e 310 (M+).

EXAMPLE 10

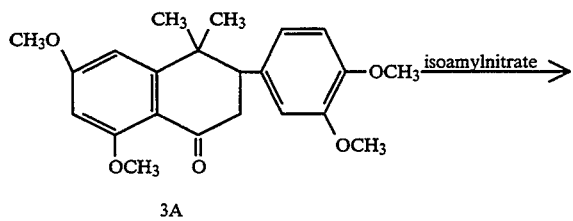

3A

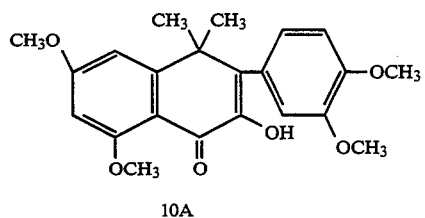

10A

The compound of formula 3A above (0.8) g was suspended and stirred for ten minutes in 70 ml of absolute C$_2$H$_5$OH and 4 ml of concentrated HCl. 4.0 ml of isoamylnitrate were added dropwise at room temperature over a period of ten minutes. The resulting solution was stirred at room temperature for 24 hours, then poured in water (400 ml). The aqueous mixture was extracted with CHCl$_3$ (total volume=600 ml). The combined extracts were washed with aqueous NaHCO$_3$, then with water and dried over anhydrous Na$_2$SO$_4$ for 24 hours. After filtration and evaporation of the solvent, the reaction mixture was purified by column chromatography (Merck silica gel, grade 60) (25% Hexanes/CHCl$_3$). The almost pure material (0.59 g) was further purified by preparative TLC using 40% ethyl ether/CHCl$_3$ as eluent and ethyl acetate:CH$_3$OH:CHCl$_3$ (1:1:1) for the extraction. The pure material (0.36 g) (43%) was recrystallized from CHCl$_3$/hexanes to provide the compound of formula 10A above, m.p.=161°-162° C.

EXAMPLE 11

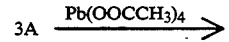

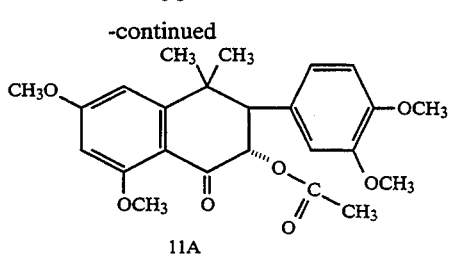

11A

The compound of formula 3A above (0.3 g, 0.81 mmoles) was dissolved in 10 ml of dry benzene in a dry flask provided with a dry reflux condenser. 0.72 g (1.62 mmoles) of Pb(OAc)$_4$ were added in three portions, each at three hour intervals. After each addition, the mixture was refluxed under N$_2$. After the last addition, the mixture was refluxed overnight, then 0.3 g more of Pb(OAc)$_4$ were added and refluxed for another four hours. After cooling to room temperature, the mixture was diluted with ethyl acetate, washed with water, then with saturated aqueous NaHCO$_3$, then again with water and dried over Na$_2$SO$_4$. The reaction mixture (0.35 g) was purified by flash chromatography (SiO$_2$) (55% ethyl acetate/hexanes) to yield 0.13 g (37%) of the compound of formula 11A above which was recrystallized from ethyl acetate, m.p. 202°-204° C.

EXAMPLE 12

3A + CH$_3$Li $\longrightarrow$

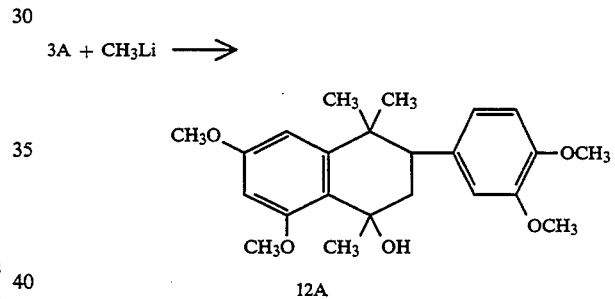

12A

To a solution of 1.27 ml of 1.6M methyllithium cooled in ice water bath was added a solution of 0.5 g of the compound of formula 3A above in 4 ml of anhydrous 1,4-dioxane over 10 minutes. The resulting light yellow solution was stirred for 1.5 hours at 0° C., then it was quenched with water. The resulting solution was extracted with ethyl acetate, dried over sodium sulfate and concentrated. The residue was purified by preparative TLC (silica gel was deactivated with triethylamine; eluting solvents 1:1 CH$_2$Cl$_2$/hexane) to give 0.150 g of the desired product of formula 12A (20% yield), mass spectrometry, m/e 386 (M+).

EXAMPLE 13

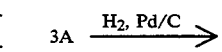

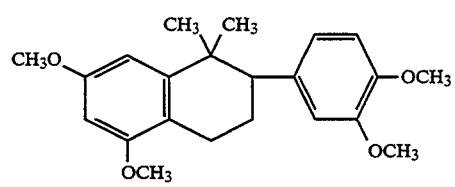

13A

To a solution of 2.1 g of a compound of formula 3A above in 20 ml of absolute C₂H₅OH and 30 ml of dry THF was added 0.4 g of Pd/C (10% Pd). The mixture was hydrogenated at room temperature with vigorous stirring for 20 hours, then it was filtered through a pad of Celite. The filtrate was concentrated to give 2.1 g of product, which was purified by flash chromatography ( solvent: 2:1 CH₂Cl₂/hexane, 4:1 CH₂Cl₂/hexane ) to give 1.825 g of desired product of formula 13A above (90% yield), mass spectrometry, m/e 356 (M+).

EXAMPLE 14

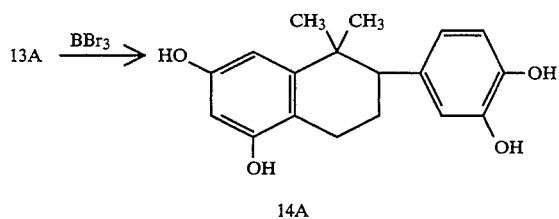

14A

To a stirred solution of 0.8 g of the compound of formula 13A above in 2 ml of dry CH₂Cl₂ was added 18 ml of 1N BBr₃ solution in CH₂Cl₂ over 10 minutes at −78° C. under N₂. The resulting solution was stirred for another 10 minutes at −78° C., then the cooling bath was removed and the mixture was stirred at room temperature for 48 hours. The solvent was evaporated under vacuum, the residue was cooled in an ice water bath, ice cold 3N NaOH solution was added slowly until the pH of the solution was 9-10. The resulting homogeneous solution was acidified to pH 4 by addition of cold 1N HCl. Ethyl acetate was added. The reaction mixture was shaken and separated. The organic solution was collected, washed with brine, dried over MgSO₄ and concentrated. The crude product was purified by flash chromatography on SiO₂ (2:1 CH₂Cl₂/ethyl acetate) and gave 0.570 g of pure product (85% yield), which was recrystallized from acetone giving the compound of formula 14A above, mass spectometry, m/e 300 (M+).

By substituting as a starting material the compounds listed in the first column of Table 3 below for compound 13A above and employing basically the same procedure as in Example 14, the compounds listed in the second column of Table 6 were prepared.

TABLE 6

| Starting Material | Product of Invention | Product m.p. °C. |
|---|---|---|
| [structure, CH₃O, OCH₃, OCH₃, OCH₃] | [structure 14B, HO, OH, OH, OH] | 135-140° (decomposed) |
| [structure, CH₃O, OCH₃, OCH₃, OCH₃] | [structure 14C, HO, OH, OH, OH] c) | 276-277° |
| [structure, CH₃O, OCH₃, OCH₃, OCH₃] | [structure 14D, HO, OH, OH, OH] | 227-229° |
| [structure, CH₃O, OCH₃, OCH₃, OCH₃] | [structure 14E, HO, OH, OH, OH, OH] | 300° |
| [structure, CH₃O, OCH₃, OCH₃, OCH₃] | [structure 14F, CH₃O, OH, OCH₃, OCH₃] a) | 209-210° |

TABLE 6-continued

| Starting Material | Product of Invention | Product m.p. °C. |
|---|---|---|
| (structure with CH₃O, OCH₃ groups, dimethyl naphthalenone with OCH₃, OCH₃ phenyl) | (structure 14G: with OH, OH groups) b) | 252-253° |
| (structure with CH₃O, OCH₃; phenyl with OCH₃, OCH₃) | (structure 14H: HO, OH; phenyl with OH, OH) | 313* |
| (saturated analog with CH₃O, OCH₃; phenyl with OCH₃, OCH₃) | (structure 14I: HO, OH; phenyl with OH, OH) | 315* |
| (structure with CH₃O, OCH₃, CH₃ on ring; phenyl with OCH₃, OCH₃) | (structure 14J: HO, OH, CH₃; phenyl with OH, OH) | 327* |

*MS: mass spectrometry, m/e (M + 1).
ᵃUsing BCl₃ instead of BBr₃.
ᵇReaction time 2 hours.
ᶜReaction mixture purified by C₁₈-Reverse Phase-HPLC [CH₃CN:H₂O:HCOOH (50:50:1)] as mobile phase.

EXAMPLE 15

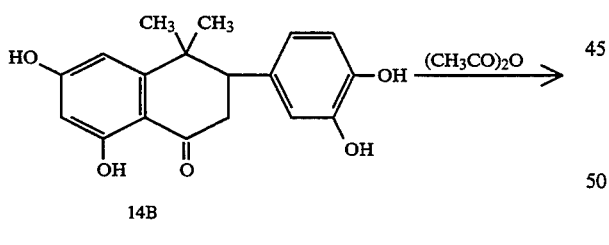

14B

The compound of formula 14B above ( 0.7 ) g was stirred at room temperature with 5 ml of pyridine and 2 ml of acetic anhydride. After two days, the solvents were vacuumed off using high vacuum. The residue was purified using flash chromatography (SiO₂) (40% ethyl acetate/hexanes) to yield 0.7 g (65%) of the compound of formula 15A above as a white solid which was characterized by mass spectrometry, m/e 482 (M+).

Basically the same procedure was used to prepare 3-(3,4-diacetyloxyphenyl)-6,8-diacetyloxy-4,4-dimethyl-1(4H)-naphthalenone.

EXAMPLE 16

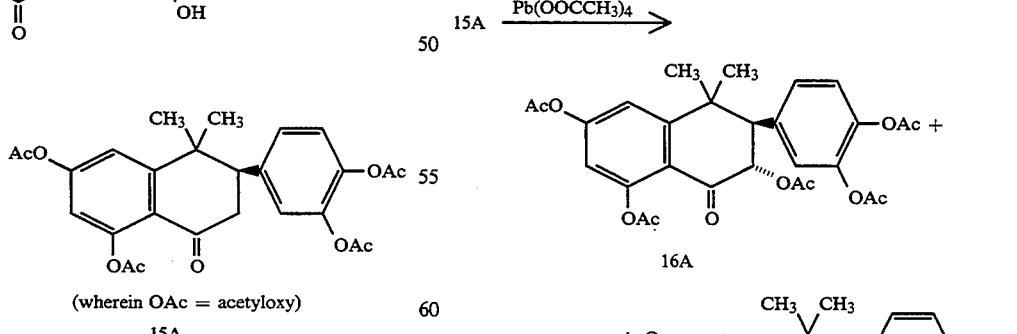

(wherein OAc = acetyloxy)
15A

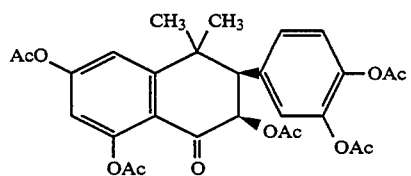

A mixture of Pb(OAc)$_4$ (0.7 g) and the compound of formula 15A above (0.6 g) was refluxed under N$_2$ in dry benzene (6 ml) in a dry apparatus. After 16 hours, the mixture was cooled to room temperature, 0.7 g of Pb(OAc)$_4$ was added and the mixture refluxed again for 24 hours. Three more additions of Pb(OAc)$_4$ at 12 hour intervals were made. After cooling to room temperature, the mixture was diluted with ethyl acetate (350 ml), washed with water and dried over Na$_2$SO$_4$. Purification of the mixture by flash chromatography (SiO$_2$, 35% ethyl acetate/hexanes) yielded 0.26 g (38%) of a racemic mixture of the compound of formula 16A above (which is the 2α, 3β compound), m.p. 202°–204° C., and 60 mg (9%) of a racemic mixture of a compound of formula 16B above (which is the 2β, 3β compound), m.p. 92°–95° C.

EXAMPLE 17

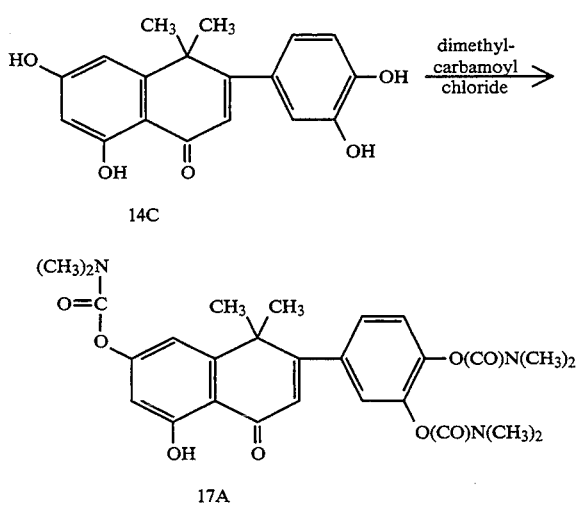

14C

17A

Dimethylcarbamoyl chloride (0.81 ml, 8.8 mmoles) was added to a dry pyridine (1.1 ml, 14 mmoles) solution of the compound of formula 14C above (0.5 g, 1.6 mmoles) in a dry apparatus. The thick solution was heated at 40°–42° C. under N$_2$ overnight. After cooling to room temperature the thick mixture was transferred into a beaker containing ice and 18 ml in 1N aqueous HCl. The precipitate formed was extracted in ethyl acetate (180 ml). The combined extracts were washed with water and dried. Purification by flash chromatography (SiO$_2$) (ethyl acetate) yielded 0.48 g (57%) of the compound of formula 17A, mass spectrometry, m/e 526 (M+1).

EXAMPLE 18

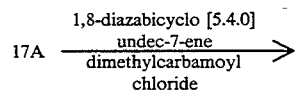

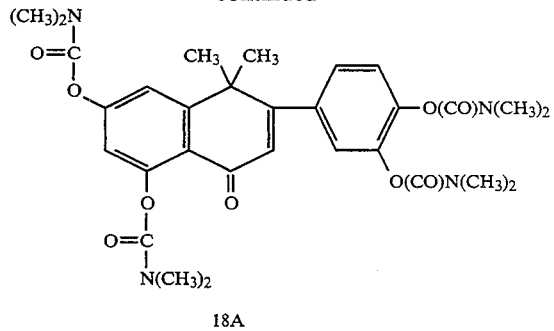

18A 1,8-Diazatricyclo[5,4,0]undec-7-ene (0.15 ml) were added at room temperature to the compound of formula 17A above (0.322 g, 0.61 mmoles) and 0.085 ml (0.92 mmoles) of dimethylcarbamoyl chloride. After stirring overnight under N$_2$ at room temperature, the thick paste was treated with cold 1N aqueous HCl. The precipitate formed was extracted into ethyl acetate. The ethyl acetate solution was washed with water and dried over Na$_2$SO$_4$. Purification by flash chromatography (SiO$_2$) (ethyl acetate) yielded 0.251 g (68%) of the compound of formula 18A above, mass spectrophotometry, m/e 597 (M+1).

EXAMPLE 19

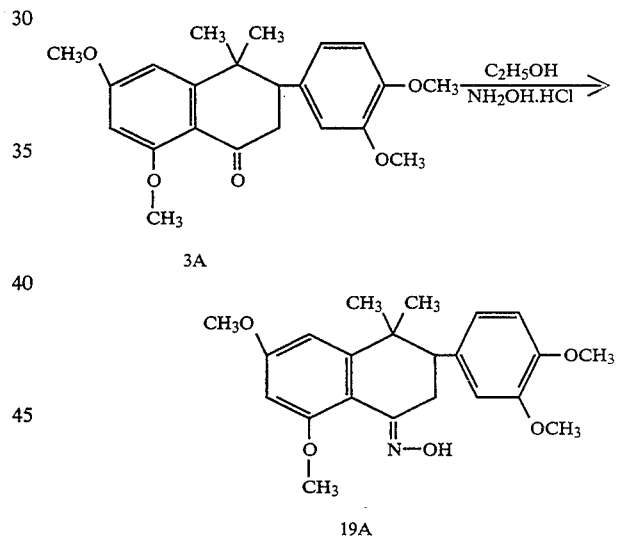

3A

19A

A mixture of 2.0 g of the compound of formula 3A above, 0.564 g of hydroxylamine hydrochloride, and 0.732 g of anhydrous sodium acetate in 20 ml of absolute ethanol or n—butanol was refluxed for about 24 hours. After cooling, the reaction mixture was filtered, the precipitate was washed with ethyl ether and dried under vacuum to give 2 g (98%) of the compound of formula 19A above, mass spectrometry, m/e 386 (M+1).

The following compounds in Table 7 are prepared by employing basically the same procedure as described in Example 19, by either substituting of NH$_2$OH to NH$_2$R, or substituting of a starting material for compound 3A above.

TABLE 7

| Starting Material | NH₂R | MOAc | Product of Invention | Mass Spectrometry m/e (M⁺) |
|---|---|---|---|---|
| 3A | NH₂NH₂·H₂O | without MOAc | 19B | 384 |
| 3A | NH₂—NH—C(=O)—CH₃ | M = H | 19C | 426 |
| 3A | NH₂—NH—C(=O)—NH₂·HCl | M = Na | 19D | 428 (M + 1) |
| 3A | NH₂—NH—C(=O)—C₆H₄(OH) | M = H | 19E | 504 |

TABLE 7-continued

| Starting Material | NH₂R | MOAc | Product of Invention | Mass Spectrometry m/e (M⁺) |
|---|---|---|---|---|
| 3A | NH₂—NH—C(=O)—C₆H₅ | M = Na | 19F | 488 |
| 3A | NH₂—OMe·HCl | M = Na | 19G | 399 |
| | NH₂OH·HCl | M = Na | 19H | 383 |
| | NH₂OH·HCl | M = Na | 19I | 372 (M + 1) |

TABLE 7-continued

| Starting Material | NH₂R | MOAc | Product of Invention | Mass Spectrometry m/e (M⁺) |
|---|---|---|---|---|
| (structure) | NH₂OH.HCl | M = Na | 19J | 400 |
| (structure) | NH₂OH.HCl | M = Na | 19B | 330 (M + 1) |
| (structure) | NH₂OH.HCl | M = Na | 19K | |
| | | | 19L | 400 (M + 1) |

EXAMPLE 20

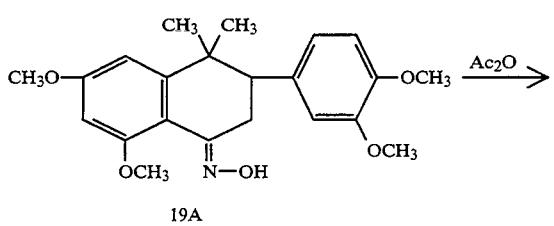

19A

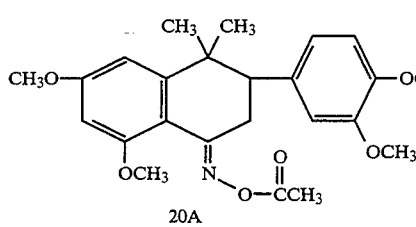

20A

To a mixture of 0.193 g of a compound of formula 19A above in 0.5 ml of anhydrous pyridine was added 71 μl of acetic anhydride at 0° C. After few minutes of stirring, the cooling bath was removed, and the reaction mixture was stirred at room temperature for overnight (18 h). The mixture was diluted with methylene chloride and then extracted with cold 1N HCl solution. The organic layer was separated and then washed with water, brine, dried over anhydrous MgSO4, and concentrated to give 0.156 g (73% yield) of product of formula 20A above, mass spectrometry, m/e 428 (M+1).

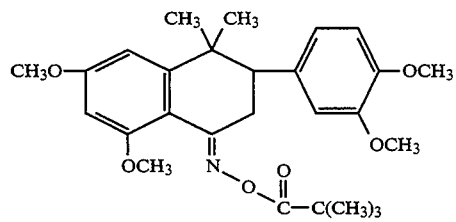

20B

By substitution of acetic anhydride with trimethyl acetyl chloride, a compound of formula 20B above can be prepared according to the same procedure for the conversion of a compound 19A to 20A.

EXAMPLE 21

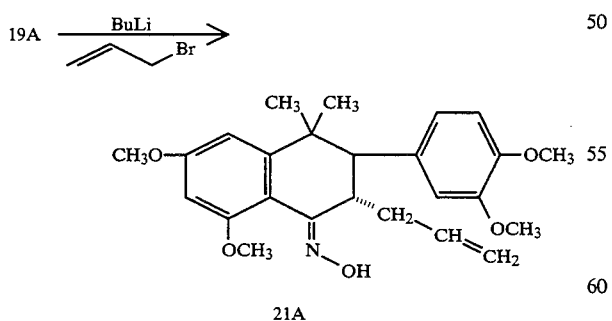

21A

One half of 1.5 ml of n—BuLi (2.5M solution in Hexanes) was added slowly dropwise under N2 to a precooled (−78° C.) suspension of a compound of formula 19A above (0.5 g; 1.3 mmoles) in 3.0 ml of dry THF. After the addition, the dry ice-acetone bath was replaced with an ice bath and the mixture was let warm up to 0° C. The second half of the n—BuLi was then added also dropwise. After the addition, the solution was cooled back to −78° C. and 0.15 ml of allyl bromide was added dropwise. The cooling bath was removed and the solution was let warm up and stirred at room temperature for one hour. After adding water, the solution was diluted with CH2Cl2, washed with water, and dried (Na2SO4). The reaction mixture was purified by flash chromatography (SiO2) (30% EtOAc/Hexanes) yielding 370 mg (67%) of product of formula 21A, mass spectrometry, m/e 426 (M+1).

EXAMPLE 22

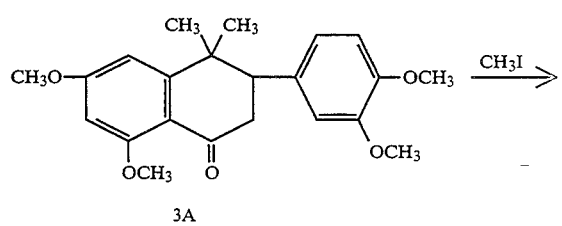

3A

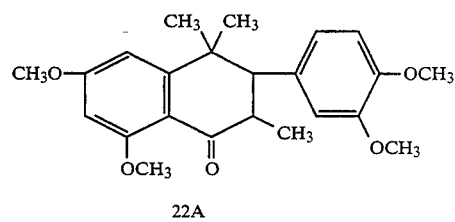

22A

A compound of formula 3A (3.7 g) dissolved in dry THF:CH2Cl2 (1:1) (60 ml) was added slowly dropwise under N2 to a precooled (−78° C.) 1.0 Molar THF solution of lithium bis(trimethylsilyl)amide (15 ml). After the addition, which lasted 90 minutes, the solution was stirred at −78° C. for two hours, then 2.0 ml of CH3I were added in one portion. The solution was let warm up and stirred at room temperature overnight. After cooling in ice bath, the reaction was quenched by careful addition of water. The organic layer was separated. The aqueous layer was extracted several times with CH2Cl2. The combined CH2Cl2 solutions were washed with water and dried (Na2SO4). The reaction mixture was purified by flash chromatography (SiO2) (30% EtOAc/Hexanes).

The product was recrystallized from EtOAc/Hexanes yielding 2.0 g of compound (52%) of formula 22A.

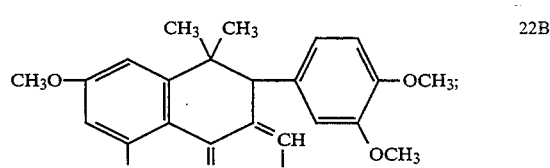

22B

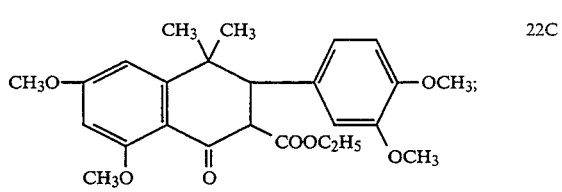

22C

-continued

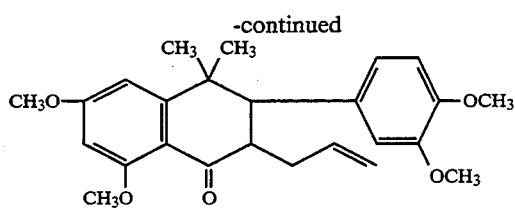

22D

Using the same procedure, by reaction of the same starting material of formula 3A with ethyl formate, ethyl chloroformate and allyl bromide gave a product of formula 22B (50% yield), 22C (18% yield) and 22D (58%) individually. Mass spectrometry of 22B, m/e 398 (M+); 22C, m/e 442 (M+); 22C m/e 410 (M+).

EXAMPLE 23

22A $\xrightarrow{DDQ}$

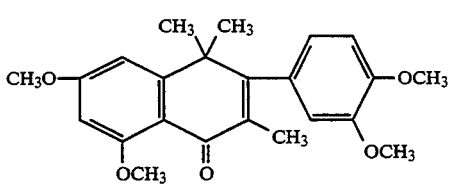

23A

A compound of formula 22A (2.0 g; 5.2 mmole) was dissolved at 45° C. in dry benzene (400 ml) in a dry apparatus. The solution was then cooled to room temperature and 2,3-dichloro-5,6-dicyano-1,4-benzoquinone (DDQ) (1.6 g) was added in one portion. The mixture was then heated at 85°–90° C. under $N_2$ for 24 hours. After cooling to room temperature, the solid was filtered through "Celite". The "Celite" was washed with $CH_2Cl_2$. The reaction mixture was partially purified by flash chromatography (35% EtOAc/Hexanes) (SiO$_2$). Another purification as before (SiO$_2$) (50% EtOAc/Hexanes) gave the product of formula 23A which was recrystallized from EtOAc/Hexanes (1.8 g) (94%), m.p. 183°–186° C.

EXAMPLE 24

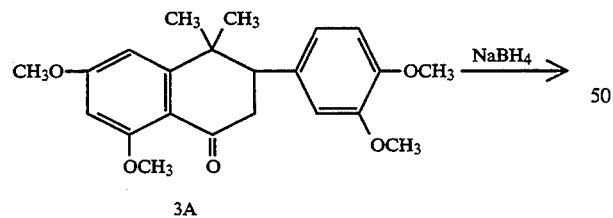

3A $\xrightarrow{NaBH_4}$

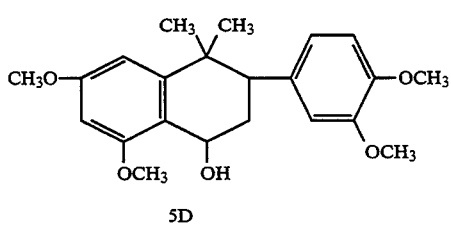

5D

A. NaBH$_4$ (0.4; 10.6 mmoles) was added in one portion to a suspension of a compound of formula 3A (1.4 g; 3.8 mmoles) in 50 ml of absolute EtOH and 5 ml of dry THF. The mixture was then heated under $N_2$ for 5 hours at 60° C. The solution was then poured in ice water. The resulting white solid was extracted with EtOAc. The combined extracts were washed with water and dried (Na$_2$SO$_4$). The reaction mixture was purified by flash chromatography (SiO$_2$) (50% EtOAc/Hexanes). The product of formula 5D was recrystallized from EtOAc/Hexanes (1.12 g) (80%).

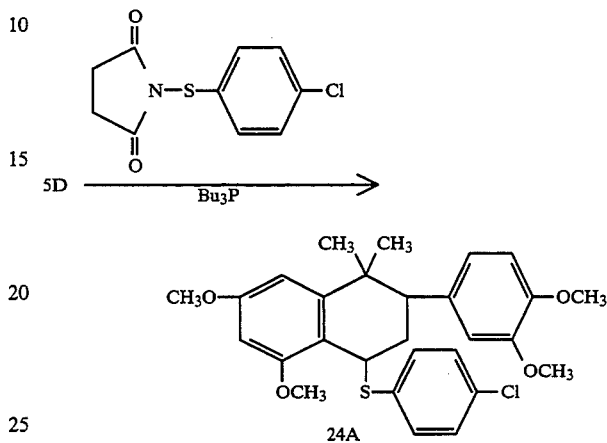

5D $\xrightarrow{Bu_3P}$

24A

B. N-(4-chlorophenylthio) succinimide (0.582 g) was added under $N_2$ in one portion to a solution of n—Bu$_3$p (0.6 ml) in dry benzene (4.0 ml). After stirring for ten minutes at room temperature, a compound of formula 5D (0.4 g) was added. The solution was stirred at room temperature for two days, then water was added. The organic layer was diluted with EtOAc, washed with water and dried (Na$_2$SO$_4$). The reaction mixture is purified twice by flash chromatography (SiO$_2$) (15% EtOAc/Hexanes) yielding 0.148 g (28%) of product of formula 24A, mass spectrometry, m/e 499 (M+).

EXAMPLE 25

3A $\xrightarrow{HC(OCH_3)_3}$

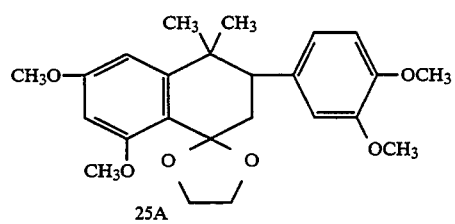

25A

A mixture of p-toluene sulfonic acid (5 mg), ethylene glycol (0.26 ml), a compound of formula 3A (0.374 g; 1.0 mmole), and trimethyl ortoformate (0.53 ml) in dry benzene (1.3 ml) was heated at a bath temperature of 35°–40° C. in a dry apparatus consisting of a two necked flask with a Liebig condenser. A 14 mmHg vacuum was applied while heating. After 90 minutes, the bath temperature was raised to 80°–85° C.

After two hours at that temperature, the resulting solid was cooled to room temperature and dissolved in EtOAc. The solution was washed first with saturated aqueous NaHCO$_3$, then with water and dried (Na$_2$SO$_4$). The reaction mixture was purified by flash chromatography (SiO$_2$) (5%, 30%, 50% gradient CH$_2$Cl$_2$/Hexanes).

The product was recrystallized from EtOAc/Hexanes yielding 0.27 g (65%) of compound of formula 25A, m.p. 173°–174° C.

EXAMPLE 26

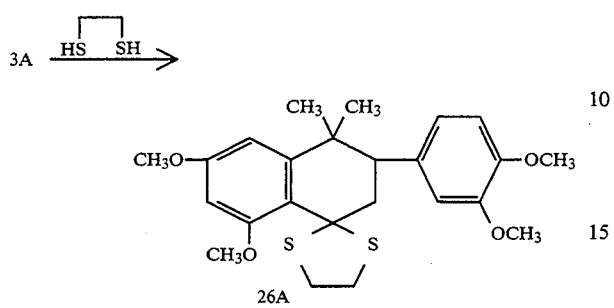

To a solution of a compound of formula 3A (0.2 g) in 2.2 ml of dry methylene chloride was added 68 μl of 1,2-ethanedithiol and 30 μl of borontrifluoride ethelate. The yellow solution was stirred at room temperature for overnight, a solution of 34 μl of 1,2-ethanedithol and 15 μl of borontrifluoride etherate was added. After 2 h of stirring, the reaction mixture was quenched by 2 ml of 5% MaOH solution. The organic layer was separated, washed with water, brine, dried over MgSO4 and concentrated. The residue was crystallized from CH2Cl2/hexane to give a product of formula 26A (0.2 g; 83%), mass spectrometry, m/e 466 (M+).

EXAMPLE 27

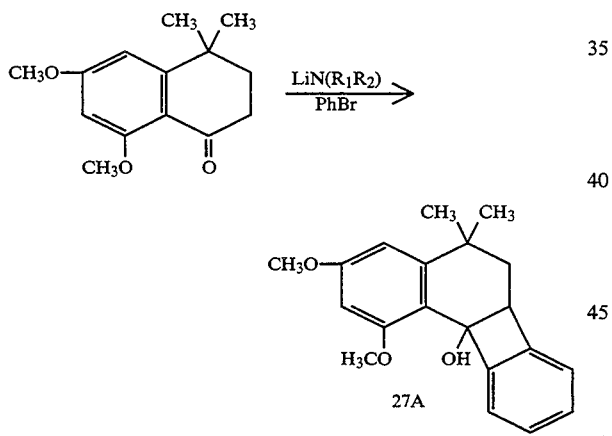

A. To a solution of 2.14 ml of N-isopropyl-N-cycylhexylamine in 18 ml of anhydrous THF was added 5.16 ml of 2.5N of n—butyllithium at −78° C. The resulting solution was stirred at −25° C. for ½ h, then recooled to −78° C. A solution of 0.702 g of a compound of formula 27 (prepared by hydrogenation of a compound of formula 8C according to the procedure in Example 13) in 12 ml of anhydrous THF was added dropwisely. The reaction mixture was stirred at −78° C. for 1 h, then the reaction temperature was allowed to warm to −25° C. A solution of 0.853 ml of bromobenzene in 5 ml of anhydrous THF was added over 5 min, the reaction mixture was stirred at ambient temperature (−25° ~r.t.) for 24 h, then it was quenched by aqueous saturated NH4Cl solution. After extraction with ethyl acetate, the organic extracts were washed with cold 10% HCl solution, then washed with brine, dried over anhydrous MgSO4, and concentrated. The residue was purified by preparative TLC (CH2Cl2) to give 0.58 g (62%) of a product of formula 27A, mass spectrometry m/e 311 (M+1).

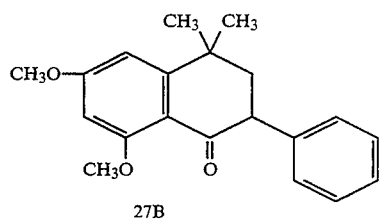

B. To a solution of 0.38 g of a compound of formula 27A in 9 ml of 2:1 dimethoxyethane/diisopropylamine was added 0.24 g of sodium amide at room temperature under N2. The mixture was stirred for 20 min at 25° C. and 2 hr at 80° C. After cooling to 0° C., the reaction mixture was quenched by ice water, acidified by ice cold 2N HCl, extracted with methylene chloride. The organic layer was washed with saturated NaHCO3, dried over anhydrous MgSO4 and concentrated. The residue was recrystallized from CH2Cl2/hexane to give 0.32 g (85%) of product of formula 27B, mass spectrometry m/e 310 (M+).

EXAMPLE 28

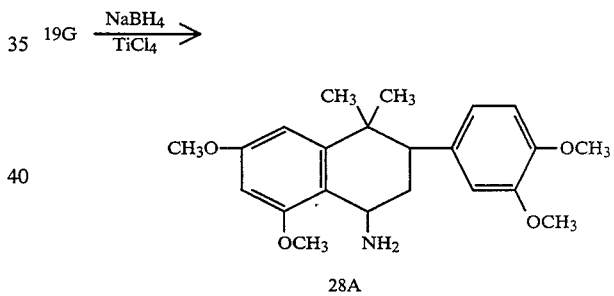

A. To a mixture of 0.199 g of sodium borohydride in 5 ml of anhydrous DMF was added under nitrogen 2.63 ml of 1M TiCl4 solution at 0° C. After 10 min of stirring, a solution of 0.5 g of methoxime of formula 19G in 5 ml of anhydrous DME was added dropwisely, the resulting mixture was stirred for 25 min at 0° C. and for 3 h at room temperature. Ice water was added to quench the reaction, ethyl ether with extraction was used to remove the nonpolar material. The acidic aqueous solution was cooled and basified by 1N NaOH solution at 0° C. to pH 10, then it was extracted with EtOAC/CH2Cl2. The combined organic extracts were dried over anhydrous K2CO3, evaporated. The residue was purified by preparative TLC (5% ether in CH2Cl2; SiO2 deactivated with triethylamine) to give 0.335 g (72%) of a product of formula 28A, mass spectrometry m/e 372 (M+1).

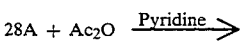

-continued

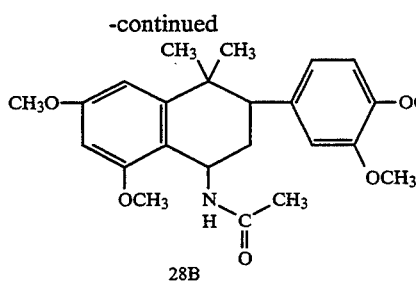
28B

B. To a solution of 0.235 g of compound 28A in 0.7 ml of dry pyridine was added 71 μl of acetic anhydride at 0° C. After ½ hour of stirring, the cooling bath was removed, the reaction mixture was stirred for 4 h at room temperature, then 100 μl of triethylamine were added, and continued stirring for another 2 hours. The mixture was diluted with $CH_2Cl_2$ and extracted three times with cold 1N HCl solution. The organic layer was washed with water, brine, dried and concentrated. The residue was purified by flash chromatography on $SiO_2$ ($CH_2Cl_2$ as eluting solvent; the polarity was increased gradually to 10% ether in $CH_2Cl_2$) to give 0.15 g (57%) of product of formula 28B, which was recrystallized from $CH_2Cl_2$/hexane. Mass spectrometry m/e 413 ($M^+$).

EXAMPLE 29

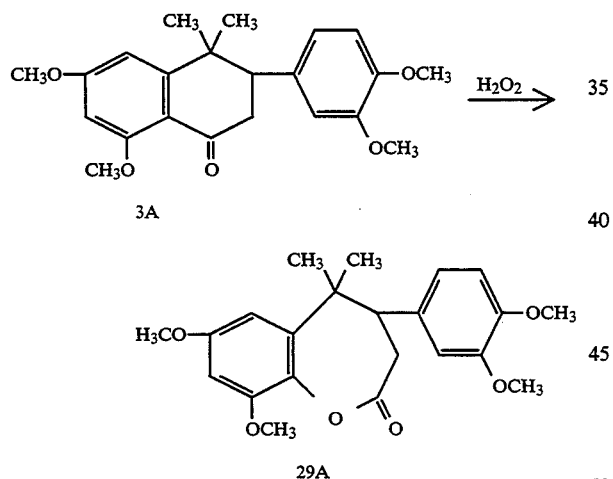

A compound of formula 3A (1.0 g; 2.7 mmoles) was stirred at room temperature in 8.0 ml of glacial acetic acid and 1.5 ml (13.0 mmoles) of 30% aqueous $H_2O_2$. After twenty hours, the solution was poured in water and the solid formed was extracted with $CH_2Cl_2$. The combined extracts were washed with water and dried ($Na_2SO_4$). The reaction mixture was purified by flash chromatography. (20% EtOAc/Hexanes). The product 29A was recrystallized from EtOAc/Hexanes. Yield: 0.64 g (61%) (m.p.=168°–169° C.).

Using the same procedure 0.66 g of 3-(3,4-dimethoxyphenyl)-6,8-dimethoxy-2,4,4-trimethyl-dihydro-1(4H)-naphthalenone gave 0.28 g (41%) of 4-(3,4-dimethoxyphenyl)-4,5-dihydro-7,9-dimethoxy-3,5,5-trimethyl-1-benzoxepin-2(3H)-one (m.p.=163°–165° C.) (EtOAc/Hexanes).

EXAMPLE 30

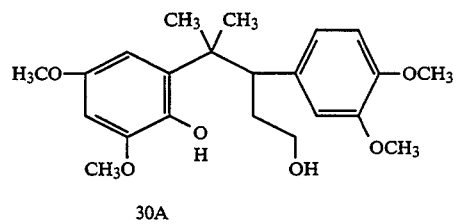
30A

A. A dry THF (30 ml) solution of compound of formula 29A (1.5 g; 3.9 mmoles) was added under $N_2$ to a precooled (ice bath) slurry of $LiAlH_4$ (222 mg; 5.8 mmoles) in dry THF (3.0 ml). After the addition, the mixture was stirred in ice bath for two hours, then the reaction was quenched by careful addition of saturated aqueous $NH_4Cl$. The organic layer was filtered. The slurry was washed several times with EtOAc. The combined washings were washed with water and dried ($Na_2SO_4$). The reaction mixture was purified by flash chromatography yielding 1.35 g (89%) of product of formula 30A

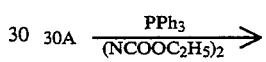

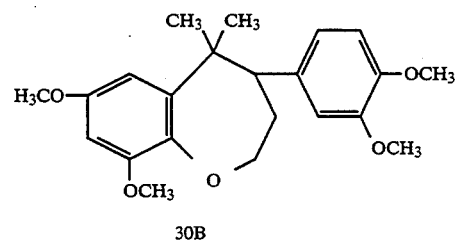
30B

B. Diethyl azodicarboxylate (0.36 ml; 2.29 mmoles) was added in small volumes over a period of 45 minutes under $N_2$ to a dry THF (10 ml) solution of $(C_6H_5)_3P$ (0.58 g; 2.21 mmoles) and a compound of formula 30A (0.72 g; 1.84 mmoles). After the addition, the solution was stirred for one hour, then the solvent was evaporated under reduced pressure. The reaction mixture was purified by flash chromatography (20% EtOAc/Hexanes) ($SiO_2$) yielding 0.57 g (83%) of product of formula 30B.

EXAMPLE 31

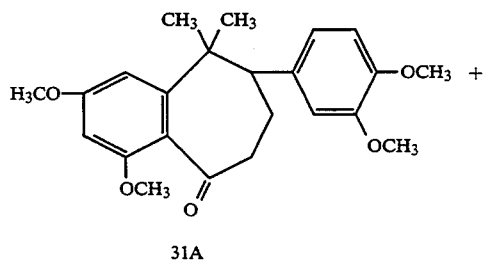
31A

-continued

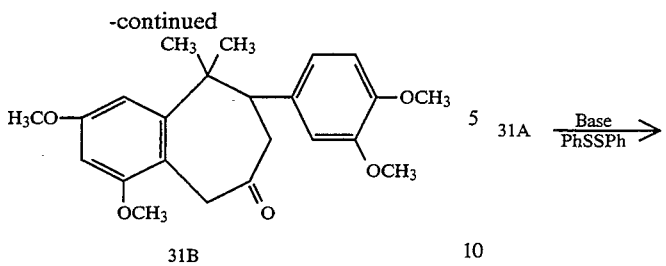

31B

BF$_3$.Et$_2$O (6.72 ml) was added via addition funnel over 30 minutes under N$_2$ to a precooled (−78° C.) dry CH$_2$Cl$_2$ (70 ml) solution of a compound of formula 3A (13.5 g). After the addition, the solution was stirred at −78° C. for one hour, then 50 ml of a CH$_2$Cl$_2$ solution of (CH$_3$)$_3$SiCHN$_2$ (10% W/W) was added over a period of 1½ hours dropwise. The solution was stirred at that temperature for 2½ hours, the cooling bath was then removed, and the reaction was quenched by slow addition of water. The mixture was stirred at room temperature for 1½ hour, then the aqueous layer was separated. The organic layer was diluted with CH$_2$Cl$_2$ (400 ml), washed with water, and dried (Na$_2$SO$_4$). The reaction mixture was purified by flash chromatography (SiO$_2$) (20% EtOAc/Hexanes). The less polar product on SiO$_2$ TLC (35% EtOAc/Hexanes) was identified as compound of formula 31B (1.5 g) (10.7%).

The more polar product was recrystallized from EtOAc/hexanes and was found to be compound of formula 31A (48%) (m.p.=144°-146 ° C.).

Using the same procedure:
(i) 3-(3,5-dimethoxyphenyl)-6,8-dimethoxy-4,4-dimethyl-3,4-dihydro-1(2H)-naphthalenone gave 8-(3,5-dimethoxyphenyl)-6,7,8,9 -tetradydro-2,4-dimethoxy-9,9-dimethyl-5H-benzocyclohepten-5-one (44%) and 8-(3,5-dimethoxyphenyl)-5,7,8,9-tetrahydro-2,4-dimethoxy-9,9-dimethyl-6H-benzocyclohepten-6-one;
(ii) 3,4-dihydro-3-(3,4-dimethoxyphenyl)-4,4-dimethyl-8-methoxy-1(2H)-naphthalenone gave 8-(3,4-dimethoxyphenyl)-9,9-dimethyl-4-methoxy-6,7,8,9-tetrahydro-5H-benzo-cyclohepten-5-one (45%) and 8-(3,4-dimethoxyphenyl)-9,9-dimethyl-4-methoxy-5,7,8,9-tetrahydro-6H-benzocyclohepten-6-one (14%);
(iii) a compound of formula 27 (Example 27) gave 6,7,8,9-tetrahydro-2,4-dimethoxy-9,9-dimethyl-5H-benzocyclohepten-5-one (31C).

EXAMPLE 32

EXAMPLE 32

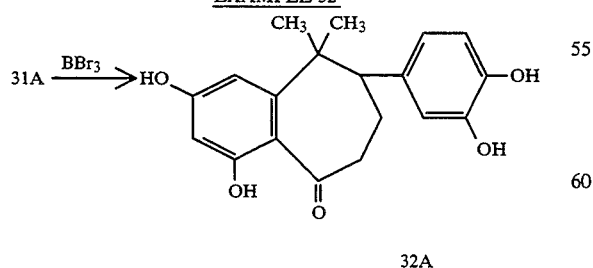

32A

The compound of 32A was prepared from the compound of formula 31A according to the procedure described in Example 14, yield 28%. Mass spectrometry m/e 329 (M+1).

EXAMPLE 33

EXAMPLE 33

31A $\xrightarrow[\text{PhSSPh}]{\text{Base}}$

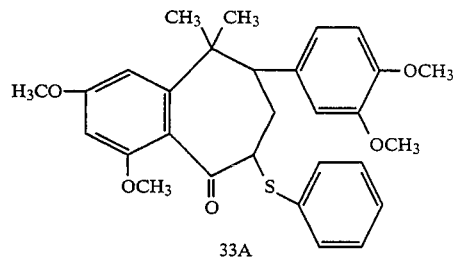

33A

A dry THF (1.8 ml) solution of the compound of formula 31A was added via syringe dropwise under N$_2$ to a precooled (−78° C.) 1M. THF solution of [(CH$_3$)$_3$Si]$_2$ NLi (2.4 ml; 2.4 mmoles). After the addition, the solution was stirred at −78° C. for three hours, then transferred via cannule into a dry THF (1.0 ml) solution of C$_6$H$_5$SSC$_6$H$_5$ (250 mg; 1.15 mmoles) at room temperature. After stirring for 20 hours at room temperature, two 0.2 g aliquots of C$_6$H$_5$SSC$_6$H$_5$ were added at four hours intervals. After the second aliquot, the solution was stirred for two hours, then diluted with EtOAc, washed first with 1N aqueous HCl, then with water, and dried (Na$_2$SO$_4$). The reaction mixture was purified by flash chromatography (SiO$_2$) (10% EtOAc/Hexanes). The product of formula 33A (0.4 g; 81%) was recrystallized from EtOAc/Hexanes (m.p. 194°-196° C.).

EXAMPLE 34

EXAMPLE 34

31A $\xrightarrow[\text{CH}_3\text{I}]{\text{Base}}$

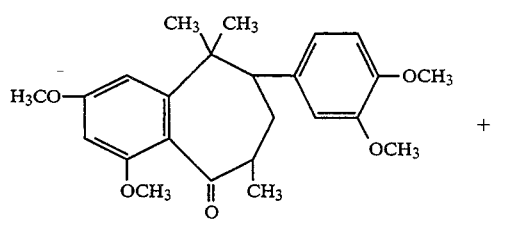

34A

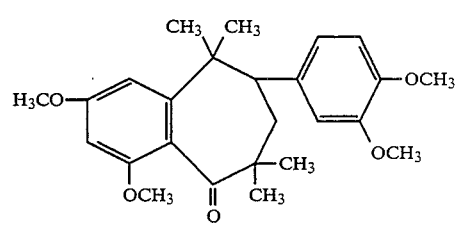

34B

Both compounds of formula 34A and 34B were prepared from the compound of formula 31A by using the same reagents and procedure detailed in Example 22.

The trimethyl compound of formula 34A (76%) was recrystallized from EtOAc/Hexanes (m.p.=146°-147° C.). The tetramethyl product of formula 34B was obtained in 8% yield from the same reaction. Mass spectrometry; m/e 413 (M+1).

EXAMPLE 35

EXAMPLE 35

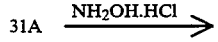

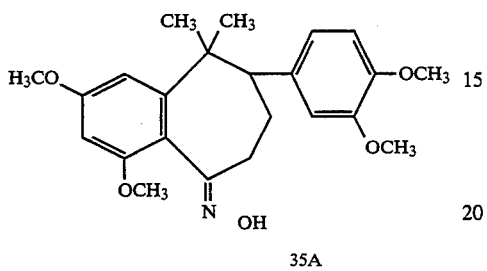

35A

The compound of formula 35A was obtained in 54% yield as a separable mixture of E and Z oximes, mass spectrometry m/e 400 (M+1), from the compound of formula 31A using the same reagents and procedure detailed in Example 19.

EXAMPLE 36

EXAMPLE 36

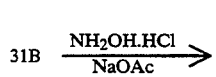

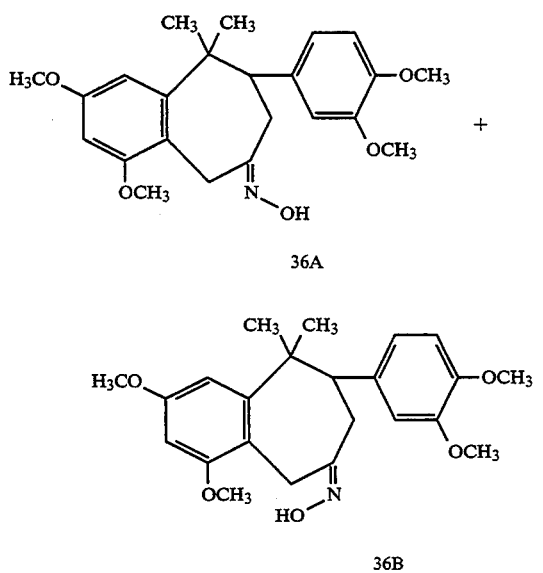

36A

+

36B

A mixture of the compound of formula 31B (800 mg), NH$_2$OH HCl (360 mg), and AcONa (600 mg) was stirred at room temperature for two hours in 3.0 ml of n—BuOH. The solvent was then removed using high vacuum. The residue was treated with water, taken in EtOAc, washed with water and dried (Na$_2$SO$_4$). The reaction mixture was purified by flash chromatography (SiO$_2$) (25% EtOAc/Hexanes) yielding the major oxime of formula 36B, (330 mg) (39%) (m/e=400) (M+1)$^+$, and the minor one. The letter was further purified by preparative TLC (SiO$_2$) (30% EtOAc/Hexanes) yielding 50 mg (6%) of oxime of formula 36A. Mass spectometry m/e 400 (M+1).

EXAMPLE 37

EXAMPLE 37

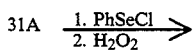

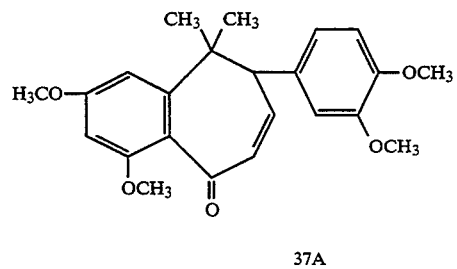

37A

C$_6$H$_5$SeCl (0.31 g; 1.6 mmoles) was added in small portions under N$_2$ over a period of 90 minutes to an EtOAc (9.0 ml) (predried over 3A° molecular sieves) solution of the compound of formula 31A (0.35 g; 0.91 mmoles). When the solution became yellow, it was washed with water (3×2.5 ml), then 1.4 ml of THF and 0.22 ml of 30% H$_2$O$_2$ were added in the order. The solution was then stirred for one hour, then diluted with EtOAc, washed with aqueous Na$_2$CO$_3$, then with water, and dried (Na$_2$SO$_4$). The reaction mixture was separated by flash chromatography (20% EtOAc/Hexanes). The fraction containing the desired product of formula 37A which was further purified by preparative TLC (2 elutions with 40% EtOAc/Hexanes). Yield: 75 mg (21%). Mass spectrometry m/e 383 (M+1).

EXAMPLE 38

EXAMPLE 38

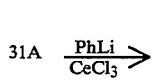

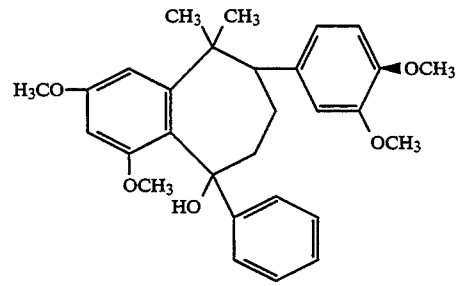

38A

A. CeCl$_3$ H$_2$O (480 mp) was dried in a two necked round bottom flask at 145° under high vacuum overnight. The solid was then cooled to room temperature and the flask was provided with rubber septa. Dry THF (4.0 ml) was added, the mixture was stirred at room temperature for two hours under N$_2$, then cooled to −78° C. Phenyllithium (1.2 ml) (2.0 Molar) was added dropwise and the mixture was stirred for 30 minutes. A THF (4.0 ml) solution of the compound of formula 31A (0.384 g; 1.0 mmoles) was added dropwise over a period of 10 minutes. After the addition, the mixture was stirred at −78° C. for four hours, then the reaction was quenched by addition of saturated aqueous NH₄Cl at −78° C. The cooling bath was removed and the mixture let warm up to room temperature. The solid was filtered through "Celite," washed with EtOAc, and the filtrate dried over Na₂SO₄. The reaction mixture was purified by preparative TLC (SiO₂) (35% EtOAc/Hexanes) yielding 0.2 g (43%) of product of formula 38A. Mass spectometry m/e 445 (M—H₂O+1).

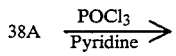

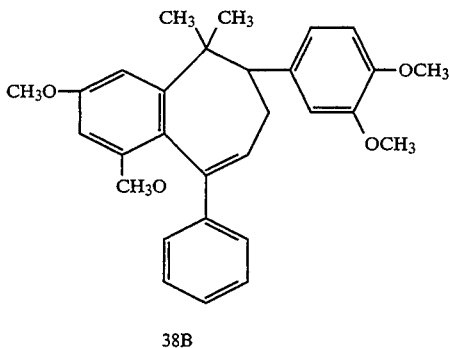

B. Dry Pyridine (1.0 ml) and POCl₃ (0.4 ml) were added in the order to a precooled (ice bath) dry benzene (3.0 ml) solution of the compound of formula 38A (0.11 g). The resulting mixture was stirred in ice bath for two hours, then the reaction was quenched with water. The mixture was extracted with CH₂Cl₂. The combined extract were washed with water and dried (Na₂SO₄). The reaction mixture was purified by preparative TLC (SiO₂) (20% EtOAc/Hexanes) yielding 86 mg (78%) of product of formula 38B. Mass spectrometry m/e 445 (M+1).

EXAMPLE 39

EXAMPLE 39

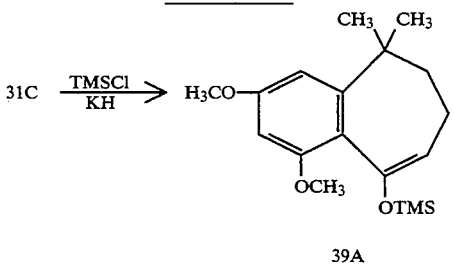

A. To a mixture of 0.55 g of potassium hydride in 3 mL of dry THF was added a solution of 0,992 g of the compound of formula 31C in 4 mL of dry THF. The resulting mixture was vigorously stirred for 1 hr at room temperature under nitrogen. After cooling to −78° C., a solution of 0.836 mL of dry triethylamine was added, followed by 0.71 mL of trimethylsilyl chloride. After 15 min. of stirring, the cooling bath was removed and the reaction was quenched by ice cold 0.1N HCl solution and 12 mL of methylene chloride. The mixture was shaked, the organic layer was separated and washed with aqueous NaHCO₃ solution. After drying over anhydrous sodium sulfate, the solution was concentrated to give 1.164 g of product of formula 39A (91% yield), which was used directly in the next step.

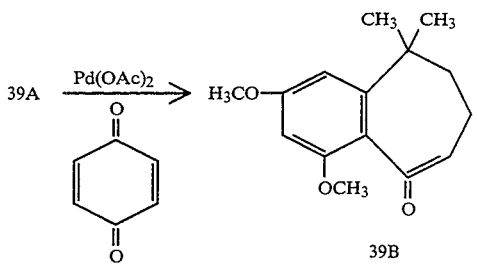

B. To a mixture of 0.449 g of palladium acetate and 0.216 g of 1,4-benzoquinone in 11 mL of anhydrous acetonitrile was added at room temperature a solution of 1.164 g of the compound of formula 39A in 3 ml of dry THF for over 5 min. The resulting solution was stirred for 4.5 hours then 0.449 g of palladium acetate were added. After 1.5 hours of stirring, the reaction mixture was quenched with water and then extracted with EtOAc. The organic layer was separated, dried over MgSO₄ and concentrated. The residue was purified by flash chromatography on SiO₂ (CH₂Cl₂) to give 0.6 g (61%) of a product of formula 39B.

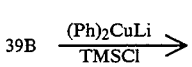

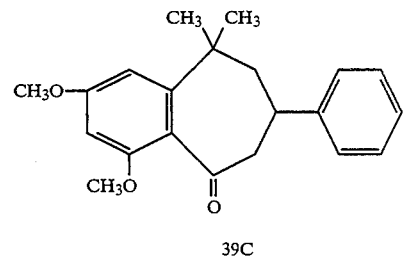

C. To a mixture of 0.229 g of copper (I) iodide in 3 mL of dry ether at −78° C. was added 1.4 mL of 1.7N phenyllithium. The resulting mixture was stirred at −30° for ½ h. then it was cooled to −78° C. TMSCl (0.152 mL) was added, followed by a solution of 0.246 g of the compound of formula 39B in 3 mL of 2:1 ether/THF (over 10 min.). The reaction mixture was stirred at −78° C. for 20 min. and at −25°-30° C. for 40 minutes. Then the cooling bath was removed, the mixture was stirred for 15 min., then the reaction was quenched with saturated NH₄Cl solution. The mixture was stirred till the aqueous layer turned to deep blue. The organic layer was separated, the aqueous layer was extracted with EtOAc. The combined organic solution was concentrated, and the residue was dissolved in 2 mL of THF and 0.5 mL of 1N HCl solution. The mixture was stirred at room temperature for 10 min., then it was neutralized with aqueous NaHCO₃ solution and extracted with EtOAc. The EtOAc extracts were dried over MgSO₄ and concentrated. The residue was purified by preparative TLC (CH₂Cl₂) to give 0.21 g (65%) of the product of formula 39C, mass Spectrometry m/e 324 (M⁺).

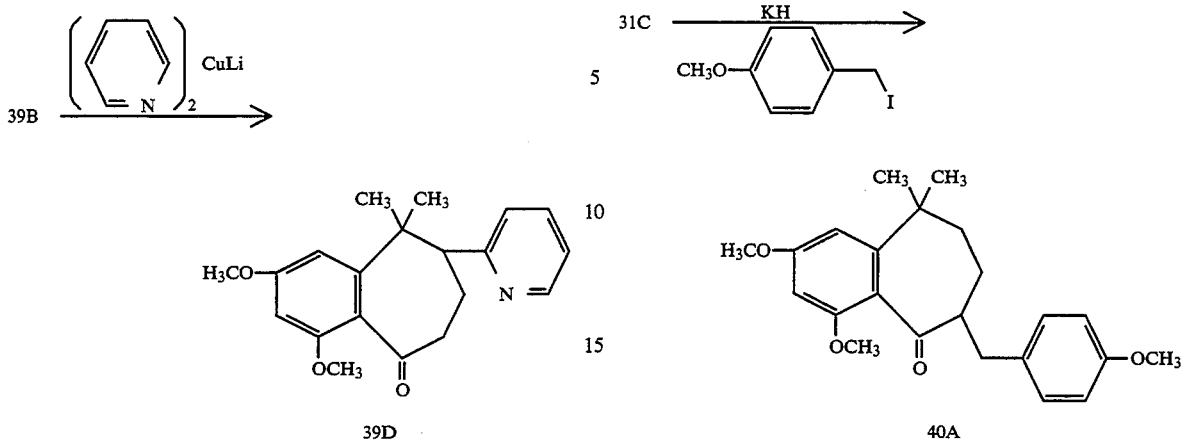

D. To a mixture of 0.248 g of copper (I) iodide in 0.191 mL of diethyl sulfide and 3 mL of dry ether was added 2-pyridyllithium (prepared by addition of 1.04 mL of 2.5N butyllithium to a solution of 0.248 mL of 2-bromopyridine in 2.5 mL of dry ether at −78° C.). After 20 min. of stirring at 0° C., a solution of 0.246 g of the compound of formula 39B in 1 mL of dry THF was added dropwisely. The reaction mixture was stirred for ½ hr. then a solution of NH$_4$OH/saturated NH$_4$Cl was added. The organic layer was separated, the aqueous layer was extracted with CH$_2$Cl$_2$ three times. The combined organic solutions were washed with brine, dried over anhydrous Na$_2$SO$_4$, and concentrated. The residue was purified by preparative TLC (33% ethyl ether in CH$_2$Cl$_2$) to give 0.145 g of the product of formula 39D, mass spectrometry m/e 326 (M$^{+1}$).

EXAMPLE 40

EXAMPLE 40

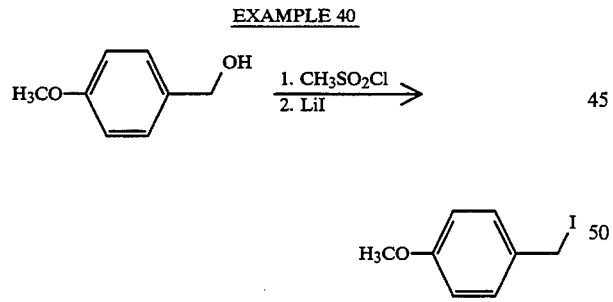

A. To a solution of 2 mL of p-methoxybenzyl alcohol in 60 mL of dry CH$_2$Cl$_2$ was added 3.45 mL of triethylamine and 1.73 mL of methanesulfonyl chloride at −25° C. After ½ hr. of stirring, the mixture was filtered, the filtrate was concentrated under high vacuum. The residue was redissolved in 50 mL of dry DMF, 2.14 g of LiI was then added at −10° C. The cooling bath was removed, and the reaction mixture was stirred at ambient temperature for 10 min. After diluting with CH$_2$Cl$_2$, the mixture was washed with water four times, then with brine, dried over MgSO$_4$, and concentrated to give 3.77 g (95%) of p-methoxybenzyl iodide which was used directly for the next step.

B. To a mixture of 0.14 g of potassium hydride in 1 mL of dry THF was added a solution of 0.248 g of the compound of formula 31C in 1 mL of THF at room temperature. After 1.5 hrs. of stirring, a 0.37 mL of p-methoxybenzyl iodide and 1 mL of HMPA (hexamethylphosphormaide) were added. The reaction mixture was stirred for 2 hr. at room temperature and 3.5 hours at 85° C. then it was stirred for overnight (14 hrs ) at room temperature After cooling to 0° C. the reaction mixture was quenched by aqueous saturated NH$_4$Cl solution. The mixture was extracted with EtOAc, dried over MgSO$_4$ and concentrated. The residue was purified by preparative TLC (5% ether in CH$_2$Cl$_2$) to give 0.130 g (35%) of a product of formula 40A, mass spectrometry m/e 368 (M+).

EXAMPLE 41

EXAMPLE 41

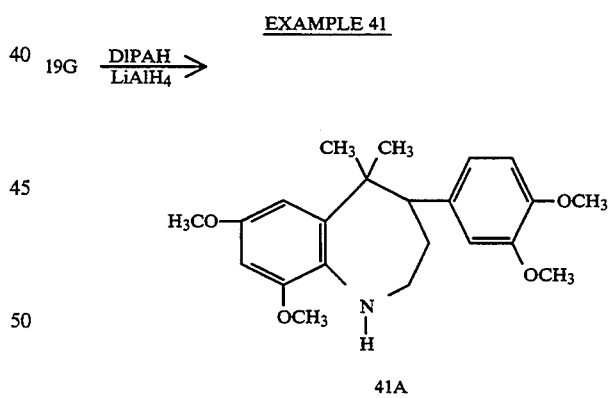

To a solution of 0.1 g of the compound of formula 19G in 2.5 mL of 1N diisopropylaluminum hydride in toluene was added 9.5 mg of lithium aluminum hydride at 0° C. The resulting mixture was stirred at 0° C. for 7 hours, and then the cooling bath was removed, and the mixture was stirred for ½ hour at ambient temperature. After recooled at 0° C., 0.2 mL of water were added to the reaction mixture. After ½ hour of stirring, 10 mL of EtOAc were added, the mixture was filtered through a pad of Celite ®. The filtrate was concentrated to give 87 mg (94%) of the product of formula 41A, mass spectrometry m/e 371 (M+). When the above reaction was carried in the absence of LiAlH$_4$ (room temperature for 25 hours), two products were isolated (4% ether in CH2Cl2). They are 41A and 41B with 35% and 36% yield, respectively.

19G ⟶

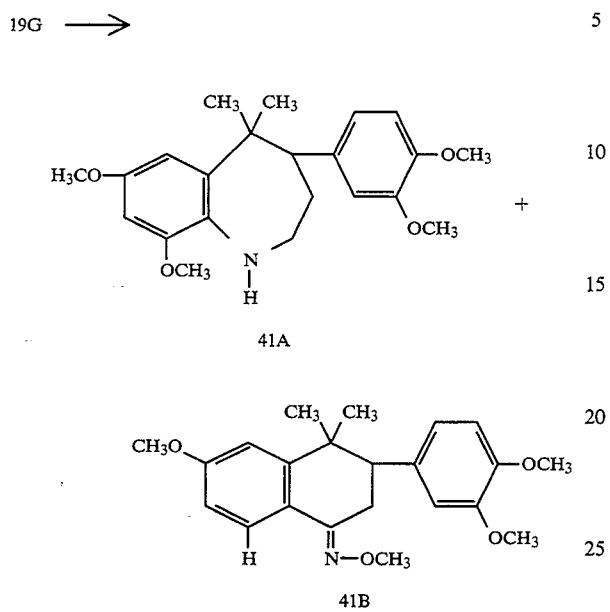

41A

41B

EXAMPLE 42

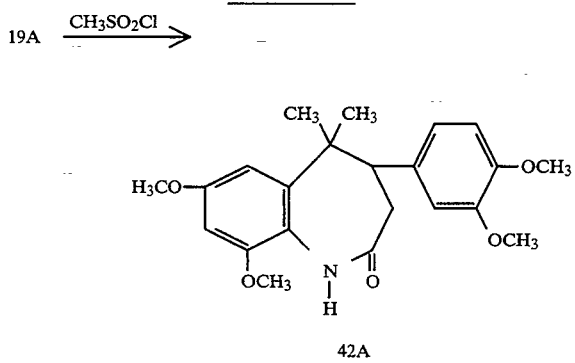

42A

To a mixture of 1.575 g of the compound of formula 19A in 15 mL of anhydrous pyridine was added 0.475 mL of methanesulfonyl chloride at 0° C. The resulting mixture was stirred for 35 min. at 0° C. and 4.5 min. at room temperature, then it was diluted with 15 mL of CH2Cl2. The resulting solution was washed four times with cold 1N HCl solution, then with brine, dried over MgSO4, and concentrated. The residue was purified by flash chromatography on SiO2 (CH2Cl2; 5% ether in CH2Cl2, 10% ether in CH2Cl2, finally 20% ether in CH2Cl2) to give 0.55 g (35%) of the product of formula 42A, mass spectrometry m/e 386 (M+1).

EXAMPLE 43

EXAMPLE 43

-continued
EXAMPLE 43

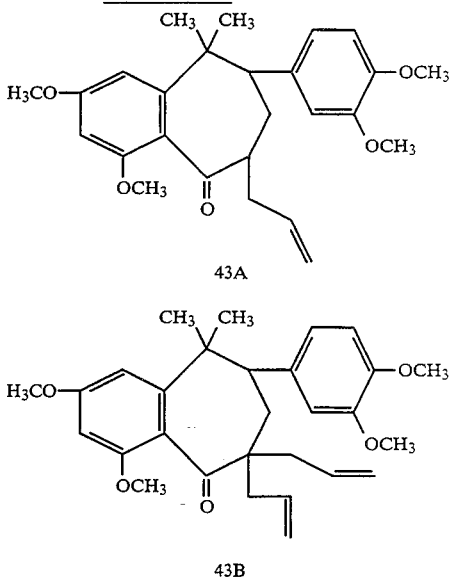

43A

43B

To a precooled (−78° C.) 1M THF of lithium bis(-trimethylsilyl)amide (1.5 ml; 1.5 mmoles) was added a dry THF (5.0 mL) solution of compound of formula 31A (384 mg; 1.0 mmoles) under N2 dropwise. After the addition, the solution was stirred at −78° C. for two hours, allyl bromide (0.35 mL) was added, then the cooling bath was removed. After stirring for another three hours, the solution was diluted with EtOAc, washed with 0.1N HCl, then with water and dried (Na2SO4). The reaction mixture was purified by flash chromatography (SiO2) (15% EtOAc/Hexanes) yielding 83 mg (18%) of compound of formula 43B [Mass spectrometry, m/e 465 (M+1)] and 230 mg (54%) of compound of formula 43A [mass spectrometry m/e 425 (M+1)].

EXAMPLE 44

EXAMPLE 44

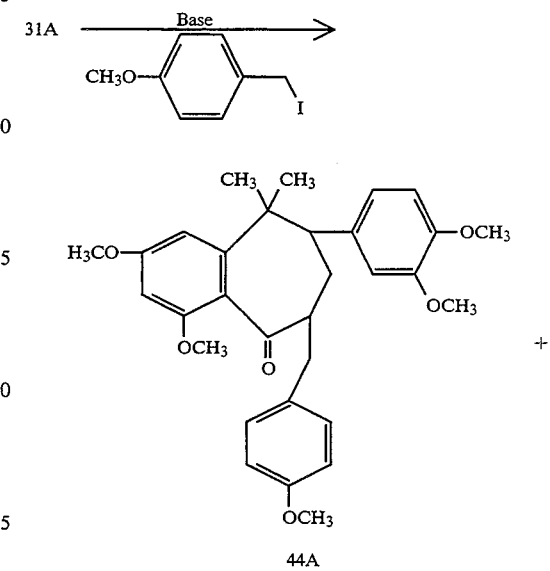

44A

-continued
EXAMPLE 44

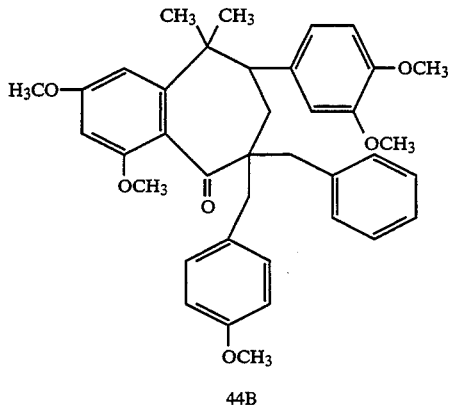

44B

A dry THF (10 mL) solution of compound of formula 31A (768 mg; 2.0 mmoles) was added slowly dropwise to a precooled (−78° C.) 1M THF solution of lithium bis(trimethylsilyl)amide (3.2 mL; 3.2 mmoles) under $N_2$. After the addition, the solution was stirred at −78° C. for two hours, then 0.70 mL of paramethoxybenzyl iodide were added dropwise. After the addition, the solution was stirred at room temperature for three hours, then diluted with EtOAc, washed with 0.1N HCl, then with water, and dried ($Na_2SO_4$). The reaction mixture was purified by flash chromatography ($SiO_2$; 25% EtOAc/Hexanes) yielding 340 mg (33%) of a compound of formula 44A [mass spectrometry, m/e 505 (M+1)] and a compound of formula 44B.

We claim:

1. A compound of formula

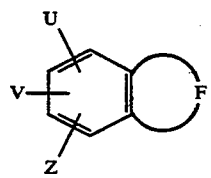

I wherein F represents:

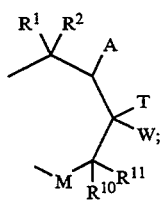

Ic

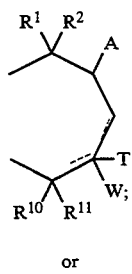

Id or

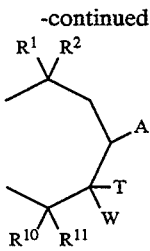

Ie or a pharmaceutically acceptable salt wherein:

the dotted line ( - - - ) represents an optional double bond, T being absent in formula Id when the dotted line represents a double bond;

A represents an aryl or an aromatic heterocyclic;

T and W are the same or different and each represents H, alkyl, alkenyl, —$OR^5$, —S—alkyl, —SQ, —$CH_2Q$, —C(O)$R^6$, or —C(O)$OR^6$;

U, V, and Z are the same or different and each represents a group selected from H, —$OR^5$, or halo;

Q represents phenyl or substituted phenyl;

$R^1$ and $R^2$ are the same or different and each represents alkyl;

each $R^5$ independently represents H, alkyl, alkanoyl, —C(O)—Q or —C(O)—N($R^6$)$_2$;

each $R^6$ independently represents H, or alkyl as defined herein or Q; and (1) when F represents Ic then M represents —$CR^7R^8$, wherein $R^7$ and $R^8$ are the same or different and each represents H or alkyl, and $R^{10}$ and $R^{11}$ together represent a carbonyl or =N—$OR^5$; or (2) when F represents Id or Ie then $R^{10}$ and $R^{11}$ together represent a carbonyl or =N—$OR^5$.

2. The compound of claim 1 wherein A represents phenyl or phenyl substituted with up to three substituents U, V and/or Z.

3. The compound of claim 1 wherein $R^1$ and $R^2$ each represent methyl.

4. The compound of claim 1 wherein T and W each represent H.

5. The compound of claim 1 wherein $R^7$ and $R^8$ each represent H.

6. The compound of claim 1 wherein U, V, and Z are the same or different and each represents a group selected from H or —$OR^5$.

7. The compound of claim 1 wherein U, V, and Z are the same or different and each represents a group selected from H or —$OR^5$ wherein $R^5$ for said —$OR^5$ represents alkyl.

8. The compound of claim 1 wherein F represents Ic, and $R^{10}$ and $R^{11}$ together represent carbonyl or =N—$OR^5$.

9. The compound of claim 8 wherein $R^{10}$ and $R^{11}$ together represent =N—OH.

10. The compound of claim 1 wherein F represents Id or Ie and $R^{10}$ and $R^{11}$ together represent carbonyl.

11. The compound of claim 1 wherein F represents Ic; $R^1$ and $R^2$ each represent methyl; $R^{10}$ and $R^{11}$ together represent carbonyl or =N—$OR^5$; A represents phenyl or phenyl substituted with up to three substituents U, V, and/or Z; and U, V, and Z are the same or different and each represents a group selected from H or —$OR^5$.

12. The compound of claim 11 wherein A represents phenyl substituted with up to three substituents U, V, and/or Z; and U, V, and Z are the same or different and each represents a group selected from H or —OR$^5$ wherein R$^5$ is alkyl.

13. The compound of claim 12 wherein R$^{10}$ and R$^{11}$ together represent carbonyl or =N—OH.

14. The compound of claim 13 wherein R$^7$ and R$^8$ each represent H.

15. The compound of claim 14 wherein T and W each represents H.

16. The compound of claim 15 wherein R$^{10}$ and R$^{11}$ together represent carbonyl.

17. The compound of claim 15 wherein R$^{10}$ and R$^{11}$ together represent =N—OH.

18. The compound of claim 1 wherein F represents Id or Ie; R$^1$ and R$^2$ each represent methyl; R$^{10}$ and R$^{11}$ together represent carbonyl or =N—OR$^5$; A represents phenyl or phenyl substituted with up to three substituents U, V, and/or Z; and U, V, and Z are the same or different and each represents a group selected from H or —OR$^5$.

19. The compound of claim 18 wherein A represents phenyl substituted with up to three substituents U, V, and/or Z; and U, V, and Z are the same or different and each represents a group selected from H or —OR$^5$ wherein R$^5$ is alkyl.

20. The compound of claim 19 wherein R$^{10}$ and R$^{11}$ together represent carbonyl or =N—OH.

21. The compound of claim 20 wherein T and W are the same or different and each represents H, alkyl, —SQ, alkenyl, or —CH$_2$Q.

22. The compound of claim 21 wherein T and W are each H; or T is methyl and W is H.

23. The compound of claim 21 wherein R$^{10}$ and R$^{11}$ together represent carbonyl.

24. The compound of claim 21 wherein R$^{10}$ and R$^{11}$ together represent =N—OH.

25. A compound having the name:
 (a) 8-[(3,4-dimethoxyphenyl)]-5,7,8,9-tetrahydro-2,4-dimethoxy-9,9-dimethyl-6H-benzocyclohepten-6-one, oxime;
 (b) 8-[(3,4-dimethoxyphenyl)]-5,7,8,9-tetrahydro-2,4-dimethoxy-9,9-dimethyl-6H-benzocyclohepten-6-one;
 (c) 8-[(3,4-dimethoxyphenyl)]-6,7,8,9-tetrahydro-2,4-dimethoxy-6,9,9-trimethyl-5H-benzocyclohepten-5-one;
 (d) 8-[(3,4-dimethoxyphenyl)]-6,7,8,9-tetrahydro-2,4-dimethoxy-9,9-dimethyl-5H-benzocyclohepten-5-one, oxime; or
 (e) 8-[(3,4-dimethoxyphenyl)]-6,7,8,9-dihydro-2,4-dimethoxy-9,9-dimethyl-5H-benzocyclohepten-5-one.

26. A pharmaceutical composition comprising a compound of claim 1 in combination with a pharmaceutically acceptable carrier.

27. A method for treating a mammal suffering from psoriasis which comprises administering an effective amount of a compound of claim 1 to said mammal.

28. The method of claim 27 wherein said compound is administered topically.

29. A method for treating inflammation in a mammal which comprises administering an anti-inflammatory effective amount of a compound of claim 1 to said mammal.

30. A method for treating allergic reactions in a mammal which comprises administering an anti-allergic effective amount of a compound of claim 1 to said mammal.

31. A compound having the name:
 8-[(3,4-dimethoxyphenyl)]-5,7,8,9-tetrahydro-2,4-dimethoxy-9,9-dimethyl-6H-benzocyclohepten-6-one oxime,
 8-[(3,4-dimethoxyphenyl)]-5,7,8,9-tetrahydro-2,4-dimethoxy-9,9-dimethyl-6H-benzocyclohepten-6-one,
 8-[(3,4-dimethoxyphenyl)]-6,7,8,9-tetrahydro-2,4-dimethoxy-6,9,9-trimethyl-5H-benzocyclohepten-5-one,
 8-[(3,4-dimethoxyphenyl)]-6,7,8,9-tetrahydro-2,4-dimethoxy-6,6,9,9-tetramethyl-5H-benzocyclohepten-5-one,
 8-[(3,4-dimethoxyphenyl)]-8,9-dihydro-2,4-dimethoxy-9,9-dimethyl-5H-benzocyclohepten-5-one,
 6,7,8,9-tetrahydro-2,4-dimethoxy-9,9-dimethyl-7-(2-pyridinyl)-5H-benzocyclohepten-5-one,
 8-[(3,4-dimethoxyphenyl)]-6,7,8,9-tetrahydro-2,4-dimethoxy-9,9-dimethyl-6-(phenylthio)-5H-benzocyclohepten-5-one,
 6,7,8,9-tetrahydro-2,4-dimethoxy-6-[(4-methoxyphenyl)methyl]-9,9-dimethyl-5H-benzocyclohepten-5-one
 6-[(3,4-dimethoxyphenyl)]-6,7-dihydro-1,3-dimethoxy-5,5-dimethyl-9-phenyl-5H-benzocycloheptene,
 6,7,8,9-tetrahydro-2,4-dimethoxy-9,9-dimethyl-7-phenyl-5H-benzocyclohepten-5-one,
 8-[(3,5-dimethoxyphenyl)]-6,7,8,9-tetrahydro-2,4-dimethoxy-9,9-dimethyl-5H-benzocyclohepten-5-one
 8-[(3,4-dimethoxyphenyl)]-6,7,8,9-tetrahydro-2,4-dimethoxy-9,9-dimethyl-5H-benzocyclohepten-5-one
 8-[(3,4-dihydroxyphenyl)]-6,7,8,9-tetrahydro-2,4-dihydroxy-9,9-dimethyl-5H-benzocyclohepten-5-one,
 8-[(3,4-dimethoxyphenyl)]-6,7,8,9-tetrahydro-2,4-dimethoxy-9,9-dimethyl-5H-benzocyclohepten-5-one, oxime,
 8-[(3,4-dimethoxyphenyl)]-5,7,8,9-tetrahydro-4-methoxy-9,9-dimethyl-6H-benzocyclohepten-6-one, or
 a pharmaceutical acceptable salt or solvate of one of the above listed compounds.

* * * * *